(12) United States Patent
Jayaprakash et al.

(10) Patent No.: US 10,920,220 B2
(45) Date of Patent: Feb. 16, 2021

(54) METHODS FOR DETERMINING RECOMBINATION DIVERSITY AT A GENOMIC LOCUS

(71) Applicant: ICAHN SCHOOL OF MEDICINE AT MOUNT SINAI, New York, NY (US)

(72) Inventors: Anitha Devi Jayaprakash, New York, NY (US); Andrew Chess, New York, NY (US); Ravi Sachidanandam, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/528,041

(22) PCT Filed: Nov. 20, 2015

(86) PCT No.: PCT/US2015/062018
§ 371 (c)(1),
(2) Date: May 18, 2017

(87) PCT Pub. No.: WO2016/081919
PCT Pub. Date: May 26, 2016

(65) Prior Publication Data
US 2017/0342408 A1 Nov. 30, 2017

Related U.S. Application Data

(60) Provisional application No. 62/082,590, filed on Nov. 20, 2014.

(51) Int. Cl.
*C12N 15/10* (2006.01)
*C07K 16/00* (2006.01)

(52) U.S. Cl.
CPC .......... *C12N 15/1093* (2013.01); *C07K 16/00* (2013.01); *C07K 2317/565* (2013.01)

(58) Field of Classification Search
None
See application file for complete search history.

(56) References Cited

U.S. PATENT DOCUMENTS

| 2012/0183969 | A1* | 7/2012 | Han | G01N 33/56972 |
|---|---|---|---|---|
| | | | | 435/6.12 |
| 2014/0051585 | A1* | 2/2014 | Prosen | B01J 19/0046 |
| | | | | 506/2 |

FOREIGN PATENT DOCUMENTS

WO    WO 2014/144713 A2    9/2014

OTHER PUBLICATIONS

International Search Report for International Patent Application No. PCT/US2015/062018 dated Mar. 27, 2016, 14 pages.

Burpo, F.J., "A critical review of PCR primer design algorithms and cross-hybridization case study," Biochemistry, vol. 218, No. 1, p. 11. Dec. 31, 2001.
Peters, D.G. et al., "Comprehensive transcript analysis in small quantities of mRNA by SAGE-lite," Nucleic acids research, 27(24), e39-e44. Dec. 31, 1999.
Warren, R.L. et al., "Exhaustive T-cell repertoire sequencing of human peripheral blood samples reveals signatures of antigen selection and a directly measured repertoire size of at least 1 million clonotypes," Genome research, vol. 21, No. 5, p. 790-797. Feb. 24, 2011.
Arden, B. et al. (1995). Mouse T-cell receptor variable gene segment families. Immunogenetics 42, p. 501-530.
Behlke, M.A. et al. (1986). Alternative splicing of murine T-cell receptor beta-chain transcripts. Nature 322, p. 379-382.
Benichou, J. et al. (2012). Rep-Seq: uncovering the immunological repertoire through next-generation sequencing. Immunology 135, p. 183-191.
Boudinot, P. et al. (2008). New perspectives for large-scale repertoire analysis of immune receptors. Mol. Immunol. 45, p. 2437-2445.
Boyd, S.D. et al. (2009). Measurement and Clinical Monitoring of Human Lymphocyte Clonality by Massively Parallel V-D-J Pyrosequencing. Sci. Transl. Med. 1, 12ra23-12ra23.
Caccia, N. et al. (1984). The T cell receptor beta chain genes are located on chromosome 6 in mice and chromosome 7 in humans. Cell 37, p. 1091-1099.
Casrouge, A. et al. (2000). Size estimate of the alpha beta TCR repertoire of naive mouse splenocytes. J. Immunol. Baltim. Md 1950 164, p. 5782-5787.
Dembić, Z. et al. Transfer of specificity by murine alpha and beta T-cell receptor genes. Nature 320, p. 232-238.
Doherty, P.C. et al. (2000). Quantitative analysis of the CD8+ T-cell response to readily eliminated and persistent viruses. Philos. Trans. R. Soc. Lond. B. Biol. Sci. 355, p. 1093-1101.
Faint, J.M. et al. (1999). Quantitative flow cytometry for the analysis of T cell receptor Vbeta chain expression. J. Immunol. Methods 225, p. 53-60.
Freeman, J.D. et al. (2009). Profiling the T-cell receptor beta-chain repertoire by massively parallel sequencing. Genome Res. 19, p. 1817-1824.
Haqqi, T.M. et al. (1989). Identification of T-cell receptor V beta deletion mutant mouse strain AU/ssJ (H-2q) which is resistant to collagen-induced arthritis. Immunogenetics 29, p. 180-185.

(Continued)

*Primary Examiner* — Katherine D Salmon
(74) *Attorney, Agent, or Firm* — Morgan, Lewis & Bockius LLP

(57) ABSTRACT

The present disclosure relates to methods for determining recombination diversity at a genomic locus of interest. The method includes fragmenting nucleic acids isolated from immune cells, ligating adaptors to the fragmented or amplified nucleic acids, and selectively amplifying nucleic acids containing a recombined junction at the genomic locus of interest. Selective amplification is achieved by using a first primer that hybridizes to an adaptor sequence and a second primer that hybridizes at a constant region downstream of the recombined junction. The selectively amplified nucleic acids may be sequences and analyzed to determine recombination diversity at the genomic locus.

20 Claims, 28 Drawing Sheets
Specification includes a Sequence Listing.

(56) References Cited

OTHER PUBLICATIONS

Hedrick, S.M. et al. (1984). Isolation of cDNA clones encoding T cell-specific membrane-associated proteins. Nature 308, p. 149-153.
Hozumi, N. et al. (1976). Evidence for somatic rearrangement of immunoglobulin genes coding for variable and constant regions. Proc. Natl. Acad. Sci. U. S. A. 73, p. 3628-3632.
Klenerman, P. et al. (2002). Tracking T cells with tetramers: new tales from new tools. Nat. Rev. Immunol. 2, p. 263-272.
Ladi, E. et al. (2006). Thymic microenvironments for T cell differentiation and selection. Nat. Immunol. 7, p. 338-343.
Lane, J. et al. (2010). From IMGT-ONTOLOGY to IMGT/LIGMotif: the IMGT standardized approach for immunoglobulin and T cell receptor gene identification and description in large genomic sequences. BMC Bioinformatics 11, p. 223.
Lefranc, M.-P., (2009). IMGT, the international ImMunoGeneTics information system. Nucleic Acids Res. 37, D1006-D1012.
Mak, T.W.et al. The T cell antigen receptor: "The Hunting of the Snark." Eur. J. Immunol. 37, S83-S93.
Mazer, B.D. (1991). An ELISA spot assay for quantitation of human immunoglobulin-secreting cells. J. Allergy Clin. Immunol. 88, p. 235-243.
Medzhitov, R. (2009). Approaching the asymptote: 20 years later. Immunity 30, p. 766-775.
Mora, T. et al. (2010). Maximum entropy models for antibody diversity. Proc. Natl. Acad. Sci. U. S. A. 107, 5405-5410.
Nadel, B. et al. (1998a). Sequence of the spacer in the recombination signal sequence affects V(D)J rearrangement frequency and correlates with nonrandom Vkappa usage in vivo. J. Exp. Med. 187, p. 1495-1503.
Nadel, B. et al. (1998b). Decreased frequency of rearrangement due to the synergistic effect of nucleotide changes in the heptamer and nonamer of the recombination signal sequence of the V kappa gene A2b, which is associated with increased susceptibility of Navajos to Haemophilus influenzae type b disease. J. Immunol. Baltim. Md 1950 161, p. 6068-6073.
Nanda, N. K. et al. (1991). Limitations in plasticity of the T-cell receptor repertoire. Proc. Natl. Acad. Sci. U. S. A. 88, p. 9503-9507.
Nikolich-Zugich, J. et al. (2004). The many important facets of T-cell repertoire diversity. Nat. Rev. Immunol. 4, p. 123-132.
Rezuke, W.N. et al. (1997). Molecular diagnosis of B- and T-cell lymphomas: fundamental principles and clinical applications. Clin. Chem. 43, p. 1814-1823.
Schatz, D.G. et al. (2011). Recombination centres and the orchestration of V(D)J recombination. Nat. Rev. Immunol. 11, p. 251-263.
Sha, W.C. et al. (1988). Positive and negative selection of an antigen receptor on T cells in transgenic mice. Nature 336, p. 73-76.
Wang, C. et al. (2010). High throughput sequencing reveals a complex pattern of dynamic interrelationships among human T cell subsets. Proc. Natl. Acad. Sci. U. S. A. 107, p. 1518-1523.
Weinstein, J.A. et al. (2009). High-throughput sequencing of the zebrafish antibody repertoire. Science 324, p. 807-810.
Williams, A.F. (1984). The T-lymphocyte antigen receptor—elusive no more. Nature 308, p. 108-109.
Yanagi, Y. et al. (1984). A human T cell-specific cDNA clone encodes a protein having extensive homology to immunoglobulin chains. Nature 308, p. 145-149.
Zinkernagel, R.M. et al. (1974). Restriction of in vitro T cell-mediated cytotoxicity in lymphocytic choriomeningitis within a syngeneic or semiallogeneic system. Nature 248, p. 701-702.
Kedzierska, K, et al., Tracking phenotypically and functionally distinct T cell subsets via T cell repertoire diversity,Mol Immunol., 45(3):607-18(2008).

* cited by examiner

Figure 14

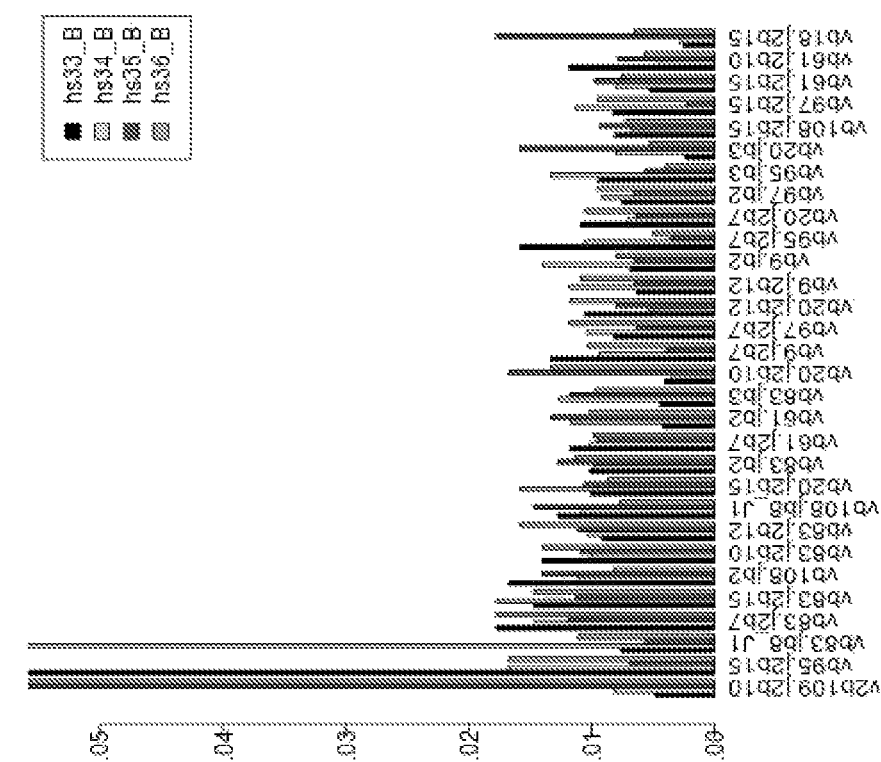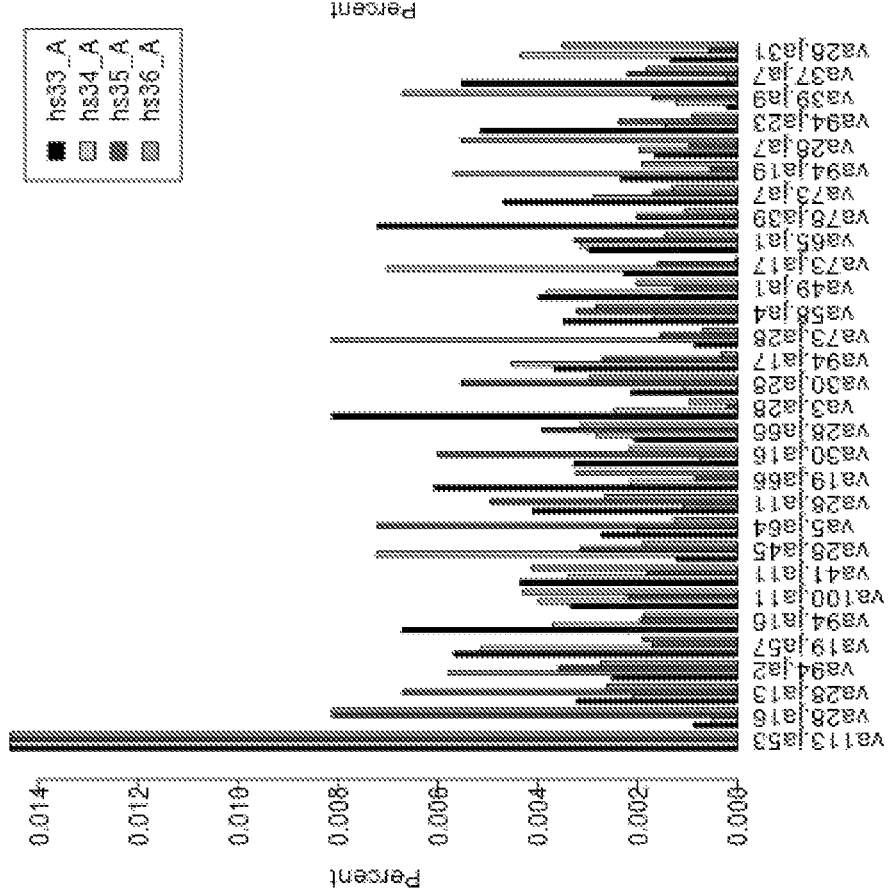
Figure 17

Primers used to isolate Alpha TCR sequences in PCR 1 for Mouse:

F = universal adapter
AATGATACGGCGACCACCGAGATCTACACTCTTTCCCTACACGACGCTCTTCC GATC*T
R= TCR C alpha primer (mouse) TCCTGAGACCGAGGATCTTTTA

Primers used to isolate Alpha TCR sequences in PCR 2 for Mouse:

F = universal adapter
AATGATACGGCGACCACCGAGATCTACACTCTTTCCCTACACGACGCTCTTCC GATC*T
R= TCR C alpha primer (mouse)
CAAGCAGAAGACGGCATACGAGAT[CGTGAT]GGTACACAGCAGGTTCTGGGT TCTGGATGT

Primers used to isolate Beta TCR sequences in PCR 1 for Mouse:

F = universal adapter
AATGATACGGCGACCACCGAGATCTACACTCTTTCCCTACACGACGCTCTTCC GATC*T
R= TCR C beta primer (mouse)
AAGGAGACCTTGGGTGGAGTCA

Primers used to isolate Beta TCR sequences in PCR 2 for Mouse:

F = universal adapter
AATGATACGGCGACCACCGAGATCTACACTCTTTCCCTACACGACGCTCTTCC GATC*T
R= TCR C beta primer (mouse)
CAAGCAGAAGACGGCATACGAGAT[TGGTCA]CCTTGGGTGGAGTCACATTTC TCAGATCCT

Primers used to isolate Alpha TCR sequences in PCR 1 for Human:

F = universal adapter
AATGATACGGCGACCACCGAGATCTACACTCTTTCCCTACACGACGCTCTTCC GATC*T
R= TCR C alpha primer (human)
CACTGGATTTAGAGTCTCTCAGC

Primers used to isolate Alpha TCR sequences in PCR 2 for Human:

F = universal adapter
AATGATACGGCGACCACCGAGATCTACACTCTTTCCCTACACGACGCTCTTCC GATC*T
R= TCR C alpha primer (human)
CAAGCAGAAGACGGCATACGAGAT[TGGTCA]GTGACTGGAGTTCAGACGTGTG
CTCTTCCGATCTNNNGCTGGTACACGGCAGGGTCA

Primers used to isolate Beta TCR sequences in PCR 1 for Human:

F = universal adapter
AATGATACGGCGACCACCGAGATCTACACTCTTTCCCTACACGACGCTCTTCC GATC*T
R= TCR C beta primer (human) TGCTTCTGATGGCTCAAACA

Primers used to isolate Beta TCR sequences in PCR 2 for Human:

F = universal adapter
AATGATACGGCGACCACCGAGATCTACACTCTTTCCCTACACGACGCTCTTCC GATC*T
R= TCR C beta primer (human)
CAAGCAGAAGACGGCATACGAGAT[CACTGT]GTGACTGGAGTTCAGACGTGTG
CTCTTCCGATCTNNNNNNNCAGCGACCTCGGGTGGGAAC

*Figure 23*

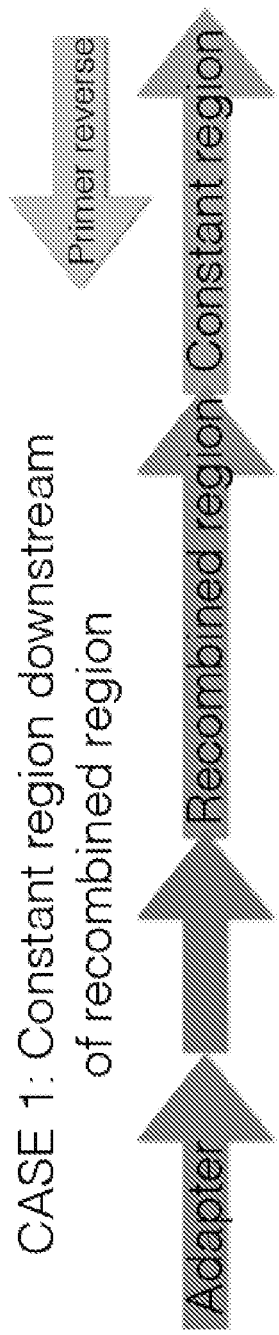
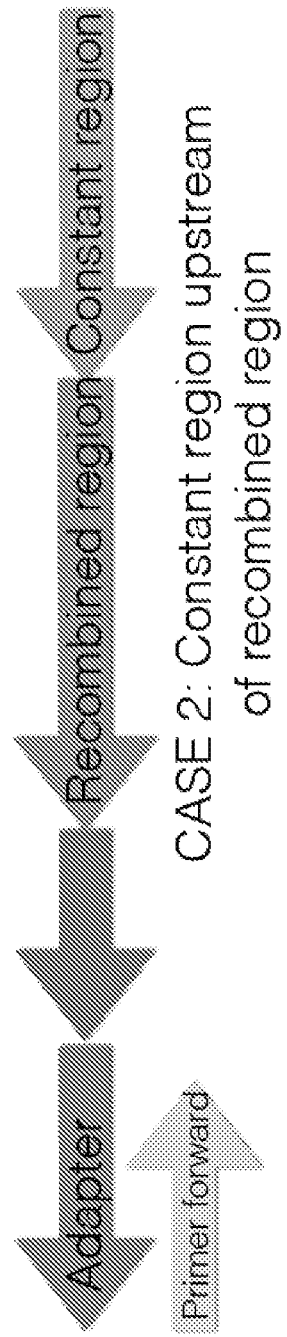
*Figure 27*

METHODS FOR DETERMINING RECOMBINATION DIVERSITY AT A GENOMIC LOCUS

CROSS-REFERENCE TO RELATED APPLICATIONS

This application is a National Stage of International Patent Application No. PCT/US2015/062018 filed Nov. 20, 2015 and published as WO 2016/081919 A1, which claims priority to U.S. Provisional Application No. 62/082,590 filed Nov. 20, 2014, the entire contents of which applications are incorporated herein for all purposes by this reference.

FIELD OF THE APPLICATION

This application generally relates to methods for generating a T-cell receptor repertoire (TCRR) from a complex population of cell types based on isolation and fragmentation of mRNA from any tissue or cells. The strategy outlined below can be modified to study any region of the genome or transcriptome whose partial sequence is known. It is possible to address the copy number variations of any genes, or to quantify the repeat elements by just changing the C sequence specific to TCR to other biological questions. For example, the C sequence can be replaced by a 5'-terminal end, or 3'-terminal end, of a gene whose copy number variation is in question.

BACKGROUND

Introduction

Robert Koch was the first to show that microbes can cause diseases in 1876 and now we are well aware that we are surrounded by an astounding number of invisible harmful microbes. However, despite the near constant assault by disease-causing microbes, we mostly survive these attacks. It is because of a wonderful system in place in our body, called the immune system. This wonderful system can handle almost anything thrown at it, and avoids attacking the "self" and the adaptive part of the immune system tailors its response based on each individual microbe. It wasn't clear if the genetic diversity that was required for the synthesis of these infinite host proteins is generated during evolution and carried in the germ line or if it occurs during development. Based on the one gene-one enzyme hypothesis, it was thought that a separate gene for every polypeptide is made in the germ line that ultimately synthesizes a unique antibody. Where does the diversity arise? How can the genome encode this? These questions were one of the greatest mysteries in biology (after the structure and role of DNA) and were conclusively answered by Susumu Tonegawa who showed in 1976 (Hozumi and Tonegawa, 1976) that there were "Variable" regions that combined with a "Constant" region through DNA rearrangements to give the diversity during development.

The earliest systems of defense against a pathogen can be observed in bacteria, which use restriction endonucleases to cut double stranded viral DNA (Arber, 1974). Other mechanisms like antimicrobial peptides, phagocytosis, and the complement system evolved in ancient eukaryotes that are the foundation of the "innate immune system" and can be seen throughout plants and animals. A more specific and more advanced system of defense is the "adaptive immune system," that provides enhanced protection and immunological memory against specific pathogens. This system is believed to have evolved with the jawed vertebrates (Hsu, 2011; Schluter et al., 1999). In mammals, physical and chemical barriers like the tight junctions of the epithelial cells provide the first line of defense against a pathogen. When this barrier is breached, cells of the innate immune system that includes, macrophages, neutrophils and dendritic cells, through their invariant receptors and signaling events, can recognize a pattern that distinguishes a pathogen from a host cell and engulf it. This facilitates the removal of a pathogen, but does not confer any immunological memory. When the innate immune system fails to eliminate a specific pathogen, the professional antigen presenting cells (APC) like dendritic cells, B cells or macrophages, alert the adaptive immune system (Medzhitov, 2009).

Lymphocytes (B cells or T cells) are the key players of the adaptive immune system and can mount a specific immune response against virtually any foreign antigen. Each mature lymphocyte (B or T type) carries a variant antigen receptor that is unique and together they constitute a repertoire of receptors, which can identify almost any kind of pathogen, thereby conferring specificity and enhanced protection and in many cases, conferring life-long protective immunity to reinfection with the same pathogen. This diversity is achieved by DNA-recombination at the locus of the receptor genes, which forms a multitude of recognition motifs, one for each cell. The lymphocytes encounter a pathogen presented by the APCs in the peripheral lymphoid organ that includes the lymph nodes, the spleen, and the mucosal lymphoid tissues and upon recognition are clonally amplified and mediates a humoral (by B cells) or cell mediated response (by T cells) (Charles A Janeway et al., 2001). T-lymphoid cells, in particular are critical components of the adaptive immune system, as they not only recognize a wide variety of intracellular pathogens and tumor cells through their surface receptors called the T cell receptor (TCR) but also regulate the B cells, by either promoting their proliferation or suppressing them. TCRs differ from the B cell antigen binding receptor in two main ways. One, that the TCRs are membrane bound (each T-cell expressing ~$10^5$ molecules on its surface) and the other that the TCRs unlike the B cells, can recognize an antigen only when it is combined with another molecule of the so-called major histocompatibility complex (MHC) (Charles A Janeway et al., 2001).

History of the T-Cell Receptor

While it was easier to elucidate the structure of the antibody protein, it was a difficult task to define the nature of the TCR and isolate its genes. In the 1930's antibodies were discovered as "antitoxins" and the structure of this protein revealed by Rodney Porter and Gerald Edelman in the 1950's and 1960's and the genes for the BCR proteins were eventually cloned. In 1976 Tonegaw and coworkers demonstrated that there were variable regions that combined with a constant region through DNA rearrangements to give the diversity (Hozumi and Tonegawa, 1976). Miller and Mitchell in 1968 showed that there were two kinds of lymphocytes cells, one from the thymus (later called as T cells) and the other from the bone marrow (B cells) (Miller, 2004).

A major reason for this success in the hunt for TCR was that, apart from being expressed on the surface of the B cells, it was also secreted in large quantities as antibodies. However, it was extremely difficult to purify sufficient TCR proteins to perform structural analysis or gene cloning studies. It was not until the 1970's that immunologists were convinced that the T cell receptor even existed (Mak, 2007). Between 1960 and 1983 intense efforts to establish reagents designed to identify and characterize the TCR protein took place but in vain. Two review articles of that time entitled "The T lymphocyte antigen receptor: paradigm lost" and "Finding the T-cell antigen receptor: past attempts and future promise" summarized the quest and concluded that nothing had come out of this enormous exploration (Jensenius and Williams, 1982; Kronenberg et al., 1983).

A major breakthrough came in 1976 when Rolf Zinkernagel and Peter Doherty showed that the activation of the T cell was dependent not just on the recognition of antigen but also required the recognition of MHC molecules (Zinkernagel and Doherty, 1974). In 1982, James Allison and his co-workers generated a monoclonal antibody (mAb) that was specific to a particular T cell lymphoma thus catching the first true glimpse of the TCR (Allison et al., 1982) and within a year many reports of such mABs that were specific to T cell clone-specific structures, T cell hybridomas or T cell leukemia cell lines appeared. Peptide maps by these groups showed that this protein was a dimer and had two distinct chains and equivalent chains from clones of different specificities had peptides that were both different and identical (Williams, 1984).

In the early 1980's Tak Wah Mak's group undertook a differential hybridization approach to clone the human TCR genes. They had previously used this methodology to isolate retroviral genes that were differentially expressed in rapidly transforming viruses. This subtractive hybridization technique was pursued in parallel by Mark Davis group in Stanford University but in the Mouse TCR and two back-to-back papers appeared in Nature by these groups reporting the structure of the human and mouse beta chain of the TCR (Hedrick et al., 1984; Yanagi et al., 1984). Within a year, the structure of the alpha chain was also revealed. By the mid-1980s, the general principles of thymic selection leading to central tolerance were swiftly established (Sha et al., 1988; Snodgrass et al., 1985) and by 1986 Michael Steinmetz's group conclusively proved that a single TCR protein recognizes both the MHC and a combination of antigenic peptides (Dembić et al., 1986).

Now it is clear that the TCR is a heterodimer consisting of an alpha ($\alpha$) and a beta ($\beta$) chain (95% of T cells), or gamma and delta ($\gamma/\delta$) chains (5% of T cells). Each chain has a constant region that is anchored to the cell membrane and a variable region, at the N terminal end. The exposed region of the TCR has hyper-variable regions called the complementarity determining regions (CDRs). While CDR1 and CDR2 are encoded by $V_\alpha$ and $V_\beta$, the CDR3 is found across the VDJ junction (Charles A Janeway et al., 2001).

The Importance of T Cells and their Roles in Autoimmunity

T cells are the central players in the immune system with effector functions to kill infected (or abnormal) cells, and regulate other T-cells and B-cells. The TCR expressed by T cells allows them to recognize antigenic peptides presented to them by the major histocompatibility complexes (MHC) on the surfaces of cells (MHC class I on all cells, MHC class II only on true antigen presenting cells). All TCRs are heterodimers of receptor pairs: the majority of T cells, called $\alpha/\beta$ T-cells, express the $\alpha$-$\beta$ receptor pair; the rest (<10%), called $\gamma/\delta$ T-cells, express the $\gamma$-$\delta$ pair. All TCR genes undergo DNA rearrangements that allow the generation of a vast repertoire ($\sim 10^{16}$) of potential amino acid sequences (Kedzierska K, et al., *Mol Immunol.*, 45(3):607-18(2008)). Each TCR has multiple variable regions (V) and a number of 'joining' regions (J) before the constant (C) region (FIG. 1). Of the several complementarity determining regions (CDR), that determine the antigen-specificity of the TCR, the CDR3 (the junction of V-J) is the most important[2]-[4]. For the ß and $\gamma$ TCRs, one of a few 'diversity' (D) regions is interposed between the V and the J. The diversity in CDR3 is generated by the choice of V, D (for $\beta$, $\gamma$) and J, and by deletions and non-templated insertions.

Normally, T-cells will not recognize "self" proteins. In autoimmune disorders, this restraint is lost and certain self-antigens are targeted, leading to a range of disorders, from psoriasis to rheumatoid arthritis depending on the tissue under attack. Only limited work has gone into recognizing signatures of autoimmunity in the TCR repertoire, which have utility as biomarkers and potential targets for therapy.

Thymic Selection of the TCR Repertoire:

Donor hematopoietic precursors (Thymic settling precursors, TSP) seed the thymus at the cortico-medullary junction (CM junction) about day 12 of gestation in mice. Specialized compartments in the thymus direct and support the development of T cells that include chemokines, adhesion molecules, notch ligands, lymphotoxin receptors etc. TSP's migrate to the cortex and are called early T lineage progenitors (ETP) where they undergo a series of migrations that regulates their developmental program as well. The earliest thymocyte progenitors are termed as DN1 (Double Negative 1) cells that are positive for the surface marker CD44 but negative for CD4, CD8 and CD25. The development then proceeds to make DN2, DN3a cells. At this stage, the cells undergo cell fate decisions that can lead to the formation of natural killer T (NKT) cells, $\gamma\delta$ cells or the conventional $\alpha\beta$-cells (Yashiro-Ohtani et al., 2010).

Two important checkpoints occur during further maturation of thymocytes. The first checkpoint takes place during the transition from DN3a to DN3b cells. During this time, the beta chain locus undergoes VDJ recombination and only those populations of DN3a cells that have generated a functional TCR beta chain get selected to form the DN3b cells. Failure to do so results in apoptosis of the immature thymocytes. At this time, a non-polymorphic pre-Tα (pTα) chain is also produced (pTα has an extended cytoplasmic tail when compared to mature Tα). The functional beta chain along with pTα and CD3$\gamma$, CD3$\delta$, CD3$\epsilon$ and TCR$\zeta$ subunits, forms the pre-TCR complex. The second checkpoint occurs in the thymus through positive and negative selection of the DP thymocytes, resulting in the establishment of tolerance. Positive selection occurs in the cortex, where the Tcra locus undergoes rearrangement and pTα is replaced by the clonotypic $\alpha\beta$ TCR complex. The DP cells whose functional TCR receptor is capable of interacting with the MHC ligands on thymic epithelial cells, is selected for further maturation into CD4+ or CD8+ single positive (SP) cells. Cells that fail to undergo this positive selection undergo cell death. Those TCR receptors that exhibit high affinity for self-antigens-MHC complexes are removed from the repertoire via apoptosis (Negative selection). Mature and self-tolerant T cells are exported into circulation (Ladi et al., 2006; Michie and Zúñiga-Pflücker, 2002).

Importance of Studying T-Cells and T-Cell Receptor Repertoires (TCRRs)

T cells induce a cell-mediated response to specific antigens, once a MHC molecule on the surface of an infected cell presents an antigen. This means the T cells are recruited to a particular site, unlike the B cells that generate an "action at a distance" by secreting antibodies (proteins) in response to an antigen, which are transported to the site of infection through the blood-lymphatic system. Therefore it is easier to isolate the T cell transcripts once the site of infection is known and look at the response of the T cell repertoire to the antigen. Another important reason is that T cells not only recognize a wide variety of intracellular pathogens and tumor cells (TCR) but also regulate the B cells, by either promoting their proliferation or suppressing them (Boudinot et al., 2008).

The immune repertoire can be used as a powerful tool to study the lymphocyte populations in pathological situations like infections etc. as well as during the development of the immune system. Understanding the response of the repertoire to pathogens can also provide insights into the rules and regulatory patterns that govern their interdependent variability and their co-evolution over time. A hole in the TCR repertoire can have serious consequences in the ability of an individual to respond to an antigenic stimulus. Previous studies have shown that mice strains that lost 50% of their V-beta segments from the germ line repertoire demonstrated limited plasticity and could not recruit alternate gene segments to fight certain antigens. These mice with their truncated repertoire could not respond to two of the antigenic determinants, sperm whale myoglobin and myelin basic protein (Nanda et al., 1991). This is only one example of many (Frankel et al., 1991; Haqqi et al., 1989).

Importance of Studying T-Cells and T-Cell Receptor Repertoires (TCRRs)

The TCR-repertoire can be monitored, either through functional assays or through monitoring the TCR at the DNA, RNA or proteomic levels (Rezuke et al., 1997). Functional assays of T cell function are rather labor intensive and difficult to standardize across different labs. The mixed-lymphocyte reaction (MLR, also known as mixed-leukocyte reaction) is a classical method, which measures proliferation secondary to allo-reactivity. Other functional assays include the CTL—cytotoxic T lymphocyte—assay and limiting dilution-based assays. ELISASPOT is an ELISA-based method of examining antigen-specific T cell responses (Mazer et al., 1991). Flow-cytometry has also been employed as a method for analyzing epitopes of TCRs (Faint et al., 1999; Klenerman et al., 2002). However, proteomic assays, usually based on antibodies, present a variety of technological challenges as well as the limitation on the number of monoclonal antibodies that are available for the variable regions. While populations of T cells that are clonal against a defined epitope can be studied using Flow Cytometry, more complex studies like global alterations in the repertoire against variable genetic background cannot be answered (Boudinot et al., 2008).

Analyses of T cell receptor gene DNA rearrangements have been seen as a potentially excellent way to monitor the T cells repertoire taking advantage of the inordinate number (millions) of possible TCR gene rearrangements that are possible. Non-sequencing methods have predominated, including the CDR3-length distribution assay (CDR3-LD) can detect prevalence of oligo-clonality even though it only measures the distribution of CDR3 lengths and not the actual sequence (Rock et al., 1994). A problem inherent to DNA-based measurements is the presence of a non-functional TCR copy in each cell and difficulty of identifying the functional version from the DNA sequence. In contrast, RNA measurements directly measure the abundance of the functional copies.

Current Limitations and Challenges

The TCR repertoire can thus be monitored to detect a diseased state, and some methods to do so are used clinically (Nanda et al., 1991). However, the ability to fully explore the potential for the TCR repertoire to be a biomarker both in cases of infection, transplant, autoimmunity, allergy and potentially other medical conditions still remains a challenge. Exhaustively sequencing the TCR repertoire is challenging, given both the low abundance and large numbers of distinct TCR transcripts. Even if the sequencing were exhaustive, analysis of the repertoire is a challenge, due to the rarity of certain combinations and the non-template additions exhibited by some of the transcripts. Sequencing approaches to date have employed PCR with combinations of primers to attempt to exhaustively amplify the TCR repertoire. However, all such PCR based approaches have the inherent potential for biases introduced by different efficiencies of different primers (Boyd et al., 2009; Wang et al., 2010; Weinstein et al., 2009). SNPs in the samples can cause primers to have lower efficiency or fail. This method also does not allow for discovery of novel elements or extensive mutations in individuals. Another approach is the use of RACE-PCR to avoid using V-based primers, which suffers from non-specific amplification and low efficiency (less than 1% of reads cover CDR3) (Freeman et al., 2009; Warren et al., 2011). Hence, it is widely acknowledged that all current methods of TCR repertoire analysis have significant limitations (Benichou et al., 2012).

Current Strategies for Monitoring the TCR Repertoire (TCRR):

Monitoring the TCRR has long been appreciated as a way to study the immune response, which can be performed through functional assays or using DNA, RNA or proteins. A problem inherent to DNA-based measurements is the presence of a nonfunctional TCR copy in each cell. In contrast, RNA measurements directly assess the abundance of the functional copies. So far, non-sequencing methods have predominated, including the CDR3-length distribution assay (CDR3-LD), which can detect the prevalence of oligoclonality even though it only measures the distribution of CDR3 lengths. Flow-cytometry has also been employed as a method for analyzing epitopes of TCRs but is limited by the availability of antibodies.

The Need for Novel Deep-Sequencing Strategies for Monitoring the TCRR

Sequencing is the best approach to measuring the TCRR. Most approaches to date have employed PCR with combinations of primers to amplify a broad swath of the TCRR. However, substantial bias can be introduced by differing PCR primer efficiencies. SNPs in the samples can cause primers to have lower efficiency or fail. This method also does not allow for discovery of novel elements or extensive mutations in individuals. Lastly, the complicated process of multiplexing and carrying out many PCR reactions makes it difficult to implement. Another approach is the use of RACE-PCR to avoid using V-based primers, which suffers from non-specific amplification and low efficiency (less than 1% of reads cover CDR3). Hence, it is widely acknowledged that all current methods of TCRR analysis have significant limitations and as such there is a need in the art to develop additional novel methods to address these limitations.

BRIEF SUMMARY

Present Disclosure

The T-seq technique described herein overcomes the limitations of current approaches. The method includes ligation of universal primers to fragmented mRNA and amplification (e.g., via nested PCR) with 3'-oligos hybridizing to the constant C region and the universal 5'-adapter (FIG. 3). This unbiased approach is highly efficient (>95% of reads are CDR3, for TCRR of α and β) and allows discovery of novel segments while reducing the sequencing cost substantially.

The focus of the present disclosure is to describe this cost effective, accurate and rapid method to monitor the TCRR and define the TCR locus properly, as well as to employ the results obtained in order to correct errors and omissions in annotation. Through use of these techniques, insights into the TCR repertoire will be gained, and this will have great implications for diagnosis and treatment of various disorders in the clinic, all of which will help further personalized medicine.

In one embodiment, the present disclosure provides a method for determining recombination diversity at a genomic locus of interest in a subject. The method includes isolating nucleic acids from a biological sample containing immune cells from the subject. The method also includes fragmenting the isolated nucleic acids, to form a plurality of fragmented nucleic acids. The method also includes ligating first adaptor nucleic acids to the ends of respective nucleic acids corresponding to the plurality of fragmented nucleic acids, to form a plurality of ligated nucleic acid fragments. The first adaptor nucleic acids include a first hybridization region having a first predefined hybridization sequence. The method also includes selectively amplifying respective ligated nucleic acid fragments, in the plurality of ligated nucleic acid fragments, containing a recombed junction at the genomic locus of interest, to form a plurality of amplified nucleic acid fragments. Amplification uses a first primer that hybridizes, at the first hybridization region, to the Crick strand of respective ligated nucleic acid fragments in the plurality of ligated nucleic acid fragments. Amplification also uses a second primer that hybridizes, at a first site in a constant region downstream of the recombined junction at the genomic locus of interest, to the Watson strand of respective ligated nucleic acids containing the recombined junction at the genomic locus of interest in the plurality of ligated nucleic acid fragments. The method also includes sequencing amplified nucleic acid fragments in the plurality of amplified nucleic acid fragments.

In one embodiment, the present disclosure provides a method for generating a T-cell receptor repertoire (TCRR) from a T-cell population, the method comprising: a) isolating mRNA from the T-cell population; b) fragmenting the mRNA to obtain a collection of mRNA fragments having a mean fragment length that is less than about 600 bp; c) preparing cDNA from the collection of fragments; d) ligating at least a first adapter module to the cDNA; wherein the first adapter module ligates to a first end of the cDNA; e) performing a first round of PCR amplification using a first primer and a second primer, wherein the first primer binds to a first region and the second primer binds to a second region in the first round of PCR amplification, wherein the first region is at least partially in the first adapter and the second region is in the C-region, thereby obtaining a plurality of first amplified products; and f) performing a second round of PCR amplification on the plurality of first amplified products using a third primer and a fourth primer thereby deriving a plurality of second amplified products, wherein the third primer binds to a third region and the fourth primer binds to a fourth region in the second round of PCR amplification, the third region is at least partially in the first adapter and the fourth region is in the C-region, an average nucleotide distance between the first and the second region across the plurality of first amplified products is greater than an average nucleotide distance between the third region and the fourth region across the plurality of second amplified products, and the fourth region is located at least partially between the first and second regions.

BRIEF DESCRIPTION OF THE DRAWINGS

FIG. 14: The sequences of the end of a particular V and the start of a particular J is shown above. The middle table shows the peptide sequence from top 10 different CDR3 nucleotide sequences made by the selected VJ combination. Peptides with the same amino acid sequence are highlighted by the same colors. We observe that the first four-peptide sequence is the same in all mice strains independent of the nucleotide sequence. The bottom panel lists the nucleotide sequence and the frequency of this top CDR3 peptide sequence of two mice strains.

FIG. 17: Distribution of V,J combinations for four different humans, α (left panel) and β (right). There is a lot of variability between humans, in both α and β and measuring both accurately might be important for clinical applications.

FIG. 23: The adapter sequences and constant regions used in the experiments in these examples are included in the list of primers below. For example, the forward primer is adapter 1 and the reverse primers contain both adapter 2 and constant regions of either the alpha or the beta TCR. Regarding annotation for the primer sequences below, the constant regions (C-regions) are bolded and underlined. In the reverse primers, anything after the box brackets ([ ]) is the constant region in bold and underlined, and anything before the brackets is the adapter sequence.

FIG. 27: Illustrates an amplification scheme starting from RNA fragments containing the recombined region, in accordance with some implementations.

DETAILED DESCRIPTION

I. Introduction

The adaptive immune system of jawed vertebrates is complex, consisting of several components such as B cells and T cells. The B cells mature in the bone marrow, and generate antibodies. T cells mature in the thymus and exhibit receptors on their surface. The vast diversity of receptors/antibodies, generated by similar genomic rearrangements and clonal expansion in both cell types, enables the recognition and elimination of invaders.

Figure 1:
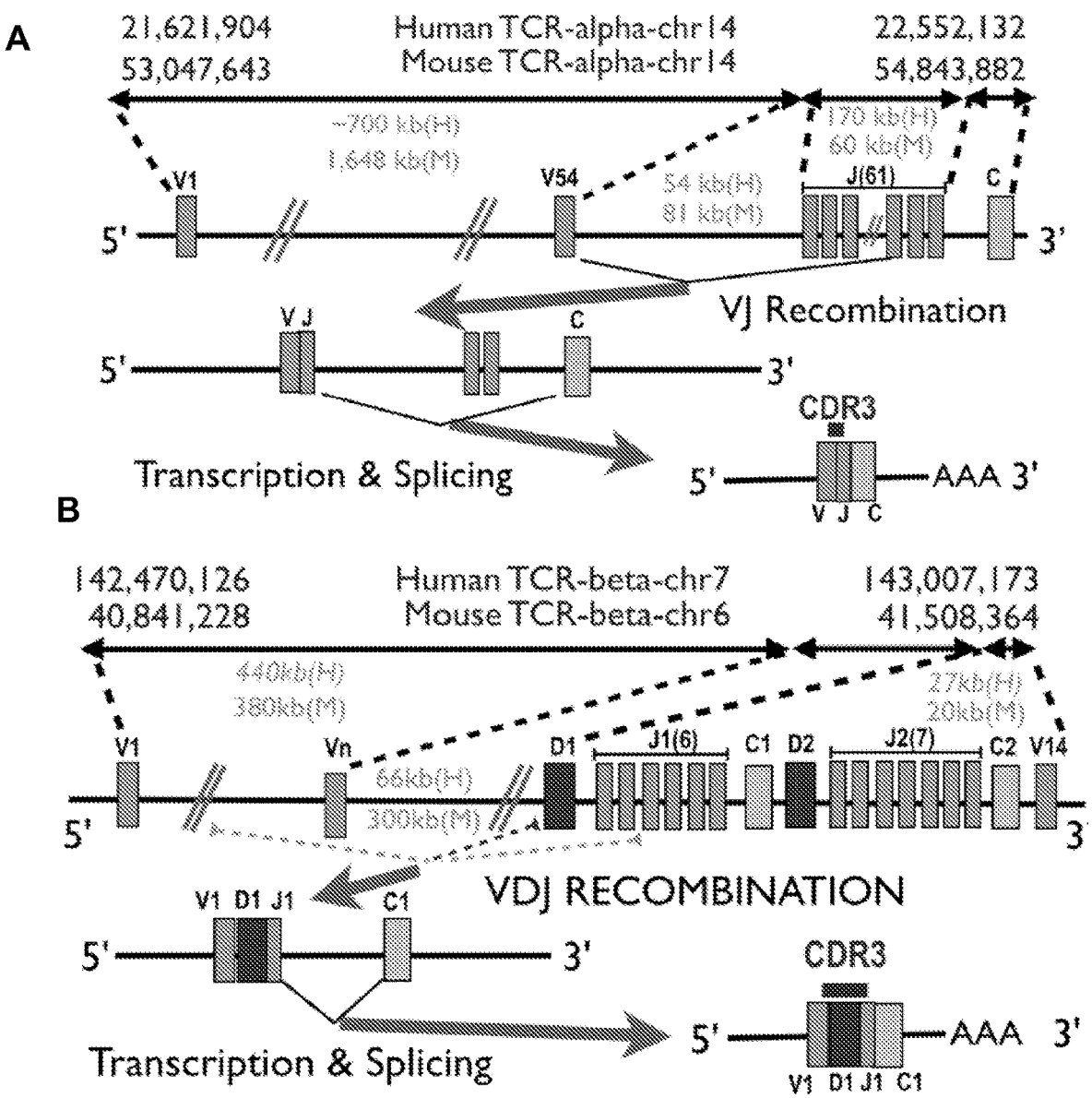
FIG. 1: A) Genomic structure of mouse and human TCR α, with blocks of V, J and C noted. There are many choices of V (rust brown, ≈100 segments, ≈400 nt long), and J (violet≈47 segments, ≈65 nt long), but only one C (green, ≈1000 nt). The final transcript is a combination of a V, a J and the C. B) Genomic structure of mouse and human TCR β. Many choices of V (rust brown color, 34 segments, ≈400 nt long), two D's (blue color, ≈15 nt long), two groups of J and C, J1 (violet, 6 segments, ≈50 nt long), C1 (green≈800 nt long) and J2 (violet, 7 segments, ≈50 nt), C2 (green≈700 nt long). The final transcript is a combination of either V-D1-J1-C1 or V-D2-J2-C2. Recombination signals (RSS) at the 3' end of V, both sides of D's and the 5' end of J, help ensure proper recombination. The C1 and C2 have a large region of identity, at the 5' end, allowing common primers for both versions. Each V comes with an associated leader sequence, alternate leader usage has been observed.

T cells are the central players in the immune system with effector functions to kill infected (or abnormal) cells, and regulate other T cells and B-cells. The TCR expressed by T cells allows them to recognize antigenic peptides presented to them by the major histocompatibility complexes (MHC) on the surfaces of cells (MHC class I on all cells, MHC class II on professional antigen presenting cells). All TCRs are heterodimers of receptor pairs: the majority of T cells, called α/β T cells, express the α-β receptor pair; the rest (<10%), called γ/δ T cells, express the γ-δ pair. All TCR genes undergo DNA rearrangements that allow the generation of a vast repertoire of potential amino acid sequences. Each TCR has multiple variable regions (V) and a number of 'joining' regions (J) before the constant (C) region (FIG. 1). Of the several complementarity determining regions (CDR), that determine the antigen-specificity of the TCR, the CDR3 (the junction of V-J) is the most important. For the β and γTCRs, one of a few 'diversity' (D) regions is interposed between the V and the J. The diversity in CDR3 is generated by the choice of V, D (for β, γ) and J, and by deletions and non-templated insertions.

The diversity of the TCR repertoire plays a critical role in the ability of the immune system to detect and respond to pathogens. Thus, understanding the normal distribution of the TCR repertoire and its deviations from normality under attack by pathogens provides a potential biomarker. Normally, T-cells will not recognize "self" proteins. In autoimmune disorders, this restraint is lost and certain self-antigens are targeted, leading to a range of disorders, from psoriasis to rheumatoid arthritis depending on the tissue under attack. The CD8+ T cells are cytotoxic Tcells that destroy cells whose class I MHC present peptides they recognize. Tregs, a subclass of CD4+ T cells that are CD25+, modulate the immune system by regulating other T cells to enable tolerance to self-antigens and reduce the possibility of autoimmune disorders. The remaining CD4+ T cells are the helper T cells (Th) that release cytokines to regulate B and T cells. T cells can also be classified as naïve (CD45RA+CCR7+) and memory (CD45RA-CCR7-) T cells that have been stimulated by antigens. Studying the TCR repertoire of each class of T cell separately might be key to uncovering markers for autoimmune disorders.

Monitoring the TCR repertoire has long been appreciated as a way to study the immune response, which can be performed through functional assays or using DNA, RNA or proteins. DNA-based measurements are confounded by the presence of a non-functional TCR copy in each cell. In contrast, RNA measurements directly assess the abundance of the functional copies. Non-sequencing methods are common, such as the CDR3-length distribution assay (CDR3-LD), which can detect the prevalence of oligoclonality by measuring the distribution of CDR3 lengths. Flow-cytometry has also been employed as a method for analyzing epitopes of TCRs but is limited by the availability of antibodies.

The TCR repertoire is best profiled by sequencing. Most approaches employ PCR with combinations of primers to amplify a broad swath of the TCR repertoire. However, differing PCR-primer efficiencies introduce substantial bias. This does not allow for the discovery of novel elements and variants. Lastly, multiplex PCR is difficult to implement. Another approach uses RACE-PCR to avoid using V-based primers, but this suffers from low efficiency (less than 1% of reads cover CDR3). It is widely acknowledged that all current methods of TCR repertoire analysis have significant limitations.

Advantageously, the methods provided herein overcome the limitations of current approaches. In some embodiments, universal primers are ligated to fragmented nucleic acids (e.g., mRNA or gDNA) and nested PCR is performed with 3' oligos from the constant C region and the universal 5' adapter as the second primer. This unbiased approach is highly efficient at sampling a recombination junction (e.g., a T cell receptor CDR3), due to the geometry depicted in FIG. 4 (>90% of reads are CDR3, for the TCR repertoires of α and β) and allows discovery of novel segments while reducing the sequencing cost substantially. In some embodiments, molecular identifiers are used on the adapters to track clonal amplification and improve accuracy.

In one aspect, the present disclosure provides methods for determining the diversity of genomic recombination events in an effective, accurate and rapid manner. This method includes a variety of steps for achieving the method and these are described in detail in the present disclosure. In some implementations, this method generates a T-cell receptor repertoire (TCRR).

GWAS studies of various autoimmune disorders have implicated variants in HLA haplotypes. In fact, stratifying patients by HLA types enabled identification of other genes in autoimmune celiac disease. Thus, identifying HLA haplotypes in conjunction with the TCR repertoire will be of great value in understanding the diversity of the TCR repertoire. The present disclosure provides methods that use targeted DNA capture to inexpensively sequence the HLA loci.

The present disclosure provides novel experimental techniques for TCR repertoire profiling, along with new analytical techniques and tools to analyze the resultant data. The methods allow exhaustive, unbiased annotation of TCR segments and proper characterization of the repertoire. In some embodiments, FACS is used to confirm the profiles determined by the methods provided herein.

The present disclosure also provides methods for simultaneously identifying HLA haplotypes and TCR repertoire profiles for sub classes of T cells and correlating them with each other. The correlations have not been systematically studied, especially in the context of autoimmune disorders. In some embodiments, the methods include stratifying the data according to HLA haplotypes. In some embodiments, the methods include characterizing a "normal" TCR repertoire. The normal repertoire can be used for association studies including autoimmune disorders, as well as for the study of the effectiveness of vaccine immunization, and for the study of response to infections.

The present disclosure also provides methods for using a TCR repertoire for the various sub classes of T cells, in the context of Graves' disease, to identify potential biomarkers, as well as therapeutic targets. By comparing the repertoire profiles from PBMCs and diseased tissues, biomarkers will be identified for less intrusive monitoring of the effect of treatments and potential targets may be identified for high-precision approaches. In this fashion, the methods provided herein are used as a model for other autoimmune disorders impacting clinical practice and standard of care.

In some embodiments, the methods provided herein are used to determine a B cell receptor repertoire. In some embodiments, a B cell receptor repertoire is used to study B cell infiltrants in other diseased tissues, such as cancer.

II. Select Definitions

The term "invention" or "present invention" as used herein is not meant to be limiting to any one specific embodiment of the invention but applies generally to any and all embodiments of the invention as described in the claims and specification.

As used herein, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure.

As described herein, in some embodiments T-cell receptor mRNAs and cDNAs includes "Variable" regions (V-regions), "Constant" regions (C-regions) and D-regions (CDR regions, including CDR3 regions). The common meaning of these terms would be understood by those of skill in the art and such a common understanding is contemplated by the presently described methods.

As used herein the term "single nucleotide polymorphism" ("SNP") and variants thereof refers to a site of one nucleotide that varies between alleles. A single nucleotide polymorphism (SNP) is a single base change or point mutation but also includes the so-called "indel" mutations (insertions or deletions of a nucleotide), resulting in genetic variation between individuals. SNPs, which make up about 90% of all human genetic variation, occur every 100 to 300 bases along the 3-billion-base human genome. SNPs can occur in coding or non-coding regions of the genome. A SNP in the coding region may or may not change the amino acid sequence of a protein product. A SNP in a non-coding region can alter promoters or processing sites and may affect gene transcription and/or processing. Knowledge of whether an individual has particular SNPs in a genomic region of interest may provide sufficient information to develop diagnostic, preventive and therapeutic applications for a variety of diseases.

The term "primer" and variants thereof refers to an oligonucleotide that acts as a point of initiation of DNA synthesis in a PCR reaction. A primer is usually about 15 to about 35 nucleotides in length and hybridizes to a region complementary to the target sequence; however primers can be longer as necessary.

As used herein, the term "Watson strand" is used to denote the sense strand, relative to a genomic locus of interest, of a double-stranded DNA molecule. For example, where a double-stranded DNA fragment includes a recombined junction followed by a constant region, the 5' end of the Watson strand is proximate to the recombined junction, relative to the constant region.

As used herein, the term "Crick strand" is used to denote the anti-sense strand, relative to a genomic locus of interest, of a double-stranded DNA molecule. For example, where a double-stranded DNA fragment includes a recombined junction followed by a constant region, the 5' end of the Crick strand is proximate to the constant region, relative to the recombined junction.

Unless otherwise indicated, all nucleic acid sequences are written in the standard 5'-3' format, including DNA, cDNA, and mRNA sequences as well as primer sequences.

Nucleic acid symbols:

| Symbol | Meaning |
|--------|---------|
| G | G (guanine) |
| A | A (adenine) |
| T | T (thymine) |
| C | C (cytosine) |
| R | G or A |
| Y | T or C |
| M | A or C |
| K | G or T |
| S | G or C |
| W | A or T |
| H | A or C or T |
| B | G or T or C |
| V | G or C or A |
| D | G or A or T |
| N | G or A or T or C |

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, various embodiments of methods and materials are specifically described herein.

III. Methods a. General Methodology

In one aspect, the disclosure provides a method for determining recombination diversity at a genomic locus of interest in a subject. The method includes isolating nucleic acids from a biological sample containing immune cells from the subject. The method further includes fragmenting the isolated nucleic acids, to form a plurality of fragmented nucleic acids. The plurality of fragmented nucleic acids contains a sub-plurality of at least 10 fragmented nucleic acids having a recombined junction and a constant region from the genomic locus of interest. The method includes ligating first adaptor nucleic acids to the ends of respective nucleic acids corresponding to the plurality of fragmented nucleic acids. The first adaptor nucleic acids include a first hybridization region having a first predefined hybridization sequence, thereby forming a plurality of ligated nucleic acid fragments.

The method further includes selectively amplifying respective ligated nucleic acid fragments, in the plurality of ligated nucleic acid fragments, containing a recombined junction at the genomic locus of interest using first and second primers. When the recombined junction is upstream of the constant region, the first primer hybridizes, at the first hybridization region, to the Crick strand of respective ligated nucleic acid fragments in the plurality of ligated nucleic acid fragments. When the recombined junction is upstream of the constant region, the second primer hybridizes, at a first site in the constant region downstream of the recombined junction at the genomic locus of interest, to the Watson strand of respective ligated nucleic acids containing the recombined junction at the genomic locus of interest in the plurality of ligated nucleic acid fragments. When the recombined junction is downstream of the constant region, the first primer hybridizes, at the first hybridization region, to the Watson strand of respective ligated nucleic acid fragments in the plurality of ligated nucleic acid fragments. When the recombined junction is downstream of the constant region, the second primer hybridizes, at a first site in the constant region downstream of the recombined junction at the genomic locus of interest, to the Crick strand of respective ligated nucleic acids containing the recombined junction at the genomic locus of interest in the plurality of ligated nucleic acid fragments. The selective amplification forms a plurality of amplified nucleic acid fragments having recombined junctions at the locus of interest. The method also includes sequencing amplified nucleic acid fragments in the plurality of amplified nucleic acid fragments.

In some embodiments, the nucleic acids are RNA and the plurality of fragmented nucleic acids are fragmented RNA. In some embodiments, the RNA is total RNA that is isolated from the sample. In some embodiments, the RNA is messenger RNA (mRNA) isolated from the sample. In some embodiments, where the isolated nucleic acids are RNA, the method includes preparing cDNA from the fragmented RNA, such that the first adaptor molecules are ligated to cDNA. In some embodiments, where the isolated nucleic acids are RNA, the first adaptor molecules are ligated to the fragmented RNA, and cDNA is prepared from the ligated RNA molecules.

In some embodiments, the nucleic acids are DNA, e.g., genomic DNA, and the fragmented nucleic acids are fragmented DNA, e.g., fragmented genomic DNA. In some embodiments, wherein the isolated nucleic acids are genomic DNA, the first adaptor molecules are ligated to fragments of genomic DNA.

In some embodiments, the sub-plurality of fragmented nucleic acids is at least 15 fragmented nucleic acids having a recombined junction and a constant region from the genomic locus of interest. In other embodiments, the sub-plurality of fragmented nucleic acids is at least 20, 25, 30, 40, 50, 60, 75, 100, 150, 200, 250, 300, 400, 500, 750, 1000, 1500, 2000, 3000, 4000, 5000, 7500, 10,000, 12,500, 15,000, 20,000, 25,000, 30,000, 40,000, 50,000, 75,000, 100,000, or more fragmented nucleic acids having a recombined junction and a constant region from the genomic locus of interest.

In some embodiments, the constant region in the sub-plurality of fragmented nucleic acids is at least 12 nucleotides long. In other embodiments, the constant region in the sub-plurality of fragmented nucleic acids is at least 13, 14, 15, 16, 17, 18, 19, 20, 21, 22, 23, 24, 25, 30, or more nucleotides long.

In some embodiments, the biological sample includes a population of T cells. In some embodiments, the biological sample is a blood sample, or fraction thereof. In some embodiments, peripheral blood mononuclear cells (PBMC) are enriched from a blood sample, prior to isolating the nucleic acids. In some embodiments, nucleic acids are isolated from a sample enriched for a particular type of T cell, e.g., CD4+ cells, CD8+ cells, CD2+/CD3+ cells, or Treg cells.

In some embodiments, the biological sample includes a population of B cells. In some embodiments, the biological sample is a blood sample, or fraction thereof. In some embodiments, peripheral blood mononuclear cells (PBMC) are enriched from a blood sample, prior to isolating the nucleic acids. In some embodiments, nucleic acids are isolated from a sample enriched for a particular type of B cell, e.g., plasmablast cells, plasma cells, memory B cells, follicular B cells, marginal zone B cells, B-1 cells, B-2 cells, or regulatory B cells (Bregs).

As used herein, reference to the length of a nucleic acid in nucleotides refers to either single-stranded polynucleotides or double stranded base pairs. Where the isolated nucleic acids are RNA, the fragments will be single stranded. Where the isolated nucleic acids are DNA, the fragments will be single stranded and the mean fragment length refers to base pairs (e.g., a length of 100 nucleotides refers to 100 base pairs).

In some embodiments, the nucleic acid fragments have a mean fragment length of at least 100 nucleotides, such that the recombination junctions (e.g., CDR sequence) would be expected to be included in the selectively amplified nucleic acid fragments. In some embodiments, the nucleic acid fragments have a mean fragment length of at least 150 nucleotides. In some embodiments, the nucleic acid fragments have a mean fragment length of at least 200 nucleotides. In some embodiments, the nucleic acid fragments have a mean fragment length of at least 250 nucleotides.

In some embodiments, the nucleic acid fragments have a mean fragment length of less than 1000 nucleotides, promoting efficient amplification of fragments containing a recombined junction (e.g., CDR sequence). In some embodiments, the nucleic acid fragments have a mean fragment length of less than 800 nucleotides. In some embodiments, the nucleic acid fragments have a mean fragment length of less than 600 nucleotides. In some embodiments, the nucleic acid fragments have a mean fragment length of less than 500 nucleotides. In some embodiments, the nucleic acid fragments have a mean fragment length of less than 400 nucleotides.

In some embodiments, the nucleic acid fragments have a mean fragment length of from 100 nucleotides to 1000 nucleotides. In some embodiments, the nucleic acid fragments have a mean fragment length of from 150 nucleotides to 600 nucleotides. In some embodiments, the nucleic acid fragments have a mean fragment length of from 200 nucleotides to 5000 nucleotides. In other embodiments, the nucleic acid fragments have a mean fragment length of from 100-800, 100-600, 100-500, 100-400, 150-1000, 150-800, 150-600, 150-500, 150-400, 200-1000, 200-800, 200-600, 200-500, 200-400, 250-1000, 250-800, 250-600, 250-500, or 250-400 nucleotides.

The adaptor nucleic acids are used as a hybridization platform for one of the amplification primers. In some embodiments, index sequences are incorporated into the adaptor nucleic acids. The index sequences allow particular recombination junctions to be followed, and quantitated, during amplification and sequencing. In some embodiments, different adaptor nucleic acids ligated to the isolated fragments have different index sequences. In some embodiments, at least two different index sequences are used. In other embodiments, at least 3, 4, 5, 6, 7, 8, 9, 10, 15, 20, 25, 30, 40, 45, 50, 55, 60, 70, 80, 90, 100, or more index sequences are used. Generally, the more index sequences used in the method, the higher resolution the data will be after sequencing. However, even using just two index sequences will provide data about the clonality of individual recombination junctions and use of particular variable, diversity, and joining regions.

In some embodiments, the adaptor nucleic acids include one or more modified and/or non-conventional nucleic acids. In some embodiments, the adaptor nucleic acids consist of modified and/or non-conventional nucleic acids. In some embodiments, the adaptor nucleic acids include one or more modified nucleic acid residues. For example, in some embodiments, the non-conventional nucleic acids include but are not limited to biotinylated nucleic acids, peptide nucleic acids (PNAs), locked nucleic acids (LNAs), and/or phosphorothioated nucleic acids, as well as any other non-conventional nucleic acids known to those of skill in the art.

In some embodiments, the first adaptor nucleic acids are a plurality of first adaptor nucleic acids. Each respective first adaptor nucleic acid in the plurality of first adaptor nucleic acids includes a first portion and a second portion, the second portion positioned at the 3' end of the first portion on the Watson strand of the adaptor nucleic acid. The first portion of each respective first adaptor nucleic acid comprises the first hybridization region includes the first predefined hybridization sequence. The second portion of each respective first adaptor nucleic acid includes an indexing region having one of a plurality of indexing sequences. The plurality of first adaptor molecules includes at least two respective first adaptor molecules with different indexing sequences. In some embodiments, the plurality of first adaptor molecules includes at least sixteen respective first adaptor molecules with different indexing sequences. In some embodiments, the plurality of first adaptor molecules includes at least sixty-four respective first adaptor molecules with different indexing sequences.

In some embodiments, the plurality of indexing sequences are random sequences. In some embodiments, the plurality of indexing sequences are predefined sequences. In some embodiments, the indexing sequence is at least 2 nucleotides (e.g., base pairs) long. In some embodiments, the indexing sequence is at least 3 nucleotides long. In some embodiments, the indexing sequence is at least 4 nucleotides. In some embodiments, the indexing sequence is at least 5, 6, 7, 8, 9, 10, or more nucleotides.

In some embodiments, the method includes introducing a bar code into the amplified nucleic acids. In some embodiments, the bar codes are used to identify the source of the nucleic acids, e.g., to differentiate between nucleic acids amplified from a first sample (e.g., from a first subject) from nucleic acids amplified from a second sample (e.g., from a second subject). In this fashion, nucleic acids amplified from several samples can be sequenced in a single sequencing reaction, the resulting sequences can be uniquely assigned to one of the several samples.

In some embodiments, the selective amplification of the ligated nucleic acid fragments is performed via a single PCR amplification reaction using said first and second primers.

In some embodiments, where a single PCR amplification reaction is used, the second primer includes a first portion, a second portion positioned at the 3' end of the first portion, and a third portion positioned at the 3' end of the second portion. The first portion of the second primer includes a second hybridization region having a second predefined hybridization sequence. The second portion of the second primer includes a bar code region having a bar code sequence. The third sequence comprises a hybridization region having a sequence that hybridizes, at the first site in the constant region downstream of the recombined junction at the genomic locus of interest, to the Watson strand of respective ligated nucleic acids containing the recombined junction at the genomic locus of interest in the plurality of ligated nucleic acid fragments.

In some embodiments, the selective amplification of the ligated nucleic acid fragments is performed via a series of nested PCR amplification reactions, including a first PCR amplification reaction using first and second primers, and a second PCR amplification reaction using third and fourth primers. The third primer hybridizes, at the first hybridization region, to the Crick strand of amplified nucleic acid fragments. The fourth primer hybridizes, at a second site in the constant region downstream of the recombined junction at the genomic locus of interest, to the Watson strand of amplified nucleic acid fragments. In some embodiments, the second site is located 5' of the first site on the Watson strand of the amplified nucleic acid fragments. In some embodiments, the third primer, used in the second PCR reaction, hybridizes to the same site as the first primer, used in the first PCR reaction.

In some embodiments, the nested PCR method includes at least three PCR amplification reactions. In some embodiments, the nested PCR method includes at least four PCR amplification reactions. In some embodiments, the nested PCR method includes at least 5, 6, 7, or more PCR amplification reactions.

In some embodiments, where the selective amplification is performed by nested PCR, the primer hybridizing to the constant region in the final PCR reaction (e.g., the fourth primer), includes a first portion, a second portion positioned at the 3' end of the first portion, and a third portion positioned at the 3' end of the second portion. The first portion of the fourth primer includes a second hybridization region having a second predefined hybridization sequence. The second portion includes a bar code region having a bar code sequence. The third sequence includes a hybridization region having a sequence that hybridizes, at the first site in the constant region downstream of the recombined junction at the genomic locus of interest, to the Watson strand of respective ligated nucleic acids containing the recombined junction at the genomic locus of interest in the plurality of ligated nucleic acid fragments.

In some embodiments, where the genomic locus of interest is a human T cell receptor α-locus, the second primer includes the sequence CACTGGATTTAGAGTCTCTCAGC (SEQ ID NO:6).

In some embodiments, where the genomic locus of interest is a human T cell receptor α-locus, the primer hybridizing to the constant region in the final PCR reaction (e.g., the fourth primer) includes the sequence GCTGGTACACGGCAGGGTCA (SEQ ID NO:16).

In some embodiments, where the genomic locus of interest is a human T cell receptor β-locus, the second primer includes the sequence TGCTTCTGATGGCTCAAACA (SEQ ID NO:17).

In some embodiments, where the genomic locus of interest is a human T cell receptor β-locus, the primer hybridizing to the constant region in the final PCR reaction (e.g., the fourth primer) includes the sequence CAGCGACCTCGGGTGGGAAC (SEQ ID NO:18).

In some embodiments, the primers include one or more modified and/or non-conventional nucleic acids. In some embodiments, the primers consist of modified and/or non-conventional nucleic acids. In some embodiments, the primers include one or more modified nucleic acid residues. For example, in some embodiments, the non-conventional nucleic acids include but are not limited to biotinylated nucleic acids, peptide nucleic acids (PNAs), locked nucleic acids (LNAs), and/or phosphorothioated nucleic acids, as well as any other non-conventional nucleic acids known to those of skill in the art.

In some embodiments, sequencing the amplified nucleic acid fragments includes mixing amplified nucleic acid fragments from a plurality of samples (e.g., from different subjects), where the amplified nucleic acid fragments from each respective sample have a different bar code sequence.

In some embodiments, the method also includes annotating the sequence of the recombined junction, at the genomic locus of interest, in respective amplified nucleic acid fragments sequenced. In some embodiments, the method further includes assembling a recombination profile of the subject, including the annotated sequences of recombined junctions at the genomic locus of interest.

In some embodiments, a recombination profile is compared to a reference profile. In some embodiments, the reference profile is characteristic of a particular medical disorder. In one embodiment, the disorder is Graves' disease.

Graves' disease (GD) is characterized by hyperthyroid activity, caused by the immune system making antibodies mimicking the thyroid-stimulating hormone (TSH), which is usually made by the pituitary gland, causing the thyroid to synthesize and secrete thyroid hormone. The autoimmune response to TSHR, which is over expressed, characterizes GD. Detecting this response through TCR repertoire profiling will help develop biomarkers for studying the progress of the disease as well as the effectiveness of treatments. The relatively high frequency of GD (0.4% of the population) makes it a good model for autoimmunity.

In some embodiments, the method also includes determining a relative clonal number of a respective recombined junction at the genomic locus of interest by determining the number of times the sequence of the recombined junction is associated with a respective indexing sequence, in the plurality of indexing sequences, from a first adaptor nucleic acid.

In some embodiments, the disclosed methods are used to establish a "normal" range of variability in humans across geographic origins in various sub classes of T cells (e.g., memory T cells, CD8+ and CD4+ including Tregs) and/or B cells.

In some embodiments, the methods provided herein include profiling HLA haplotypes, using targeted DNA capture, to measure associations between HLA haplotypes and the TCR repertoire. Stratifying the repertoire data on the basis of the HLA sub types will help interpret and understand data from our TCR-based, epidemiological studies.

In some embodiments, the methods provided herein are used to determine B cell repertoire measurements. In one embodiment, the methods are used to study infiltrants in thyroid samples.

In some embodiments, the methods are used to develop biomarkers, e.g., from PBMCs, to monitor the progression of disease and response to treatment through changes in the TCR repertoire.

In some embodiments, the methods described herein are used to determine a B cell receptor repertoire. In some embodiments, patients are stratified by HLA haplotypes to help organize the repertoire data from both sorted T cells from PBMCs and TCR and/or BCR repertoires from thyroid tissues. In some embodiments, the TCR repertoires from subjects having a medical disorder (e.g., Graves' disease) are compared to a "normal" repertoires, in conjunctions with the HLA data, to organize the information and identify potential biomarkers. Identification of sub classes of T cells that are most impacted by GD helps determine the mechanisms of the disease and enables novel therapeutic approaches.

In some embodiments, the methods described provide for generating a T-cell receptor repertoire (TCRR) from a T-cell population, the method comprising: a) isolating mRNA from said T-cell population; b) fragmenting said mRNA to obtain a collection of mRNA fragments having a mean fragment length that is less than about 600 bp; c) preparing cDNA from the collection of fragments of step b); d) ligating a first adapter module and second adapter module to the cDNA from step c); where the second adapter module is the same or different than the first adapter module, and where the first adapter module ligates to a first end of the cDNA and the second adapter module ligates to a second end of the cDNA; e) performing a first round of PCR amplification using a first primer and a second primer, where the first primer binds to a first region and the second primer binds to a second region in the first round of PCR amplification (e.g., during one or more instances during the first round of PCR amplification), where the first region is at least partially in the first adapter and the second region is in the C-region, thereby obtaining first amplified products; and f) performing a second round of PCR amplification on the first amplified products using a third primer and a fourth primer thereby deriving second amplified products, where the third primer binds to a third region and the fourth primer binds to a fourth region in the second round of PCR amplification, where the third region is at least partially in the first adapter and the fourth region is in the C-region, where a nucleotide distance between the first and the second region is greater than a nucleotide distance between the third region and the fourth region and where the fourth region is located at least partially between the first and second regions. It will be appreciated that the first round of PCR amplification refers to a plurality of cycles of amplification using the first and second primers and the second round of PCR amplification refers to a plurality of cycles of amplification using the third and fourth primers.

b. Data Analysis

In some embodiments, sequencing data from a recombination repertoire (e.g., a TCR repertoire) is used to characterize the vast diversity with a few parameters, enabling comparison of datasets. In one embodiment, the data can be treated as vectors whose components are various recombined segments (e.g., the V's, D's, J's and their combinations). Two approaches can be used to study this data: by comparing models of the data or by clustering the data.

In some embodiments, the data generated from sequencing amplified fragments is analyzed by clustering. In one embodiment, the distribution of recombined regions (e.g., V's, J's, and V-J combinations) are used as vectors, and the Spearman-rank correlation can be used to determine a distance between the vectors, which can then be used to cluster samples. In some embodiments, this shows the MHC's influence on the TCR repertoire.

In some embodiments, differences in entropy are used to measure differences between samples via information theoretic measures. In some embodiments, for V-J combinations or other pairwise distributions, the Kullback-Leibler divergence or mutual information, which is an information theoretic measure, can also be used to measure distances.

In some embodiments, CDR3 trees can be constructed and compared to determine if the branching shows substantial similarity. In the case of matrix data, such as the VJ combinations, a chi-square measure can test if the V-J combinations are independent of each other.

In some embodiments, the data generated from sequencing amplified fragments is analyzed by modeling. The goal is to characterize the data with a few parameters in order to compare samples, as well as determine the appropriate depth of sequencing for the particular sample. In ecology, there is a long tradition, starting with Fisher, of estimating the number of species in an ecosystem, based on the sampling of a few individual members of the flora or fauna. This approach has been extended and applied to the analysis of texts, especially to identify authors of unattributed prose and poems by modeling the distribution of words using a negative binomial distribution. The negative binomial distribution is $P(y,r,p)=C_y^{r+y-1} p^r (1-p)^y$ characterized by the three parameters, y, r and p, where y is the number of failures before r successes occur and p is the chance of success in a single trial. This is also called the Polya distribution when the parameters have real values instead of integers and is a contagious distribution since the occurrence of a word disposes it to occur more often causing "clumping" in the data. Under different limits of y, r and p this distribution approaches other distributions such as the Geometric (r=1) or Poisson (y+r→∞, p→0). By fitting the negative binomial distribution to TCR repertoire data, the nature of the tails of the distribution of a recombination repertoire (e.g., a TCR repertoire) can be determined. The effect of perturbations, including infections and autoimmunity, on the tail is of great interest.

A second approach is to use information theory, including measures such as entropy and mutual information. This approach has also been used in the analysis of texts, such as the zipfian analysis of the power laws exhibited by word frequencies or in the analysis of a variety of economic, physical and social phenomena. Entropy characterizes the distribution of recombined sequences (e.g., VJ (or VDJ)) using a single number, $E=-\Sigma_i p_i \log p_i$ where $p_i$ is the fraction of the population in species "i". A larger number of species results in a bigger entropy, as does a less "peaked" distribution. Low entropy implies low diversity and dominance by a few species.

c. T-Cell Receptor Repertoire (TCRR)

In some embodiments, the present disclosure provides a method for generating a T-cell receptor repertoire (TCRR) from a T-cell population, the method comprising: a) isolating mRNA from the T-cell population; b) fragmenting the mRNA to obtain a collection of mRNA fragments having a mean fragment length that is less than about 600 bp; c) preparing cDNA from the collection of fragments; d) ligating at least a first adapter module to the cDNA; wherein the first adapter module ligates to a first end of the cDNA; e) performing a first round of PCR amplification using a first primer and a second primer, wherein the first primer binds to a first region and the second primer binds to a second region in the first round of PCR amplification, wherein the first region is at least partially in the first adapter and the second region is in the C-region, thereby obtaining a plurality of first amplified products; and f) performing a second round of PCR amplification on the plurality of first amplified products using a third primer and a fourth primer thereby deriving a plurality of second amplified products, wherein the third primer binds to a third region and the fourth primer binds to a fourth region in the second round of PCR amplification, the third region is at least partially in the first adapter and the fourth region is in the C-region, an average nucleotide distance between the first and the second region across the plurality of first amplified products is greater than an average nucleotide distance between the third region and the fourth region across the plurality of second amplified products, and the fourth region is located at least partially between the first and second regions.

Here it will be understood that the term "across the plurality of first amplified products" means to take the nucleotide distance between the first region and the second region in each first amplified product in the plurality of first amplified products and to average them together. In some embodiments, this distance varies among the first amplified products. In some embodiments, this distance does not vary among the first amplified products.

Here it will be further understood that the term "across the plurality of second amplified products" means to take the nucleotide distance between the third region and the fourth region in each second amplified product in the plurality of second amplified products and to average them together.

In some embodiments, this distance varies among the second amplified products. In some embodiments, this distance does not vary among the second amplified products. In embodiments where the distances do not vary, it is not necessary to take the average.

In some embodiments, the mRNA is isolated from total T-cell RNA.

In some embodiments, the fragmenting occurs via a mechanical or a chemical process. In some embodiments, the fragmenting occurs via mechanical shearing.

In some embodiments, the collection of mRNA fragments have a mean fragment length that is less than about 500 bp or less than about 400 bp in length, or less than about 300 bp in length. In some embodiments, the collection of mRNA fragments have a mean fragment length that is less than about 400 bp in length.

In some embodiments, the cDNA is prepared by the preparing in c) using random primers.

In some embodiments, the (i) the ligating in d) results in ligation of a second adapter module to the cDNA, (ii) the second adapter module is the same or different than the first adapter module, and (iii) the second adapter module ligates to a second end of the cDNA.

In some embodiments, the ligating the first adapter and/or the second adapter modules in d) include end repair, A-base addition and/or adapter sequence ligation.

In some embodiments, the TCRR is for an alpha T-cell receptor repertoire.

In some embodiments, the alpha T-cell receptor repertoire is a mouse TCRR and wherein the first and second primer sequences respectively comprise the sequences:

(SEQ ID NO: 1)
AATGATACGGCGACCACCGAGATCTACACTCTTTCCCTACACGACGCTCT

TCCGATC*T
and (SEQ ID NO: 2.)
TCCTGAGACCGAGGATCTTTTA.

In some embodiments, the alpha T-cell receptor repertoire is a human TCRR and wherein the first and second primer sequences respectively comprise the sequences:

(SEQ ID NO: 1)
or AATGATACGGCGACCACCGAGATCTACACTCTTTCCCTACACGACGCT

CTTCCGATC*T
and (SEQ ID NO: 6)
CACTGGATTTAGAGTCTCTCAGC.

In some embodiments, the alpha T-cell receptor repertoire is a mouse TCRR and wherein the third and fourth primer sequences respectively comprise the sequences:

(SEQ ID NO: 1)
AATGATACGGCGACCACCGAGATCTACACTCTTTCCCTACACGACGCTCT

TCCGATC*T
and (SEQ ID NO: 3)
CAAGCAGAAGACGGCATACGAGAT[CGTGAT]GGTACACAGCAGGTT

CTGGGTTCTGGATGT.

In some embodiments, the alpha T-cell receptor repertoire is a human TCRR and wherein the third and fourth primer sequences respectively comprise the sequences:

(SEQ ID NO: 1)
AATGATACGGCGACCACCGAGATCTACACTCTTTCCCTACACGACGCTCT

TCCGATC*T
and (SEQ ID NO: 7)
CAAGCAGAAGACGGCATACGAGATTGGTCAGTGACTGGAGTTCAGACGTG

TGCTCTTCCGATCTNNNGCTGGTACACGGCAGGGTCA.

In some embodiments, the TCRR is for a beta T-cell receptor repertoire.

In some embodiments, the beta T-cell receptor repertoire is a mouse TCRR and wherein the first and second primer sequences respectively comprise the sequences:

(SEQ ID NO: 1)
AATGATACGGCGACCACCGAGATCTACACTCTTTCCCTACACGACGCTC

TTCCGATC*T
and (SEQ ID NO: 4)
AAGGAGACCTTGGGTGGAGTCA.

In some embodiments, the beta T-cell receptor repertoire is a human TCRR and wherein the first and second primer sequences respectively comprise the sequences:

(SEQ ID NO: 1)
AATGATACGGCGACCACCGAGATCTACACTCTTTCCCTACACGACGCTC

TTCCGATC*T
and (SEQ ID NO: 8)
TGCTTCTGATGGCTCAAACA.

In some embodiments, the beta T-cell receptor repertoire is a mouse TCRR and wherein the third and fourth primer sequences respectively comprise the sequences:

(SEQ ID NO: 1)
AATGATACGGCGACCACCGAGATCTACACTCTTTCCCTACACGACGCTCT

TCCGATC*T
and (SEQ ID NO: 5)
CAAGCAGAAGACGGCATACGAGAT[TGGTCA]CCTTGGGTGGAGTCACAT

TTCTCAGATCCT.

In some embodiments, the beta T-cell receptor repertoire is a human TCRR and wherein the third and fourth primer sequences respectively comprise the sequences:

(SEQ ID NO: 1)
AATGATACGGCGACCACCGAGATCTACACTCTTTCCCTACACGACGCT

CTTCCGATC*T
and (SEQ ID NO: 9)
CAAGCAGAAGACGGCATACGAGATCACTGTGTGACTGGAGTTCAGACG

TGTGCTCTTCCGATCTNNNNNNCAGCGACCTCGGGTGGGAAC.

In some embodiments, the first primer and the third primer comprise the same or different sequences. In some embodiments, the first primer and the third primer consist of the same sequence.

In some embodiments, the fourth primer exhibits increased specificity for the fourth region as compared to the specificity of the second primer for the second region. In some embodiments, the fourth primer exhibits a higher Tm for the fourth region than the second primer does for the second region. In some embodiments, the fourth primer is longer than the second primer.

In some embodiments, the fourth primer comprises a sequence corresponding to the second adapter sequence in d).

In some embodiments, the fourth primer comprises a barcode.

In some embodiments, the fourth primer comprises a sequence corresponding to the second adapter sequence in d) and a barcode.

In some embodiments, the second region and the fourth region do not overlap. In some embodiments, the second region and the fourth region partially overlap. In some embodiments, the second primer and the fourth primer bind at regions that do not overlap. In some embodiments, the second primer and the fourth primer bind at regions that partially overlap.

In some embodiments, the second primer and the fourth primer are configured to bind to regions which do not contain common SNPs.

In some embodiments, the first adapter is about 30 nt, about 40 nt, about 50 nt, about 60 nt, about 70 nt, or about 80 nt in length. In some embodiments, the first adapter is about 60 nt in length.

In some embodiments, the second adapter is about 30 nt, about 40 nt, about 50 nt, about 60 nt, about 70 nt, or about 80 nt in length. In some embodiments, the second adapter is about 60 nt in length.

In some embodiments, the second amplified products each comprise a CDR3 region, a V-region or subportion of a V-region, and/or a J-region or subportion of a J-region.

In some embodiments, the T-cell mRNA is isolated from T-cells from a biological sample from a subject. In some embodiments, the subject exhibits a disease or disease symptoms. In some embodiments, the biological sample is a body fluid sample and/or tissue sample. In some embodiments, the biological sample is selected from the group consisting of blood, plasma, serum, bone marrow, semen, vaginal secretions, urine, amniotic fluid, cerebrospinal fluid, synovial fluid and biopsy tissue samples, including from infection and/or tumor locations.

In some embodiments, the method further comprises g) performing an analysis on the second amplified products obtained from f).

In some embodiments, the analysis comprises sequence analysis, SNP analysis, hybridization analysis and/or microarray analysis.

IV. Methods of Fragmenting Nucleic Acids

A variety of methods for fragmenting nucleic acids are known in the art and any such methods can be employed with the present invention, so long as such methods maintain the structural integrity of the nucleic acid being fragmented. Fragmentation methods of the present disclosure include mechanical and/or chemical processes.

Mechanical fragmentation can occur via variety of methods, including but not limited to acoustic shearing (delivery of high-frequency acoustic energy waves to the sample), sonication (hydrodynamic shearing method), nebulization (forcing sample through a small hole in a nebulizer unit, which results in the formation of a fine mist and sample shearing), point-sink shearing (hydrodynamic shearing using a syringe pump), needle-shearing (passing sample through small gauge needle) and French pressure cells (pass sample through a narrow valve under high pressure to create high shearing forces). In some embodiments, the fragment occurs via a mechanical shearing process.

Chemical shearing can occur via enzymatic or other chemical digestion. Such methods include restriction digestion with any of a large number of commercially available enzymes. In some embodiments, the fragment occurs via a chemical shearing process.

In some embodiments, the fragmentation results in a collection of nucleic acid (e.g., mRNA or genomic DNA) fragments that have a mean fragment length that is less than about 600 bp (e.g., nt or bp), less than about 500 bp, less than about 400 bp, less than about 300 bp. In some embodiments, the fragmentation results in a collection of mRNA fragments that have a mean fragment length that is less than about 400 bp.

In some embodiments, about 20%, about 30%, about 40%, about 50%, about 60%, about 70%, about 80%, about 90% and/or about 99% or more of the fragments exhibit the mean fragment length. In some embodiments, about 20% to about 100%, about 30% to about 90%, about 40% to about 90%, about 40% to about 80%, about 30% to about 70%, about 40% to about 70%, about 40% to about 60%, about 40% to about 50% or more exhibit the mean fragment length. In some embodiments, greater than about 20%, greater than about 30%, greater than about 40%, greater than about 50%, greater than about 60%, greater than about 70%, greater than about 80%, greater than about 90% and/or greater than about 99% of the fragments exhibit the mean fragment length.

V. Adapter Modules

The methods of the present disclosure include ligating at least a first adapter module to said nucleic acid fragments (e.g., genomic DNA fragments or cDNA fragments). The first adapter module (e.g., nucleic acid) ligates to a first end of the nucleic acid fragments.

In some embodiments, the ligation also results in ligation of a second adapter module to the nucleic acid fragments. In some embodiments, the second adapter module is the same as the first adaptor molecule. In some embodiments, the second adaptor molecule is different than the first adapter module. The second adapter module ligates to a second end of the fragmented nucleic acids.

In some embodiments, ligating the first adapter and/or said second adapter includes end repair, A-base addition, and/or adapter sequence ligation.

These first and second adapter modules of the present invention can include any adapter sequence deemed useful by one of skill in the art for the present methods. In some embodiments, the adapter module comprises an adapter sequence as well as additional sequences, such as a barcode or other tag, as described herein. In some embodiments, the adapter module consists of only the adapter sequence.

Adapter modules and/or adapter sequences of the invention can include any primary sequence of nucleic acids and can range from 20 to 100 nt in length. In some embodiments the adapter module and/or adapter sequence is about 20 nt, about 30 nt, about 40 nt, about 50 nt, about 60 nt, about 70 nt, about 80 nt, about 90 nt or about 100 nt in length. In some embodiments the adapter module and/or adapter sequence is at least about 20 nt, at least about 30 nt, at least about 40 nt, at least about 50 nt, at least about 60 nt, at least about 70 nt, at least about 80 nt, at least about 90 nt, or at least about 100 nt in length. In some embodiments, the adapter module and/or adapter sequence is at least about 60 nt in length.

In some embodiments, the adapter module includes a barcode for identification of a sequence. In some embodiments, the barcode is separate from the adapter sequence.

VI. Methods for Ligating Adapter Modules

Methods for ligating adapter modules can include end repair, A-base addition and/or adapter sequence ligation.

In some embodiments, DNA fragments are modified by a polymerase and a polynucleotide kinase in a first reaction mixture order to obtain end repair of the DNA fragments. The end repaired DNA fragments are then contacted with a (3'-*5' exo) polymerase in a second reaction mixture sufficient for A-base addition (i.e., A-tailing) of the end-repaired DNA fragments. DNA adapter modules are then ligated to the A-base added DNA in a third reaction mixture that comprises a nucleic acid ligase.

In some embodiments, the ligation methods include contacting DNA fragments with T4 DNA polymerase and T4 polynucleotide kinase in a first reaction mixture sufficient for end repair of the DNA fragments; then contacting the end repaired DNA fragments with Klenow (3'→5' exo-) in a second reaction mixture sufficient for A-tailing the end-repaired DNA fragments; followed by ligating DNA adapter modules to the A-tailed DNA in a third reaction mixture comprising T4 DNA ligase.

For example, the first reaction mixture may comprise T4 DNA polymerase, T4 DNA polynucleotide kinase, deoxynucleotide triphosphates, a source of magnesium, and a buffer. In some embodiments, the first reaction mixture includes from 0.5 to 20 Units of T4 DNA polymerase and 0.5 to 50 Units of T4 polynucleotide kinase. In some embodiments, the first reaction mixture contains from 1 to 50 Units of T4 DNA polymerase and T4 polynucleotide kinase. In some embodiments, the dNTPS are at a concentration of from about 0.1 mM to about 5 ηtM, such as about 0.2 mM to 1.0 mM, or about 0.4 mM. The source of magnesium can be $MgCl_2$ at from about 2 mM to about 20 mM, such as about 10 mM. Any appropriate buffering agent can be included, such as TRIS-HCl in some embodiments, and should provide a pH of about 7.0 to 8.0, such as about 7.5. Other reaction components such as ATP (e.g., 0.5 to 5 mM), DTT (about 1 mM), KCl (about 1 to 20 mM), and detergents (e.g., Triton X-100) may also be included.

DNA adapter ligation is typically performed using DNA ligase. In some embodiments, the second reaction mixture comprises T4 DNA ligase, a source of magnesium, ATP, and a buffer. In some embodiments, the T4 DNA ligase is present at from 1 Unit to about 3,000 Units. In some embodiments, the source of magnesium (e.g., $MgCl_2$) is present at from about 2 mM to about 20 mM (e.g., 10 mM). In some embodiments, ATP is present at from about 0.1 to about 5 mM (e.g., about 5 mM). In some embodiments, other components such as DTT (e.g., about 1 mM), polyethylene glycol, and a suitable buffer (e.g., TRIS-HCl and pH of from about 7.0 to about 8.0, such as about 7.6) are also included.

In some embodiments, the ligase comprises a mesophilic or thermostable ligase enzyme. In some embodiments, the ligase comprises an E. coli DNA ligase, Taq DNA ligase, 9° N™ DNA ligase, or T4 DNA ligase. In some embodiments, the ligase comprises a small footprint ligase enzyme.

In some embodiments, a suitable nucleic acid ligation condition includes well known parameters, such as: time, temperature, pH, buffers, reagents, cations, salts, co-factors, nucleotides, nucleic acids, and enzymes. In some embodiments, a nucleic acid ligation reaction includes ATP and/or NAD. In some embodiments, a reagent or buffer includes a source of ions, such as KCl, K-acetate, $NH_4$-acetate, K-glutamate, $NH_4Cl$, or ammonium sulfate. In some embodiments, a reagent or buffer includes a source of ions, such as magnesium, manganese, cobalt, or calcium. In some embodiments, a reagent or buffer includes acetate or chloride. In some embodiments, a buffer can include Tris, Tricine, HEPES, MOPS, ACES, MES, or inorganic buffers such as phosphate or acetate-based buffers which can provide a pH range of about 4-12. In some embodiments, a buffer includes chelating agents such as EDTA or EGTA. In some embodiments, a buffer includes dithiothreitol (DTT), glycerol, spermidine, BSA (bovine serum albumin) and/or Tween.

In some embodiments, a suitable condition includes conducting a nucleic acid ligation reaction for a time, such as about 1-10 seconds, or about 10-60 seconds, or about 1-30 minutes, or about 30-60 minutes, or about 1-3 hours, or about 3-6 hours, or about 6-12 hours, or about 12-24 hours, or longer. In some embodiments, the ligation reaction proceeds for 5 minutes, 10 minutes or 15 minutes. In some embodiments, the ligation reaction proceeds for 10 minutes.

In some embodiments, a suitable condition includes conducting a nucleic acid ligation reaction under thermo-cycle conditions, or isothermal temperature conditions, or a combination of both. In some embodiments, a suitable condition includes conducting a nucleic acid ligation reaction at a temperature range of about 0° C. to 10° C., or about 10° C. to 20° C., or about 20° C. to 30° C., or about 30° C. to 40° C., or about 40° C. to 50° C., or about 50° C. to 60° C., or about 60° C. to 70° C., or about 70° C. to 80° C., or about 80° C. to 90° C., or about 90° C. to 99° C., or a higher temperature range. In some embodiments, the ligation reaction proceeds at about 30° C.

In some embodiments, a suitable condition includes conducting a nucleic acid ligation reaction at a pH range of about 5 to 9, or a pH range of about 6 to 8, or a pH range of about 7 to 7.5.

In some embodiments, a suitable condition includes conducting a nucleic acid ligation reaction in a tube, well or flowcell. In some embodiments, the well can be a part of an array or a multi-well plate or a multi-well chip.

Methods for ligating nucleic acids together are well established and any methods for ligating the adapter module to the cDNA can be employed with the described methods. Ligation methods have also been described in a variety of references, including for example, Molecular Cloning (three volume set, Cold Spring Harbor Laboratory Press, 2012) and Current Protocols (Genetics and Genomics; Molecular Biology; 2003-2013), incorporated herein by reference for all purposes.

VII. Amplification Methods

Polymerase chain reaction (PCR) can be used to amplify the relevant regions from a collection of cells in order to determine the diversity of a recombination junction (e.g., a T-cell receptor repertoire (TCRR) or B cell receptor repertoire) at a genomic locus of interest.

In some embodiments, two rounds of PCR are performed. In some embodiments, the methods of the present disclosure include e) performing a first round of PCR amplification using a first primer and a second primer, wherein said first primer binds to a first region and said second primer binds to a second region in said first round of PCR amplification, wherein the first region is at least partially in said first adapter and said second region is in the C-region, thereby obtaining a plurality of first amplified products; and f) performing a second round of PCR amplification on said plurality of first amplified products using a third primer and a fourth primer thereby deriving a plurality of second amplified products, wherein said third primer binds to a third region and said fourth primer binds to a fourth region in said second round of PCR amplification, wherein said third region is at least partially in the first adapter and said fourth region is in the C-region, wherein a nucleotide distance between the first and the second region is greater than a nucleotide distance between the third region and the fourth region and wherein the fourth region is located at least partially between the first and second regions.

In some embodiments, the first and/or second region to be amplified includes the full clonal sequence or a subset of the clonal sequence, including the V-D junction and/or the D-J junction of an mRNA expressed in a T-cell. In some embodiments, the first and/or second region to be amplified includes the full variable region of an T-cell receptor mRNA, the antigen recognition region, or a CDR, e.g., complementarity determining region 3 (CDR3). In embodiments, the first and/or second region to be amplified includes the as subportion of variable region of an T-cell receptor mRNA, the antigen recognition region, or a CDR, e.g., complementarity determining region 3 (CDR3). In some embodiments, the first and/or second region to be amplified includes about 30%, about 40%, about 50%, about 60%, about 70%, about 80%, about 90%, about 95%, or about 99% or 100% of the variable region of an T-cell receptor.

Other methods of amplifying the nucleic acids that can be used in the methods of the invention include, for example, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification.

Polymerases that can be used for amplification in the methods of the provided invention include, for example, Taq polymerase, AccuPrime polymerase, or Pfu. The choice of polymerase to be used in the methods described herein can be based on whether fidelity or efficiency is preferred. In some embodiments, a high fidelity polymerase is employed.

In some embodiments, the T-cell receptor cDNA sequence is amplified in a first and a second amplification step. Each of these two amplification steps include at least one different or unique primer. In some embodiments, the primers employed can introduce one or more sequences not originally present in the immune gene sequence. For example, the amplification procedure can add one or more additional sequences, tags, to the 5' and/or 3' end of amplified T-cell receptor cDNA sequence. In some embodiments a tag includes a sequence that facilitates subsequent sequencing of the amplified cDNA. In some embodiments, a tag includes a sequence that facilitates binding the amplified sequence to a solid support. In some embodiments, a tag includes a bar-code or label to facilitate identification of the amplified T-cell receptor cDNA sequence. In some embodiments, the tag is adjacent to the second adapter module.

In some embodiments, the methods include performing a first round of PCR amplification using a first primer and a second primer in order to derive a plurality of first amplified products. In some embodiments, the first primer binds to a first region and the second primer binds to a second region during the first round of PCR amplification. In some embodiments, the first region is at least partially in said first adapter and said second region is in the C-region. In some embodiments, the second region includes other sequences in addition to those in the C-region. In some embodiments, the portion of the second region contained in the C-region provides for additional specify and a reduction in bias during amplification.

In some embodiments, the methods include performing a second round of PCR amplification on the plurality of first amplified products using a third primer and a fourth primer in order to derive a plurality of second amplified products. In some embodiments, the third primer binds to a third region and the fourth primer binds to a fourth region in the second round of PCR amplification. In some embodiments, the third region is at least partially in the first adapter module and the fourth region is in the C-region. In some embodiments, the nucleotide distance between the first and the second region is greater than the nucleotide distance between the third region and the fourth region. In some embodiments, the fourth region is located at least partially between the first and second regions. In some embodiments, the third region is at least partially in said first adapter and said fourth region is in the C-region. In some embodiments, the second region is shorter in nucleotide length than the fourth region. In some embodiments, the first region and the third region are the same number of nucleotides in length. In some embodiments, the first region and the third region are a different number of nucleotides in length.

In some embodiments, the first primer binds to a region in the first adapter module. In some embodiments, the first primer and said third primer are the same or different sequences. In some embodiments, the said first primer and said third primer include or consist of the same sequence.

In some embodiments, the fourth primer exhibits increased specificity for the fourth region as compared to the specificity of the second primer for the second region. Specificity can include stronger hybridization, increased affinity or any other known measure for determining nucleic acid specificity. In some embodiments, the fourth primer has 10% greater, 20% greater, 30% greater, 40% greater, 50% greater, 60% greater, 70% greater, 80% greater, 90% greater, 100% greater, 110% greater, 120% greater, 130% greater, 140% greater, 150% greater, 160% greater, 170% greater, 180% greater, 190% greater, 200% greater, 250% greater, 300% greater or more increased specificity to the fourth region as compared to the second primer for the second region. In some embodiments, the fourth primer exhibits a higher Tm for the fourth region than the second primer does for the second region. In some embodiments, the fourth primer is longer than said second primer.

In some embodiments, the fourth primer comprises a sequence corresponding to the second adapter sequence in d). In some embodiments, the fourth primer includes a tag that includes a sequence that facilitates subsequent sequencing of the amplified cDNA. In some embodiments, the tag includes a sequence that facilitates binding the amplified sequence to a solid support. In some embodiments, a tag includes a bar-code or label to facilitate identification of the amplified T-cell receptor cDNA sequence. In some embodiments, the tag is part of the second adapter module.

In some embodiments, the fourth primer comprises a barcode. In some embodiments, the barcode sequence is adjacent to the second adapter module. In some embodiments, the fourth primer includes sequences corresponding to both the second adapter sequence in d) and a barcode. In some embodiments, the second adapter sequence in d) and a barcode are adjacent to each other. In some embodiments, the second adapter sequence in d) and a barcode are not adjacent to each other and have one or more additional sequences between the two.

In some embodiments, the second region and the fourth region do not overlap. In some embodiments, the second region and the fourth region partially overlap. In some embodiments, partial overlap refers to overlap by 1, 2, 3, 4, 5, 6, 7, 8, 9, or 10 nt. In some embodiments, partially overlap refers to overlap by 99% or less between the two sequences. In some embodiments, partially overlap refers to overlap by 1%, 5%, 10%, 20%, 30%, 40%, 50%, 60%, 70%, 80%, 90% or 95% between the two sequences. In some embodiments, partial overlap refers to 50% between the two sequences.

In some embodiments, the second primer and said fourth primer bind at regions that do not overlap. In some embodiments, the second primer and said fourth primer bind at regions that partially overlap. In some embodiments, partial overlap refers to overlap by 1, 2, 3, 4, 5, 6, 7, 8, 9, or 10 nt. In some embodiments, partially overlap refers to overlap by 99% or less between the two sequences. In some embodiments, partially overlap refers to overlap by 1%, 5%, 10%, 20%, 30%, 40%, 50%, 60%, 70%, 80%, 90% or 95% between the two sequences. In some embodiments, partial overlap refers to 50% between the two sequences.

In some embodiments, the primer binding to the constant region downstream of a recombination junction (e.g., a second primer and a fourth primer) are configured to bind to a sequence not associated with a common SNPs. In some embodiments, the second and fourth primers which bind to the C-region are configured to bind to regions within the C-region which do not contain SNPs. In some embodiments, the second region and fourth region to which the second and fourth primers bind, respectively, are selected to not contain common SNPs. "Single nucleotide polymorphism" ("SNP") and variants thereof refers to a site of one nucleotide that varies between alleles, as discussed above. A large body of information regarding SNPs is known and available to those of skill in the art and can be employed with the methods of the present invention in selecting binding regions and designing primers that do not bind to these regions. Information on common SNPs can be found in for example online databases such as the NCBI SNP database cal "dbSNP" (located on the World Wide Web at ncbi.nlm.nih.gov/snp) as well as the "Database of Genomic Variants" (located on the World Wide Web at dgv.tcag.ca/dgv/app/home).

A plurality of amplification products (e.g. first or second plurality of amplified products) indicates that the products generated are not all identical. As the methods of the present invention are directed toward generation of a T-cell receptor repertoire, the amplification products will contain the members from this repertoire. The plurality of amplification products (e.g. first or second plurality of amplified products) can contain 10 s, 100 s, 1000 s, 10,000 s, 100,0000 s 1,000,000 s, 10,000,000 s and up to $10^{16}$ or more unique amplification products.

VIII. PCR Primers and Primer Design

In some embodiments, primers are tested and designed in a laboratory setting. In some embodiments, primers are designed by computer based in silico methods. Primer sequences are based on the sequence of the amplicon or target nucleic acid sequence that is to be amplified. Shorter amplicons typically replicate more efficiently and lead to more efficient amplification as compared to longer amplicons.

In designing primers, one of skill would understand the need to take into account melting temperature ($T_m$; the temperature at which half of the primer-target duplex is dissociated and becomes single stranded and is an indication of duplex stability; increased $T_m$ indicates increased stability) based on GC and AT content of the primers being designed as well as secondary structure considerations (increased GC content can lead to increased secondary structure). $T_M$'s can be calculated using a variety of methods known in the art and those of skill would readily understand such various methods for calculating $T_M$; such methods include for example but are not limited to those available in online tools such as the $T_M$ calculators available on the World Wide Web at promega.com/techserv/tools/biomath/calcl 1.htm. Primer specificity is defined by its complete sequence in combination with the 3' end sequence, which is the portion elongated by Taq polymerase. In some embodiments, the 3' end should have at least 5 to 7 unique nucleotides not found anywhere else in the target sequence, in order to help reduce false-priming and creation of incorrect amplification products. Forward and reverse primers typically bind with similar efficiency to the target. In some instances, tools such as NCBI BLAST (located on the World Wide Web at ncbi.nlm.nih.gov) are employed to performed alignments and assist in primer design.

Those of skill in the art would be well aware of the basics regarding primer design for a target nucleic acid sequence and a variety of reference manuals and texts have extensive teachings on such methods, including for example, *Molecular Cloning* (three volume set, Cold Spring Harbor Laboratory Press, 2012) and *Current Protocols* (Genetics and Genomics; Molecular Biology; 2003-2013); the PrimerAnalyser Java tool available on the World Wide Web at primerdigital.com/tools/PrimerAnalyser.html and Kalendar et al. (Genomics, 98(2): 137-144 (2011)), all of which are incorporated herein in their entireties for all purposes.

An additional aspect of primer design is primer complexity or linguistic sequence complexity {see, Kalendar R, et al. (Genomics, 98(2): 137-144 (2011)). Primers with greater linguistic sequence complexity {e.g., nucleotide arrangement and composition) are typically more efficient. In some embodiments, the linguistic sequence complexity calculation method is used to search for conserved regions between compared sequences for the detection of low-complexity regions including simple sequence repeats, imperfect direct or inverted repeats, polypurine and polypyrimidine triple-stranded cDNA structures, and four-stranded structures (such as G-quadruplexes). In some embodiments, linguistic complexity (LC) measurements are performed using the alphabet-capacity L-gram method {see, A. Gabrielian, A. Bolshoy, Computer & Chemistry 23:263-274 (1999) and Y. L. Orlov, V. N. Potapov, Complexity: an internet resource for analysis of DNA sequence complexity, Nucleic Acids Res. 32: W628-W633 (2004)) along the whole sequence length and calculated as the sum of the observed range (xi) from 1 to L size words in the sequence divided by the sum of the expected (E) value for this sequence length. Some G-rich (and C-rich) nucleic acid sequences fold into four-stranded DNA structures that contain stacks of G-quartets {see, the World Wide Web at quadruplex.org). In some instances, these quadruplexes are formed by the intermolecular association of two or four DNA molecules, dimerization of sequences that contain two G-bases, or by the intermolecular folding of a single strand containing four blocks of guanines (see, P. S. Ho, PNAS, 91:9549-9553 (1994); L A. Mcheva, V. L. Florenfev, Russian Journal of Molecular Biology 26:512-531 (1992); D. Sen, W. Gilbert, Methods Enzymol. 211:191-199 (1992); P. A. Rachwal, K. R. Fox, Methods 43:291-301 (2007); S. Burge, G. N. arkinson, P. Hazel, A. K. Todd, K. Neidle, Nucleic Acids Res. 34:5402-5415 (2006); A. Guedin, J. Gros, P. Alberti, J. Mergny, Nucleic Acids Res. 38:7858-7868 (2010); O. Stegle, L. Payet, J. L. Mergny, D. J. MacKay, J. H. Leon, Bioinformatics 25:i374-i382 (2009); in some instances, these are eliminated from primer design because of their low linguistic complexity, LC=32% for (TTAGGG)$_4$.

These methods include various bioinformatics tools for pattern analysis in sequences having GC skew, (G−C)/(G+C), AT skew, (A−T)/(A+T), CG-AT skew, (S−W)/(S+W), or purine-pyrimidine (R−Y)/(R+Y) skew regarding CG content and melting temperature and provide tools for determining linguistic sequence complexity profiles. For example the GC skew in a sliding window of n, where n is a positive integer, bases is calculated with a step of one base, according to the formula, (G⁻C)/(G+C), in which G is the total number of guanines and C is the total number of cytosines for all sequences in the windows (Y. Benita, et al., Nucleic Acids Res. 31:e99 (2003)). Positive GC-skew values indicated an overabundance of G bases, whereas negative GC-skew values represented an overabundance of C bases.

Similarly, other skews are calculated in the sequence. Such methods, as well as others, are employed to determine primer complexity in some embodiments In some embodiments, the real-time PCR primers for use with the disclosed methods have a linguistic sequence complexity of at least 70%, at least 72%, at least 75%, at least 77%, at least 80%, at least 82%, at least 85%, at least 88%, at least 90%, at least 92%, at least 95%, at least 97% or at least 99%.

In some embodiments, the primers are designed to generate an alpha T-cell receptor repertoire. In some embodiments, the second and fourth primers are designed to bind the C-region of the alpha T-cell receptor. The alpha T-cell receptor can be from any organism, including those described herein or otherwise known.

In some embodiments, the primers are designed to generate a beta T-cell receptor repertoire. In some embodiments, the second and fourth primers are designed to bind the C-region of the beta T-cell receptor. The beta T-cell receptor can be from any organism, including those described herein or otherwise known.

In some embodiments, the alpha and beta TCRRs are generated separately. In some embodiments, the alpha and beta TCRRs are generated simultaneously, via mixing of the alpha and beta primers during the first and/or second amplification steps.

Exemplary primers for use with the methods of the present disclosure include but are not limited to the following:

Primers used to isolate Alpha TCR sequences in PCR 1 for Mouse:

```
F = universal adapter
                                        (SEQ ID NO: 1)
AATGATACGGCGACCACCGAGATCTACACTCTTTCCCTACACGACGCTCT

TCC GATC*T

R = TCR C alpha primer (mouse)
                                        (SEQ ID NO: 2)
TCCTGAGACCGAGGATCTTTTA
```

Primers used to isolate Alpha TCR sequences in PCR 2 for Mouse:

```
F = universal adapter
                                        (SEQ ID NO: 1)
AATGATACGGCGACCACCGAGATCTACACTCTTTCCCTACACGACGCTC

TTCC GATC*T

R = TCR C alpha primer (mouse)
                                        (SEQ ID NO: 3)
CAAGCAGAAGACGGCATACGAGAT[CGTGAT]GGTACACAGCAGGTTCT

GGGTTCTGGATGT
```

Primers used to isolate Beta TCR sequences in PCR 1 for Mouse:

```
F = universal adapter
                                        (SEQ ID NO: 1)
AATGATACGGCGACCACCGAGATCTACACTCTTTCCCTACACGACGCTC

TTCC GATC*T

R = TCR C beta primer (mouse)
                                        (SEQ ID NO: 4)
AAGGAGACCTTGGGTGGAGTCA
```

Primers used to isolate Beta TCR sequences in PCR 2 for Mouse:

```
F = universal adapter
                                        (SEQ ID NO: 1)
AATGATACGGCGACCACCGAGATCTACACTCTTTCCCTACACGACGCTCT

TCC GATC*T

R = TCR C beta primer (mouse)
                                        (SEQ ID NO: 5)
CAAGCAGAAGACGGCATACGAGAT[TGGTCA]CCTTGGGTGGAGTCAC

ATTTCTCAGATCCT
```

Primers used to isolate Alpha TCR sequences in PCR 1 for Human:

```
F = universal adapter
                                        (SEQ ID NO: 1)
AATGATACGGCGACCACCGAGATCTACACTCTTTCCCTACACGACGCTC

TTCC GATC*T

R = TCR C alpha primer (human)
                                        (SEQ ID No: 6)
CACTGGATTTAGAGTCTCTCAGC
```

Primers used to isolate Alpha TCR sequences in PCR 2 for Human:

```
F = universal adapter
                                        (SEQ ID NO: 1)
AATGATACGGCGACCACCGAGATCTACACTCTTTCCCTACACGACGCTC

TTCC GATC*T

R = TCR C alpha primer (human)
                                        (SEQ ID NO: 7)
CAAGCAGAAGACGGCATACGAGATTGGTCAGTGACTGGAGTTCAGACG

TGTGCTCTTCCGATCTNNNGCTGGTACACGGCAGGGTCA
```

Primers used to isolate Beta TCR sequences in PCR 1 for Human:

```
F = universal adapter
                                        (SEQ ID NO: 1)
AATGATACGGCGACCACCGAGATCTACACTCTTTCCCTACACGACGCTC

TTCC GATC*T

R = TCR C beta primer (human)
                                        (SEQ ID NO: 8)
TGCTTCTGATGGCTCAAACA
```

Primers used to isolate Beta TCR sequences in PCR 2 for Human:

```
F = universal adapter
                                        (SEQ ID NO: 1)
AATGATACGGCGACCACCGAGATCTACACTCTTTCCCTACACGACGCTC

TTCC GATC*T

R = TCR C beta primer (human)
                                        (SEQ ID NO: 9)
CAAGCAGAAGACGGCATACGAGATCACTGTGTGACTGGAGTTCAGACG

TGTGCTCTTCCGATCTNNNNNNCAGCGACCTCGGGTGGGAAC
```

IX. Amplification Product Analyses

The disclosed methods are used to isolate nucleic acids and analyze a particular subset of nucleic acids, those expressed as T-cell receptor mRNAs. In some embodiments, the method includes detecting the repertoire T-cell mRNAs expressed in T-cell population, which can include T-cell populations from biological samples as described herein.

In some embodiments, optionally, the plurality of products from the first round of PCR amplification are purified prior to performing the second round of PCR amplification.

In some embodiments, the methods described herein further comprises g) performing an analysis on the second amplified products obtained from step f). In some embodiments, the analysis comprises sequence analysis, SNP analysis, hybridization analysis and/or microarray analysis. In some embodiments, such analysis include detection of variety of genetic mutations, which include but are not limited to one or more deletions, insertions, transitions and trans versions. In some embodiments, the mutation is a single-nucleotide polymorphism (SNP).

A variety of methods for analyzing such isolated nucleic acids, for example but not limited to mRNA and cDNA are known in the art and include PCR methods, such as real-time PCR analysis, microarray analysis, hybridization analysis and nucleic acid sequence analysis, as well as a variety of other methods where nucleic acid compositions are analyzed and which are known to those of skill in the art. See, for example, Molecular Cloning (three volume set, Cold Spring Harbor Laboratory Press, 2012) and Current Protocols (Genetics and Genomics; Molecular Biology; 2003-2013).

A variety of sequencing techniques can be performed as part of the analysis of the plurality of second amplification products of the present invention. Any technique for sequencing nucleic acid known to those skilled in the art can be used in the methods described herein. DNA sequencing techniques include classic dideoxy sequencing reactions (Sanger method) using labeled terminators or primers and gel separation in slab or capillary, sequencing-by-synthesis using reversibly terminated labeled nucleotides, pyrosequencing, allele specific hybridization to a library of labeled oligonucleotide probes, sequencing-by-synthesis using allele specific hybridization to a library of labeled clones that is followed by ligation, real time monitoring of the incorporation of labeled nucleotides during a polymerization step, and SOLiD (Life Technologies, Inc.), Ion Torrent™ (Life Technologies, Inc.), HiSeq™ and MiSeg™, SOLEXA™, SMRT™, nanopore, Genome Sequencer FLX™ (Roche), and Chemical-Sensitive Field Effect Transistor Array Sequencing (chemFET) sequencing. Additional analysis techniques include true single molecule sequencing (tSMS; Helicos True Single Molecule Sequencing) (Harris T. D. et al. (2008) Science 320: 106-109), 454 Sequencing (Roche) (Margulies, M et al. 2005, Nature, 437, 376-380) as well as analyses using Illumina machines and methods.

X. Methods for Isolating mRNA from Immune Cells a. Lysis Solutions

A variety of lysis solutions have been described and are known to those of skill in the art. Any of these well-known lysis solutions can be employed with the present methods in order to isolate nucleic acids from a sample, in particular mRNA. Exemplary lysis solutions include those commercially available, such as those sold by INVITROGEN®, QIAGEN®, LIFE TECHNOLOGIES® and other manufacturers, as well as those which can be generated by one of skill in a laboratory setting. Lysis buffers have also been well described and a variety of lysis buffers can find use with the disclosed methods, including for example those described in *Molecular Cloning* (three volume set, Cold Spring Harbor Laboratory Press, 2012) and *Current Protocols* (Genetics and Genomics; Molecular Biology; 2003-2013), both of which are incorporated herein by reference for all purposes.

Cell lysis is a commonly practiced method for the recovery of nucleic acids from within cells. In many cases, the cells are contacted with a lysis solution, commonly an alkaline solution comprising a detergent, or a solution of a lysis enzyme. Such lysis solutions typically contain salts, detergents and buffering agents, as well as other agents that one of skill would understand to use. After full and/or partial lysis, the nucleic acids are recovered from the lysis solution.

In some embodiments, due the nature of present method of isolated mRNA, all solutions and equipment employed is RNAase free. Methods for RNAse decontamination and preparation of RNAse free solutions are well known to those of skill in the art and such methods can be readily applied as needed by one practicing the methods disclosed herein.

In some embodiments, cells are resuspended in an aqueous buffer, with a pH in the range of from about pH 4 to about 10, about 5 to about 9, about 6 to about 8 or about 7 to about 9.

In some embodiments, the buffer salt concentration is from about 10 mM to about 200 mM, about 10 mM to about 100 mM or about 20 mM to about 80 mM.

In some embodiments, the buffer further comprises chelating agents such as ethylenediaminetetraacetic acid (EDTA) or ethylene glycol tetraacetic acid (EGTA).

In some embodiments, the lysis solution further comprises other compounds to assist with nucleic acid release from cells such as polyols, including for example but not limited to sucrose, as well as sugar alcohols such as maltitol, sorbitol, xylitol, erythritol, and/or isomalt. In some embodiments, polyols are in the range of from about 2% to about 15% w/w, or about 5%> to about 15%) w/w or about 5% to about 10%>w/w.

In some embodiments, the lysis solutions further comprises surfactants, such as for example but not limited to Triton X-100, SDS, CTAB, X-114, CHAPS, DOC, and/or NP-40. In some embodiments such surfactants are in the range of from about 1% to about 5% w/w, about 1% o to about 4% w/w, or about 1% to about 3% w/w.

In embodiments, the lysis solution further comprises chaotropes, such as for example but not limited to urea, sodium dodecyl sulfate and/or thiourea. In some embodiments, the chaotrope is used at a concentration in the range of from about 0.5 M to 8 M, about 1 M to about 6 M, about 2 M to about 6 M or about 1 M to about 3 M.

In some embodiments, the lysis solution further comprises one or more additional lysis reagents and such lysis reagents are well known in the art. In some embodiments, such lysis reagents include cell wall lytic enzymes, such as for example but not limited to lysozyme. In some embodiments, lysis reagents comprise alkaline detergent solutions, such as 0.1 aqueous sodium hydroxide containing 0.5% sodium dodecyl sulphate.

In some embodiments, the lysis solution further comprises aqueous sugar solutions, such as sucrose solution and chelating agents such as EDTA, for example the STET buffer. In certain embodiments, the lysis reagent is prepared by mixing the cell suspension with an equal volume of lysis solution having twice the desired concentration (for example 0.2 sodium hydroxide, 1.0% sodium dodecyl sulphate).

In some embodiments, after the desired extent of lysis has been achieved, the mixture comprising lysis solution and lysed cells is contacted with a neutralizing or quenching reagent to adjust the conditions such that the lysis reagent does not adversely affect the desired product. In some embodiments, the pH is adjusted to a pH of from about 5 to about 9, about 6 to about 8, about 5 to about 7, about 6 to about 7 or about 6.5 to 7.5 to minimize and/or prevent degradation of the cell contents, including for example but not limited to the nucleic acids. In some embodiments, when the lysis reagent comprises an alkaline solution, the neutralizing reagent comprises an acidic buffer, for example an alkali metal acetate/acetic acid buffer. In some embodiments, lysis conditions, such as temperature and composition of the lysis reagent are chosen such that lysis is substantially completed while minimizing degradation of the desired product, including for example but not limited to nucleic acids such as mRNA.

Any combination of the above can be employed by one of skill, as well as combined with other known and routine methods, and such combinations are contemplated by the present invention.

b. mRNA Isolation

In some embodiments, the nucleic acids, including for example but not limited to mRNA, are isolated from a lysis buffer. Any of a variety of methods useful in the isolation of small quantities of nucleic acids are used by various embodiments of the disclosed methods. These include but are not limited to precipitation, gel filtration, density gradients and solid phase binding. Such methods have also been described in for example, *Molecular Cloning* (three volume set, Cold Spring Harbor Laboratory Press, 2012) and *Current Protocols* (Genetics and Genomics; Molecular Biology; 2003-2013), incorporated herein by reference for all purposes.

In some embodiments, total RNA used in the methods of the present disclosure can also be obtained from simple extraction methods, such as, Trizol extraction. Total RNA samples used in the present invention may or may not be treated with DNases prior to cDNA generation.

Nucleic Acid precipitation is a well know method for isolation that is known by those of skill in the art. A variety of solid phase binding methods are also known in the art including but not limited to solid phase binding methods that make use of solid phases in the form of beads (e.g., silica, magnetic), columns, membranes or any of a variety other physical forms known in the art. Substrates typically contain polyT tags, which bind to the polyA tail of the mRNA. Such substrates can include for example Ampure Beads form Beckman Coulter. In some embodiments, solid phases used in the disclosed methods reversibly bind nucleic acids. Examples of such solid phases include so-called "mixed-bed" solid phases are mixtures of at least two different solid phases, each of which has a capacity to nucleic acids under different solution conditions, and the ability and/or capacity to release the nucleic acid under different conditions; such as those described in U.S. Pat. No. 6,376,194, incorporated by reference herein in its entirety for all purposes. Solid phase affinity for nucleic acids according to the disclosed methods can be through any one of a number of means typically used to bind a solute to a substrate. Examples of such means include but are not limited to, ionic interactions (e.g., anion-exchange chromatography) and hydrophobic interactions (e.g., reversed-phase chromatography), pH differentials and changes, salt differentials and changes (e.g., concentration changes, use of chaotropic salts/agents). Exemplary pH based solid phases include but are not limited to those used in the INVITROGEN ChargeSwitch Normalized Buccal Kit magnetic beads, to which bind nucleic acids at low pH (<6.5) and releases nucleic acids at high pH (>8.5) and mono-amino-N-aminoethyl (MANAE) which binds nucleic acids at a pH of less than 7.5 and release nucleic acids at a pH of greater than 8. Exemplary ion exchange based substrates include but are not limited to DEA-SEPHAROSE™, Q-SEPHAROSE™, and DEAE-SEPHADEX™ from PHARMACIA (Piscataway, N.J.), DOWEX® I from The Dow Chemical Company (Midland, Mich.), AMBERLITE® from Rohm & Haas (Philadelphia, Pa.), DUOLITE® from Duolite International, In. (Cleveland, Ohio), DIALON TI and DIALON TIL.

Any individual method is contemplated for use alone or in combination with other methods, and such useful combination are well known and appreciated by those of skill in the art.

In some embodiments, lysis buffer is from an RNA sample preparation kits can be used and these include those commercially available from a variety of sources, including ILLUMINA® and QIAGEN® or any other commercial vendors.

XI. Methods for Preparing cDNA

The information contained in RNA in a sample can be converted to cDNA by using reverse transcription using techniques well known to those of ordinary skill in the art (see e.g., Sambrook, Fritsch and Maniatis, MOLECULAR CLONING: A LABORATORY MANUAL, 2nd edition (1989)). PolyA primers, random primers, and/or gene specific primers can be used in reverse transcription reactions. In some embodiments, polyA primers, random primers, and/or gene specific primers are employed in reverse transcription reactions in the presently described methods.

The cDNA of the present invention is prepared using any conventional methods for preparing cDNA. The standard method for preparing cDNA from mRNA is by reverse transcription-PCR. Reverse transcription-PCR (often referred to as RT-PCR) is a well-known technique that is regularly employed by those of skill in the art to convert mRNA into DNA and a variety of references are available and provide detailed protocols.

Conventional techniques for mRNA profiling include Northern hybridization, cloning, and microarray analysis. (Wang, Ach and Curry. 2007. Direct and sensitive miRNA profiling from low-input total RNA. RNA 13(1): 151-9, Wang and Cheng. 2008. A simple method for profiling miRNA expression. Methods Mol Biol 414: 183-90, Shingara, Keiger, Shelton, Laosinchai-Wolf, Powers, Conrad, Brown and Labourier. 2005. An optimized isolation and labeling platform for accurate microRNA expression profiling. RNA 11(9): 1461-70, Nelson, Baldwin, Scearce, Oberholtzer, Tobias and Mourelatos. 2004. Microarray-based, high-throughput gene expression profiling of microRNAs. Nat Methods 1(2): 155-61). Additional references include *Molecular Cloning* (three volume set, Cold Spring Harbor Laboratory Press, 2012) and *Current Protocols* (Genetics and Genomics; Molecular Biology; 2003-2013), which are incorporated herein by reference in their entireties.

XII. Samples

The present method of the present invention can be performed using mRNA isolated from any of a variety of biological samples containing T-cells. Methods for obtaining such samples are well-known to those of skill in the art and any appropriate methods can be employed to obtain samples containing or believed to contain T-cells. Biological samples may be stored if care is taken to reduce degradation, e.g. under nitrogen, frozen, or a combination thereof. The volume of sample used is sufficient to allow for measurable detection, for example from about 0.1 ml to 1 ml of a biological sample can be sufficient.

Biological samples for use in the methods provided in the present disclosure include, for example, a bodily fluid from a subject, including amniotic fluid (surrounding a fetus), aqueous humor, bile, blood and blood plasma, cerumen (earwax), Cowper's fluid or pre-ejaculatory fluid, chyle, chyme, female ejaculate, interstitial fluid, lymph, menses, breast milk, mucus (including snot and phlegm), pleural fluid, pus, saliva, sebum (skin oil), semen, serum, sweat, tears, urine, vaginal secretions, vomit, feces, internal body fluids including cerebrospinal fluid surrounding the brain and the spinal cord, synovial fluid surrounding bone joints, intracellular fluid (the fluid inside cells), and vitreous humour (the fluids in the eyeball. Biological sample contemplated by the disclosure also include biopsy samples from for example infection sites, cancer tissue or other diseased or potentially diseased tissue.

In some embodiments, the said biological sample is a body fluid sample and/or tissue sample. In some embodiments, the biological sample is selected from the group consisting of blood, plasma, serum, bone marrow, semen, vaginal secretions, urine, amniotic fluid, cerebrospinal fluid, synovial fluid and biopsy tissue samples, including from infection and/or tumor locations.

XIII. Diseases & Diagnostics

Diseased or infected tissues can be obtained from subjects with a wide variety of disease and disorders. Such disease and disorders include cancer, inflammatory diseases, autoimmune diseases, allergies and infections of an organism. The organism is preferably a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

Examples of cancer include prostrate, pancreas, colon, brain, lung, breast, bone, and skin cancers.

Examples of inflammatory conditions include irritable bowel syndrome, ulcerative colitis, appendicitis, tonsilitis, and dermatitis.

Examples of atopic conditions include allergy, asthma, etc.

Examples of autoimmune diseases include IDDM, RA, MS, SLE, Crohn's disease, Graves' disease, etc. Autoimmune diseases also include Celiac disease, and dermatitis herpetiformis. For example, determination of an immune response to cancer antigens, autoantigens, pathogenic antigens, vaccine antigens, and the like is of interest.

Examples of infections can include viral, fungal and bacterial, as well as antibiotic resistant bacterial infections. Examples of viral infections include influenza, cytomegalovirus (CMV), RSV, influenza virus, herpes simplex virus type 1, and parainfluenza virus. Examples of fungal infections include *Aspergillus* (e.g., *A. fumigatus*) or *Candida* (e.g., *Candida albicans*), and which may or may not exhibit resistance to antibiotic treatments. Examples of bacterial infections include Lysteria *monocytogenes, Pseudomonas* sp. (e.g., *P. aeruginosa*), *Serratia marcescens, Clostridium difficile, Staphylococcus aureus, Staphylococcus* sp., *Acinetobacter* sp., *Enterococcus* sp., *Enterobacteria* sp., *E. coli, Klebsiella* sp., *Streptococcus* (e.g., *S. pneumoniae*), *Haemophilus influenzae*, and *Neisseria meningitidis*. Examples of drug resistant or multi-drug resistant microorganisms include, *Staphylococcus aureus, Enterococcus* sp., *Pseudomonas* sp., *Klebsiella* sp., *E. coli*, and/or *Clostridium Difficile*. Examples of drug-resistant microorganisms include methicillin-resistant or vancomycin-resistant *Staphylococcus aureus* (MRSA or VRSA) including intermediate resistant isolates, and carbapenum-resistant *E. coli, Klebsiella*, or *Pseudomonas* including intermediate resistant isolates.

In some embodiments, samples including or believed to include T-cells are obtained from an organism after the organism has been challenged with an antigen (e.g., vaccinated). In other cases, the samples are obtained from an organism before the organism has been challenged with an antigen (e.g., vaccinated). Comparing the diversity of the T-cell receptor repertoire present before and after challenge, can assist the analysis of the organism's response to the challenge.

In some embodiments, the methods are employed in order to optimize therapy, for example by analyzing the T-cell receptor repertoire in a sample, and based on that information, selecting the appropriate therapy, dose, treatment modality, etc. that is optimal for stimulating or suppressing a targeted immune response, while minimizing undesirable toxicity. The treatment is optimized by selection for a treatment that minimizes undesirable toxicity, while providing for effective activity. For example, an organism may be assessed for the T-cell receptor repertoire relevant to an autoimmune disease, and a systemic or targeted immunosuppressive regimen may be selected based on that information.

A T-cell receptor repertoire signature for a condition can refer to a TCRR result that indicates the presence of a condition of interest. For example a history of cancer (or a specific type of allergy) can be reflected in the presence of T-cell receptor sequences that bind to one or more cancer antigens. The presence of autoimmune disease may be reflected in the presence of T-cell receptor sequences that bind to autoantigens. A signature can be obtained from all or a part of a dataset obtained by the methods of the present invention, usually a signature will comprise repertoire information from at least about 20 different T-cell receptor sequences, at least about 50 different T-cell receptor sequences, at least about 100 different T-cell receptor sequences, at least about $10^2$ different T-cell receptor sequences, at least about $10^3$ different T-cell receptor sequences, at least about $10^4$ different T-cell receptor sequences, at least about $10^5$ different T-cell receptor sequences, or more. Where a subset of the dataset is used, the subset may comprise, for example, alpha TCR or beta TCR, or a combination thereof.

The methods disclosed herein can also be utilized to analyze the effects of agents on T-cells of the immune system. For example, analysis of changes in T-cell receptor repertoire following exposure to one or more test compounds can performed to analyze the effect(s) of the test compounds on an individual. Such analyses can be useful for multiple purposes, for example in the development of immunosuppressive or immune enhancing therapies. Agents to be analyzed for potential therapeutic value can be any compound, small molecule, protein, lipid, carbohydrate, nucleic acid or other agent appropriate for therapeutic use. In some embodiments, tests are performed in vivo, e.g. using an animal model, to determine effects on the immune repertoire.

Agents of interest for screening include known and unknown compounds that encompass numerous chemical classes, primarily organic molecules, which may include organometallic molecules, genetic sequences, etc.

Agents include organic molecules comprising functional groups necessary for structural interactions, particularly hydrogen bonding, and typically include at least an amine, carbonyl, hydroxyl or carboxyl group, frequently at least two of the functional chemical groups. The candidate agents can include cyclical carbon or heterocyclic structures and/or aromatic or polyaromatic structures substituted with one or more of the above functional groups.

Agents include biomolecules, including peptides, polynucleotides, saccharides, fatty acids, steroids, purines, pyrimidines, derivatives, structural analogs or combinations thereof. In some instances, test compounds may have known functions (e.g., relief of oxidative stress), but may act through an unknown mechanism or act on an unknown target. Included are pharmacologically active drugs, genetically active molecules, etc. These include chemotherapeutic agents, hormones or hormone antagonists, etc. Exemplary of pharmaceutical agents suitable for this invention are those described in, "The Pharmacological Basis of Therapeutics," Goodman and Oilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Compounds, including agents, are obtained from a wide variety of sources including libraries of synthetic or natural compounds. Libraries of natural compounds in the form of bacterial, fungal, plant and animal extracts are available or readily produced. Natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

XIV. Databases of TCRR and Data Analysis

Also provided by the present disclosure are databases of TCRRs. Such databases comprise TCRR results derived from various individual conditions, such as individuals having exposure to a vaccine, to a cancer, having an autoimmune disease of interest, infection with a pathogen, etc., using the methods described herein. Such databases include sequences of immunological receptors derived from synthetic libraries, or from other artificial methods. The repertoire results and databases thereof can be provided in a variety of media to facilitate their use. "Media" refers to a manufacture that contains the expression repertoire information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. One of skill I the art can readily appreciate that any one of the currently available computer-based system are suitable for use in the present invention. The data storage means can comprise any manufacture comprising a recording of the information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the TCRR.

A scaled approach may also be taken to the data analysis. For example, Pearson correlation of the TCRR results can provide a quantitative score reflecting the signature for each sample. The higher the correlation value, the more the sample resembles a reference TCRR. A negative correlation value indicates the opposite behavior. The threshold for the classification can be moved up or down from zero depending on the clinical or diagnostic goal.

To provide significance ordering, the false discovery rate (FDR) may be determined. First, a set of null distributions of dissimilarity values is generated. In one embodiment, the values of observed repertoires are permuted to create a sequence of distributions of correlation coefficients obtained out of chance, thereby creating an appropriate set of null distributions of correlation coefficients (see, Tusher et al. *PNAS* 98:51 18-21 (2001), herein incorporated by reference). The set of null distribution is obtained by: permuting the values of each TCRR for all available TCRRs; calculating the pairwise correlation coefficients for all repertoire results; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental repertoires.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among repertoires. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein. A variety of structural formats for the input and output means can be used to input and output the information in the computer-based systems of the present invention. One format for an output tests datasets possessing varying degrees of similarity to a trusted TCRR. Such presentation provides one of skill in the art with a ranking of similarities and identifies the degree of similarity contained in the test repertoire.

Storing and Transmission of Data: The present disclosure further contemplates the need for storing and transmission of data. As such, a method of storing and/or transmitting, via computer, sequence, and other, data collected by the methods disclosed herein is provided. Any computer or computer accessory including, but not limited to software and storage devices, can be utilized to practice the present invention. Sequence or other data (e.g., TCRR analysis results), can be input into a computer by a user either directly or indirectly. Additionally, any of the devices which can be used to sequence DNA or analyze DNA or analyze TCRR data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location XV. Reagents and Kits Also provided are reagents and kits thereof for practicing one or more of the above-described methods. The subject reagents and kits thereof may vary greatly and can include any of the reagents and components described herein.

Reagents of interest include reagents specifically designed for use in the generation and or the analysis of the TCRR. For example, reagents can include primer sets for cDNA synthesis, reagents for ligation, primer sets for PCR amplification.

The kits of the subject invention can include the above described gene specific primer collections. The kits can further include a software package for statistical analysis, and may include a reference database for calculating the probability of a match between two TCRRs. The kit may include reagents employed in the various methods, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, DNA kinase, DNA ligases and the like, various buffer mediums, e.g. hybridization and washing buffers, ligation buffers, and components, like spin columns, etc.

In addition to the above components, the subject kits will further include instructions for practicing the subject methods. These instructions may be present in the subject kits in a variety of forms, one or more of which may be present in the kit, and which include a printed and/or or computer readable format.

In some embodiments, a software product (or component) includes instructions for assigning the TCRR data into V, D, J, C, VJ, VDJ, VJC, VDJC, or VJ/VDJ regions or instructions for displaying an analysis output in a multi-dimensional plot.

In some embodiments, a multidimensional plot enumerates all possible values for one of the following: V, D, J, or C. (e.g., a three-dimensional plot that includes one axis that enumerates all possible V values, a second axis that enumerates all possible D values, and a third axis that enumerates all possible J values). In some cases, a software product (or component) includes instructions for identifying one or more unique patterns from a single organism sample correlated to a condition. The software product (or component) may also include instructions for normalizing for amplification bias. In some examples, the software product (or component) may include instructions for using control data to normalize for sequencing errors or for using a clustering process to reduce sequencing errors.

EXAMPLES

Example 1: Mechanisms that Generate TCR Diversity

Each chain of the TCR receptor can be coded by one of the four multigene families (α, β, γ, δ). In mice, α, β, γ gene segments are located on the chr.14, 6 and 13 respectively while the δ gene segment is present in between a Vα and Jα segment on the chr.14. The organization of the TCR loci of mice and human (FIG. 1) consists of an array of Variable (V), Diversity (D, present only in β and δ), Joining (J) and Constant (C) gene segments. Assembly of these genes is what generates the diversity of the T cell repertoire. One pair of VDJC (in β, δ) or VJC (in α, γ) is selected from one allele in each developing thymocyte, and this pair then remains unique to that cell and its progeny (Caccia et al., 1984).

Figure 2:
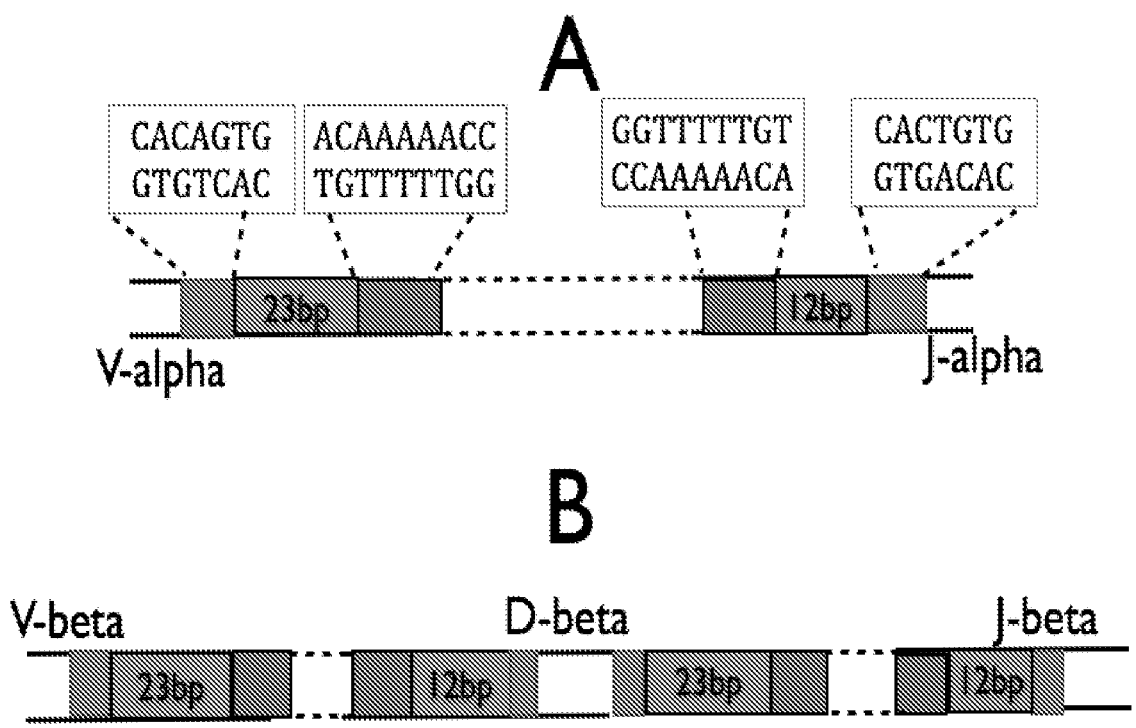
FIG. 2: The recognition signals used by the recombination machinery. Panel A depicts the arrangement of the signals in the α chain, Panel B shows the arrangement of signals in the β chain. The recombination process obeys the 12-23 rule, where a recognition signal with a 12-nt spacer can only recombine with another with a 23-nt spacer. There is some freedom in the exact recognition sequence and variations in these can potentially affect the efficiency of recombination of different pairs.
Figure 3:
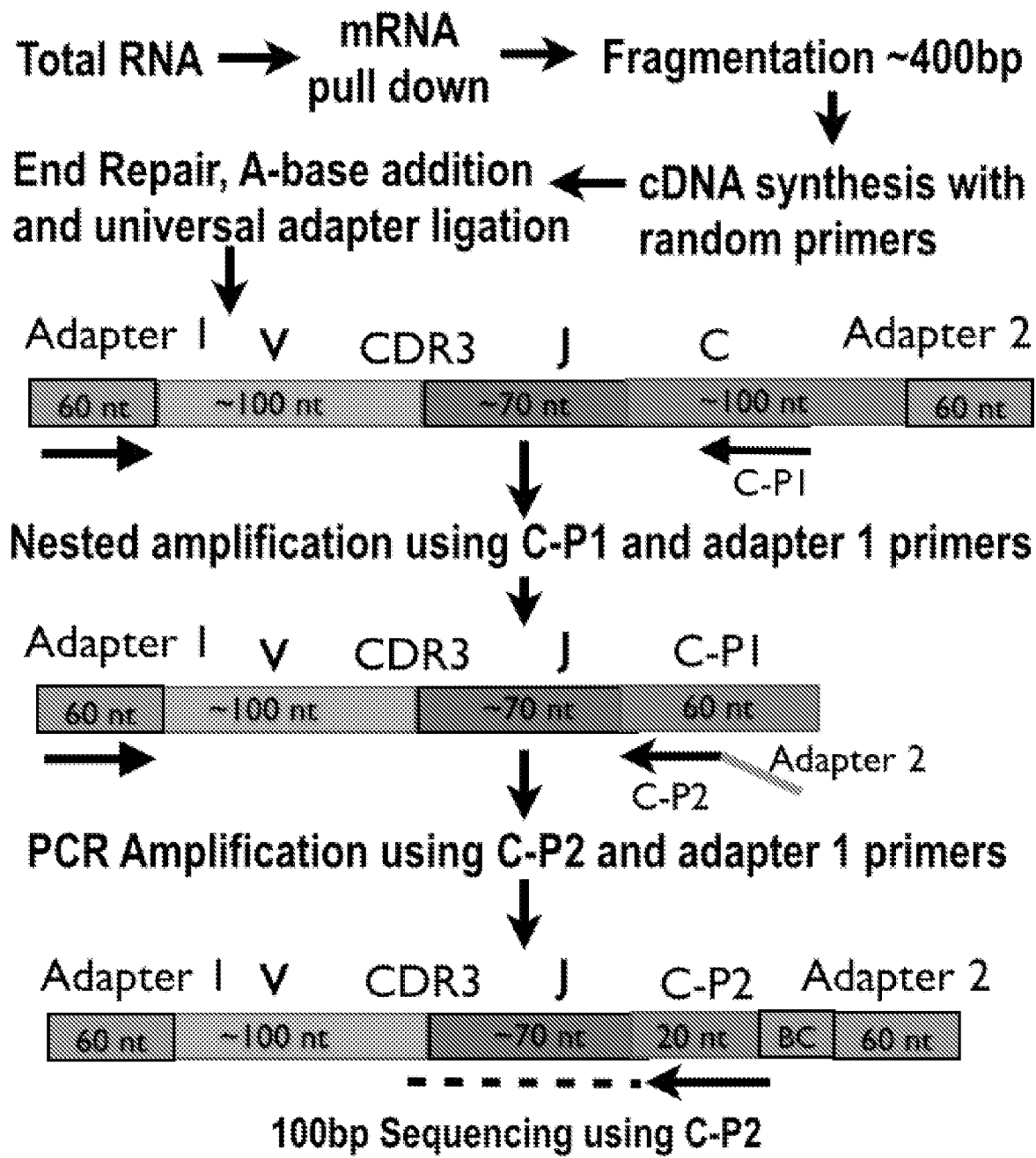
FIG. 3: T-seq protocol. The key steps are 1) the fragmentation of mRNA, and ligation of adapters to cDNA synthesized from the fragments, 2) amplification with a primer from the C-region on the 3' end (C-P1, one each for α and β) and the universal 5' adapter (adapter 1), 3) A nested PCR using adapter 1 on the 5' end and a second 3' primer in the C (C-P2) to which is attached barcodes and Adapter 2, resulting in the final sequence. This is then sequenced using C-P2 as a custom primer.

Enzymes that are involved in the recombination process include the RAG (Recombination Activating Genes) proteins that recognize Recombination Signal Sequences (RSS). RSS flank each gene segment and consist of a heptamer (CACAGTG) and a conserved nonamer (ACAAAAACC), which is separated by a spacer of 12 or 23 bp. The recombination process obeys the 12-23 rule, where recognition signal with a 12-nt spacer can only recombine with another with a 23-nt spacer (FIG. 2).

The frequency of recombination of certain V (D) J pairs can be greatly reduced, depending on the extent of alterations in the RSS (Nikolich-Zugich et al., 2004; Schatz and Ji, 2011). By combinatorial joining and random addition of nucleotides, at least $10^{16}$ (possibly a lot more) TCRs can be formed hut not all of them make the mature functional repertoire. Thymic selection is thought to reduce the repertoire to $\sim 10^{13}$ possible combinations (in mice to $\sim 1$-$2 \times 10^8$ T cells) (Casrouge et al., 2000; Doherty et al., 2000).

Results:
A Novel Method to Sequence the TCR Repertoire

Figure 4:
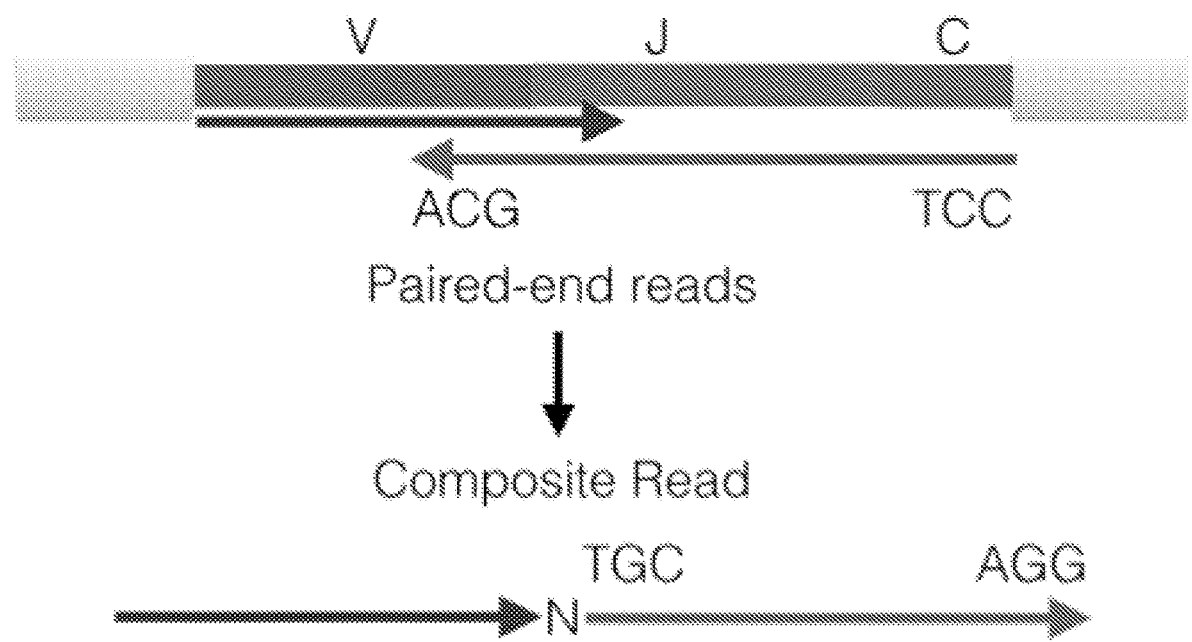
FIG. 4: The geometry of the forward and reverse reads generated by T-seq, using paired-end sequencing, is depicted here. The gray boxes at the ends are the sequencing adapters. The reads are processed to generate a composite from the forward and reverse read.

The T-seq technique (Figure. 4.4) overcomes the limitations of current approaches. Universal primers are ligated to fragmented mRNA and nested PCR performed, with two 3' oligos from the constant C region and the universal 5' adapter as the second primer (Figure. 4.4).

This unbiased approach is highly efficient (>95% of reads are CDR3, for TCR repertoire of α and β) and allows discovery of novel segments while reducing the sequencing cost substantially. The geometry of the forward and reverse reads is shown in FIG. 4.

The fragments of mRNA are on average in the 200-400 nt range. Since the 3' end is anchored at the start of the C segment, it is almost guaranteed that the forward read will start at a V and the reverse read will span the J and reach into V. With appropriate choice of sequencing lengths (say 50 nt forward and 150 nt in reverse) the TCR repertoire can be efficiently characterized. The key features are the design of primers to avoid common SNPs in the TCR and the nested PCR steps that confer specificity to the process. The method has been extensively tested in mice, whose TCR locus is very similar to the human one, as seen in FIG. 2. Initial tests of T-seq have been performed in humans and found it to be as effective as in mice at profiling the TCR landscape of a heterogeneous population of T cells.

Analytical Methods:
The annotations of the TCR loci have been a major challenge despite the excellent resources provided by the IMGT (Lefranc et al., 2009). Analysis of the sequencing data is complicated by the variability in the CDR3 region of the TCR-β sequence and the small D and J segments. Several recent papers map reads to the IMGT annotations to determine the use of V and J segments. IMGT has a site that allows single sequence analysis. The Slansky lab (Slansky, 2011) has a website that allows uploading up to 250,000 reads to analyze them for known V and J regions obtained from IMGT and Arden (Arden et al., 1995; Lane et al., 2010). However, the websites do_not analyze the CDR3 segments. When describing the current approach to generating sequencing libraries focused on TCR sequences, an approach based on gathering sequences solely on the basis of the C region is advantageous over approaches depending on combinations of V region primers. Because all TCR encoding mRNAs of a given type (α or β) share the C region sequence and so the current approach can capture all sequences, while approaches depending on mixes of V region primers can only find what the mixes of primers will allow. The biases in the efficiencies of detection of known sequences, also caused by the mixes of V region primers used, was another reason we gave for our approach which captures TCR mRNAs based on C region sequences. In this section, detailing the sequence analysis pipeline, a similar argument is made: that the methods used prior the method described in this application all depend on the IMGT database only allow analyses of TCRs containing known Vs. Below, data presented showing that the method described in the present application has already found TCR sequences that would have been missed by an IMGT-based approach.

Figure 5:
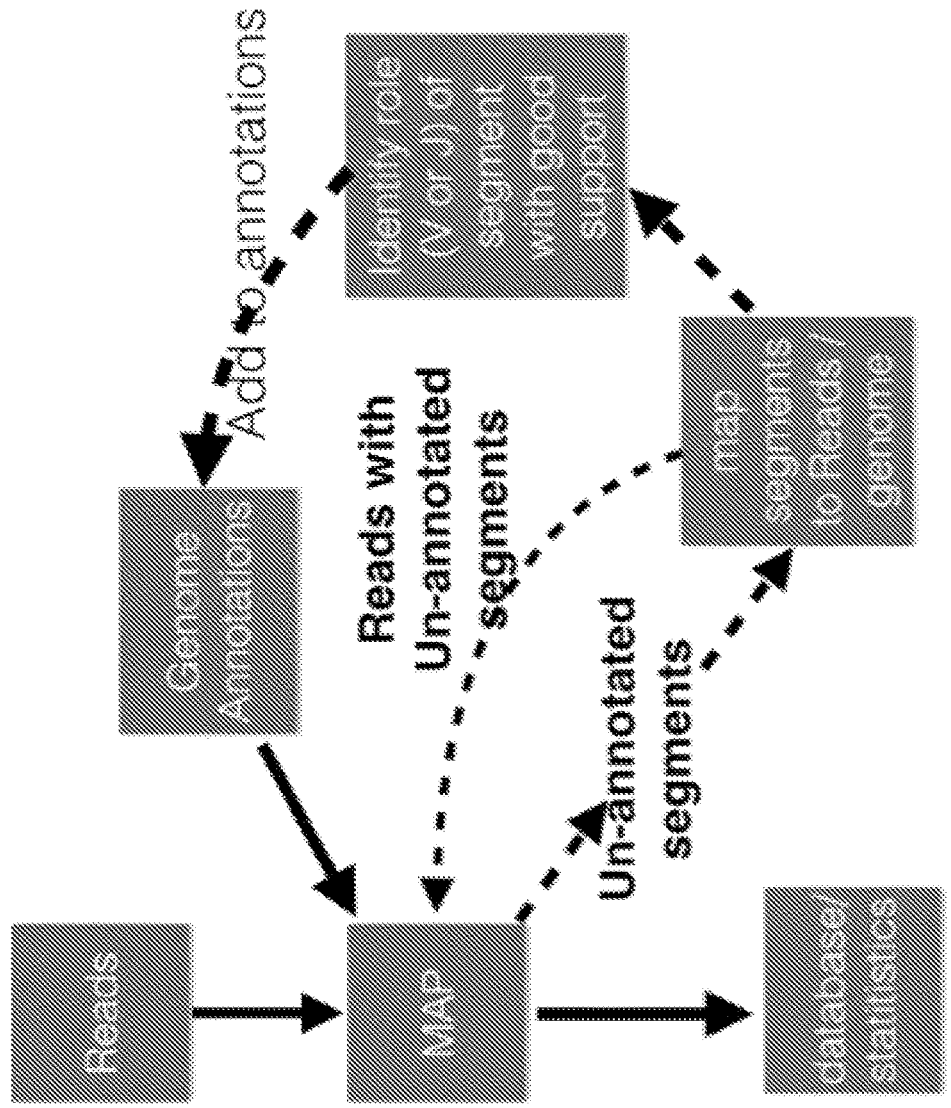
FIG. 5: Pipeline for processing the composite reads from T-seq to generate TCR-repertoire statistics, as well as novel annotations. Un-annotated reads are ones with substantial segments that do not map to known TCR elements. The un-annotated segments get mapped to the genome (to identify origin), as well as other reads (to identify frequency) before being recognized as novel TCR elements. The dotted lines show sections that are recursively applied, adding newly identified elements to the genome annotations and then processing the un-annotated reads, till most of the reads can be characterized as bonafide TCR repertoire reads.
Figure 6:
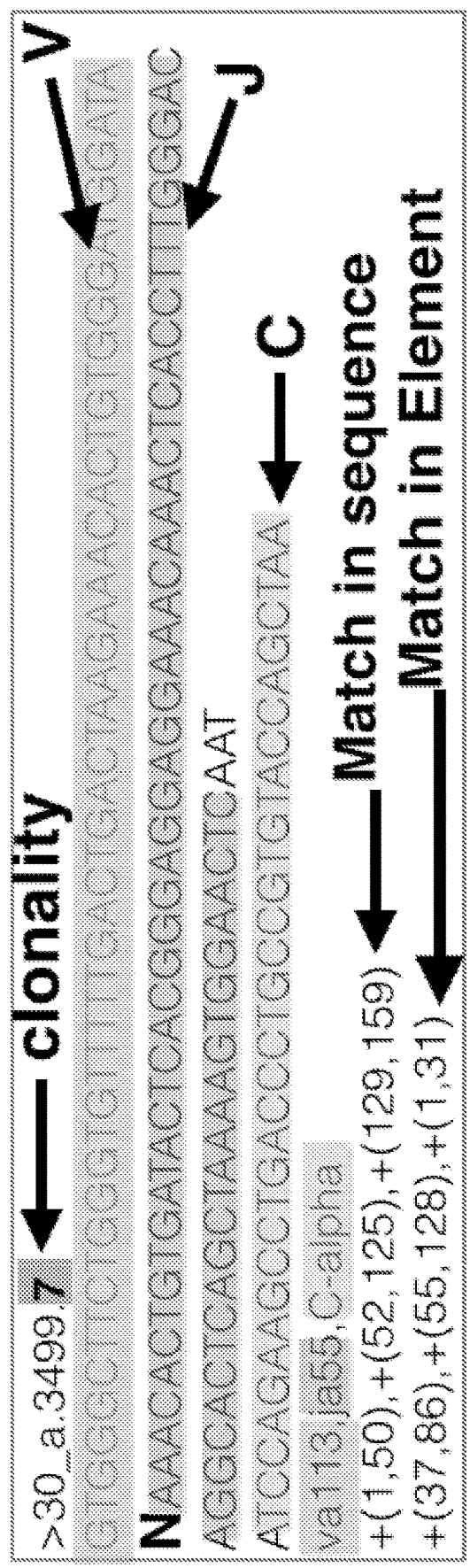
FIG. 6: The pipeline shown in FIG. 5 is used to annotate different parts of the composite read, generated as shown in FIG. 3. It is a fasta-like format; the first line consists of the name and a number showing clonality of the read. The next line is the composite read, the row after that gives the various annotations (V, J and C) and the last two rows are the matches from the composite read to matches on the corresponding V/J/C elements. This allows identification of the CDR3, helps identify novel segment usage and helps better annotate the TCR loci, feeding into the recursive procedure described in FIG. 5.

Current methods of sequence analysis: A new pipeline was designed, tailored to the method described herein, to measure usage of various segments and identify novel segments or combinations (such as alternative use of a leader sequence with different V segments). We used annotations compiled from the IMGT and EST databases to create non-redundant TCR-segment sequences, which we grouped into sets of Vs, Js, Ds and Cs. Using BLAST in sensitive settings (blastn, word size W set at 7), we mapped the sequences from our experiments to the non-redundant set, and for each read, identified Vs, Ds, Js and Cs. The processing pipeline is depicted in FIG. 5 and FIG. 6 shows the output of the analytical pipeline, which tracks the clonality and the various annotations (or lack thereof).

Figure 7:
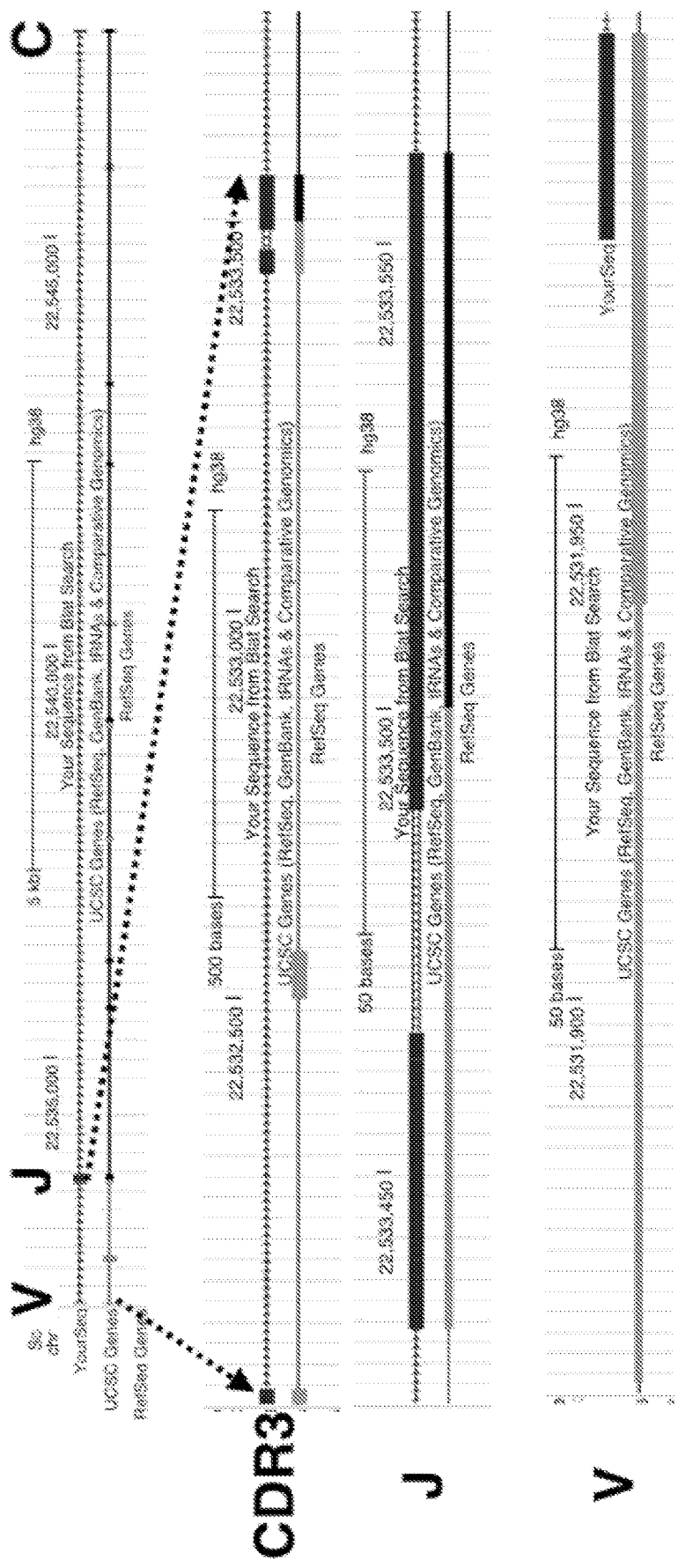
FIG. 7: An alpha read (black, upper row in each panel) mapped to the human TCR alpha locus. The top row shows maps to the V, J and C segments. The forward read maps uniquely to a V and crosses into a J, thus spanning the CDR3. The reverse read maps to a J and crosses the 3' end of J into the C. Both ends of the J are defined here but the middle is not covered by the read.

TCR repertoires from 20 mice and four humans have been analyzed. The present example provides examples of characterized TCR sequences and then describes the overall similarities amongst various mice that were analyzed in these studies. The pipeline allows us to explore sequences with varying degrees of coverage of the particular TCR under study. An example of a TCR alpha sequence where the CDR3 was covered in addition to the V and J sequences is shown in FIG. 7.

Figure 8:
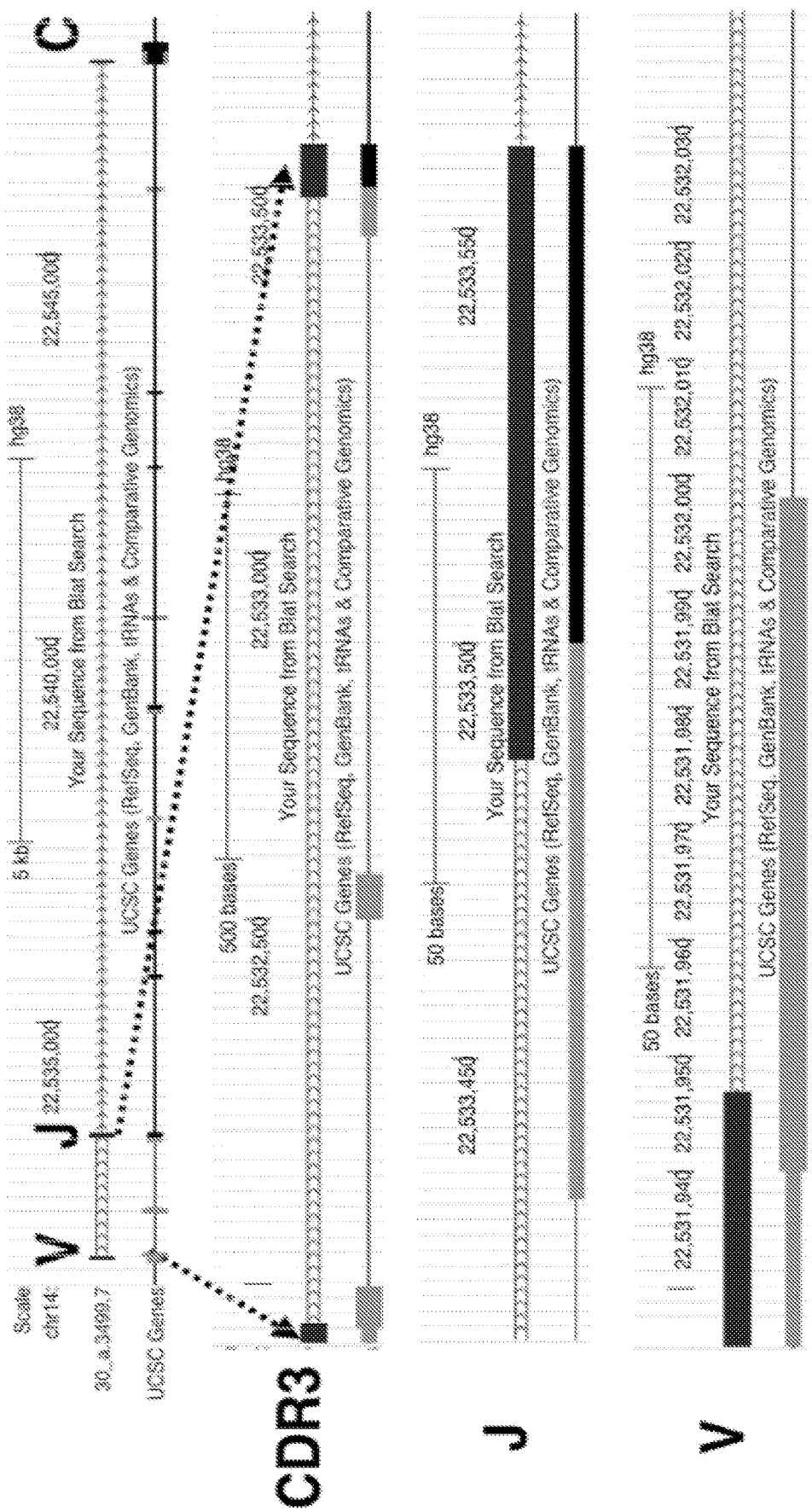
FIG. 8: An alpha read (black, upper row in each panel) mapped to the human TCR alpha locus. The top row shows maps to the V, J and C segments. The forward read maps uniquely to a V, while one end of the reverse maps to a J and crosses the 3' end of J into the C. The 5' end of J is not covered, and no part of the read spans the V-J segment. Thus the CDR3 sequence cannot be determined in such cases. This occurs when the fragment goes deep into the V, so the forward read cannot span the CDR3 unless we sequencer longer forward reads (these were done with 50 nt forward reads).

Not all sequences cover the full CDR3, and FIG. 8 shows an instance where while the V-J combination was identified but the CDR3 was left unspecified. Thus V-J frequencies were more reliably determined, while the CDR3 sequences are sometimes missed. Longer sequencing of forward and reverse reads can rectify this. Some un-annotated parts can be due to CDR3, whose analysis is described below. Sequences with gaps in annotation are manually curated and the annotation database was updated if there was sufficient support in the data for a particular novelty (FIG. 5). Rare events were flagged for analysis over several samples to accumulate sufficient evidence. An important aspect of our approach was that novel TCR configurations can be discovered and characterized.

Figure 9:
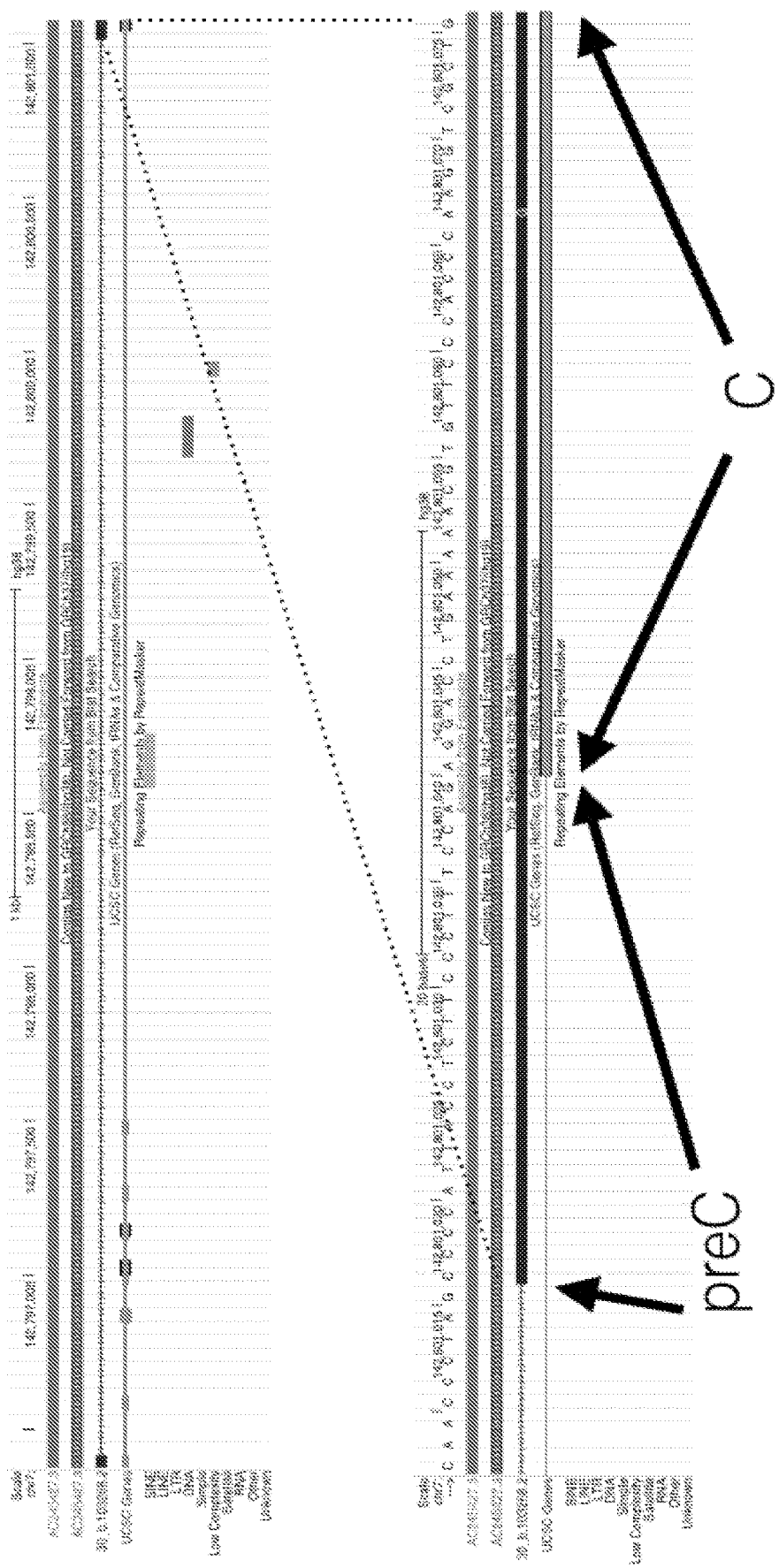
FIG. 9: A novel segment (preC) before the canonical C, seen in about 2.5% of reads in human β, in both C1 and C2. The preceding J seems to have no influence on the preC. A similar phenomenon occurs in mouse but only in the C1 as a 72 nt extension on the 5' end. The bottom panel is a zoomed in view of the C-region. This is an alternative splicing event.

Using this simple logical pipeline many unusual segments were uncovered. For example, A novel, in frame, 'preC' sequence in the human TCR β was present in 2.5% of reads from multiple individuals. These preC sequences showed up both in the C1 and C2 parts of the cluster. The preC was present along with all J segments at similar levels as would be expected from the non preC-containing TCR sequences. Alternative splicing allows for these preC-containing transcripts. The preC segment has been observed previously in mice TCR β (Behlke and Loh, 1986) and is shown in FIG. 9 from our data.

Figure 10A:
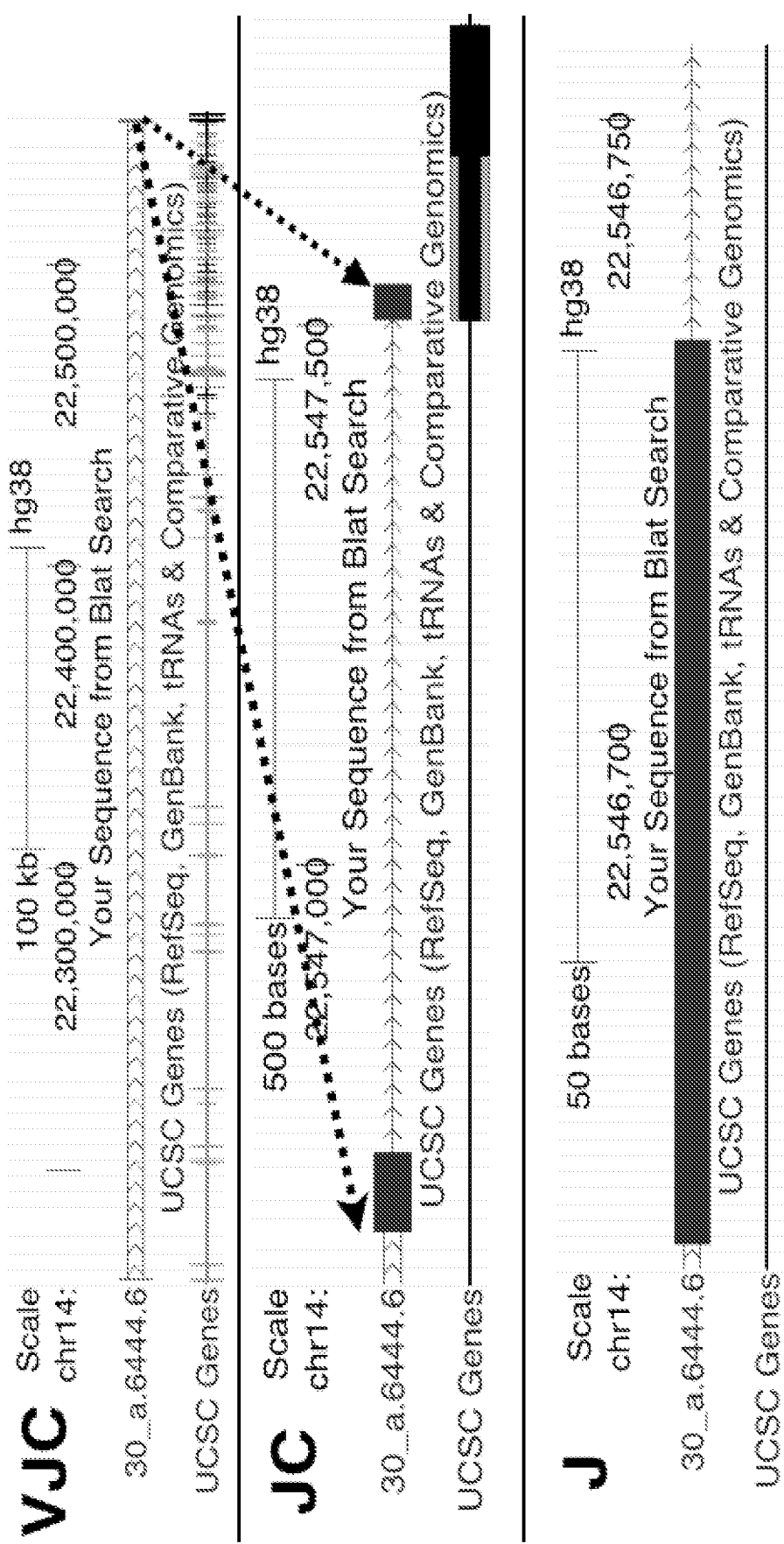
FIG. 10*a*: A novel J segment in the human TCR alpha locus. The mapping to V,J and C segments is shown here. The ucsc gene track, which shows known segments, has nothing under the J we have identified, while the C has a ucsc gene. We have numerous reads spanning this J and mapping into V and C to give us confidence in this identification.
Figure 10B:
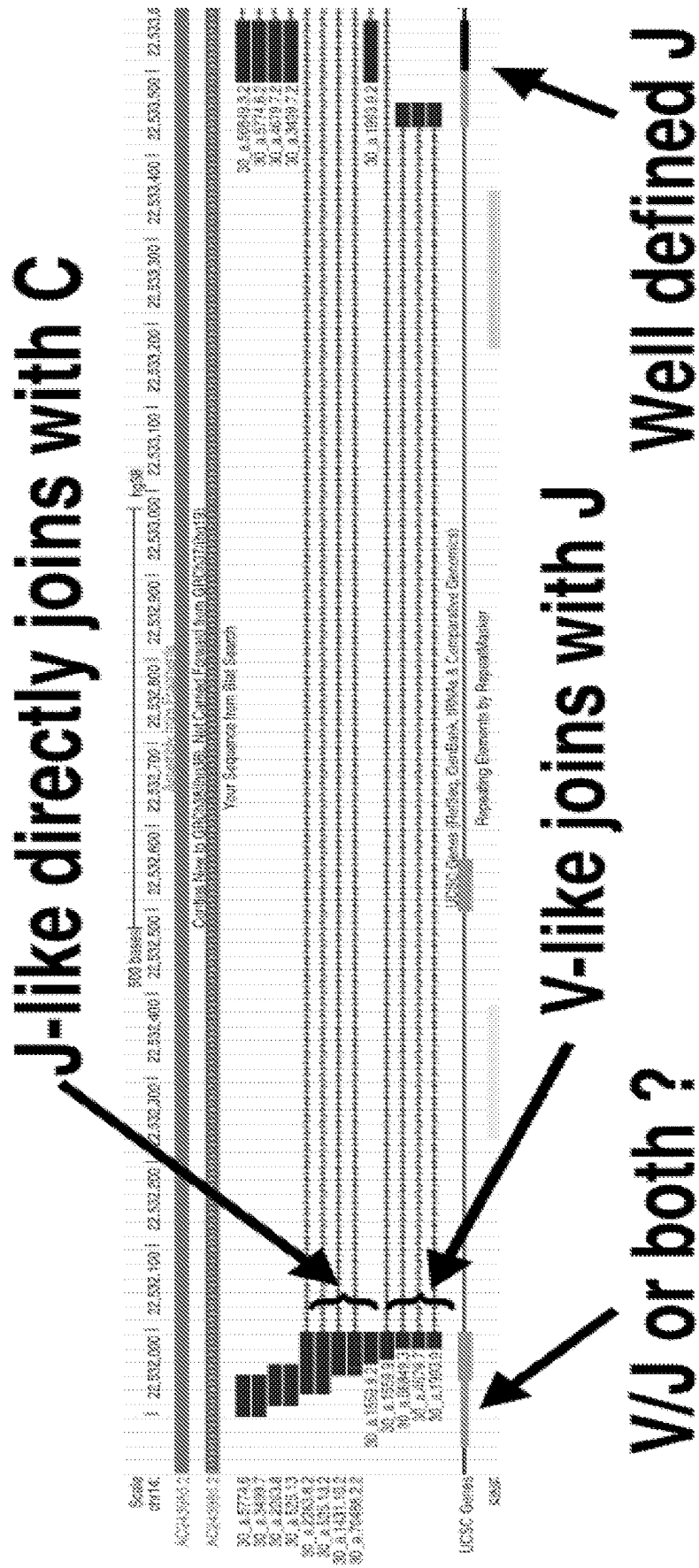
FIG. 10*b*: A human alpha segment with a dual role? In the human samples we have reads that start at the segment directly bridge to the C, which would make it a J segment, while other reads start from the same segment, but bridge to a J, and another part bridges the J to the C, which would make a V segment. All samples had evidence of this. There is a possibility this arises from incorrect assembly of this region, or individual variations in the genome.

A novel TCR α J segment is shown in FIG. 10*a*. This novel J segment occurred in over a hundred reads in all four human samples and was associated with various V regions. FIG. 10*b* shows a segment that potential has a dual role as a V and a J.

Table 4.1 shows the number of elements that have been annotated in the TCR loci in mouse and human based on the sequencing data and methods described herein.

|  | V α | J α | V β | J1 β | J2 β |
|---|---|---|---|---|---|
| Mouse | 97 | 56 | 39 | 6 | 7 |
| Human | 98 | 65 | 41 | 7 | 6 |

Cdr3 Curation:

The CDR3s for TCR-β were curated by mapping the D sequences to the reads using the Smith-Waterman-Gotoh algorithm (Gotoh, 1982) to identify the appropriate D and various non-templated parts. The CDR3 of TCR α was easier to identify, as the number of un-templated bases were far fewer compared to the TCR β. The amino-acid sequences of the CDR3s were identified by comparing the translations of the three frames with the terminal amino acids of the preceding V-segment (Table 4.2).

TABLE 4.2

Examples of the frequency of CDR3 for TCR-β in three strains of mice, with two mice in each strain; b10d2 (blod), balb/c (bal) and black-6 (bl).

|  | CDR3 nucleotide | CDR3 peptide | 10d | 10d | al | al | l | l |
|---|---|---|---|---|---|---|---|---|
| 2S1 1S3 | TACTGCACCT GCAGTGCAGA CAATTCTGGA AATACGCTCT (SEQ ID NO: 10) | YCTCSADNSGNTL (SEQ ID NO: 11) | 50 | 00 |  |  |  |  |
| 2S1 2S3 | TACTGCACCT GCAGTGCAGA TGCAGAAACG CTGTATTTTG (SEQ ID NO: 12) | YCTCSADAETLYF (SEQ ID NO: 13) | 00 | 020 |  |  |  |  |
| 1S1 2S7 | TTTTGTGCCAG CAGCCAAGGA CAGTATGAAC AGTACTTCG (SEQ ID NO: 14) | FCASSQGQYEQYF (SEQ ID NO: 15) | 0 | 00 |  |  | 0 | 0 |

Characterizing the TCR Repertoire in Mice:

Measuring V, D J Usage.

The analysis started with the simplest characterizations of the data, involving frequencies of V and J elements. The distribution of TCR β J's (Figure. 4.12) suggests a strong bias for certain J's; the J2 group is used more than the J1 group under quiescent conditions (unperturbed immune system).

The differential usage arose from a combination of the differing strengths of the RSSs in the genome as well as differential selection and growth [13]. We have also observed similar data with the TCR α analyses. As they are often very changed by the deletions/insertions of VDJ recombination, the Ds are more difficult to categorize, so we leave it to the CDR3 analyses described below to address the important role Ds play in the repertoire.

Figure 12:
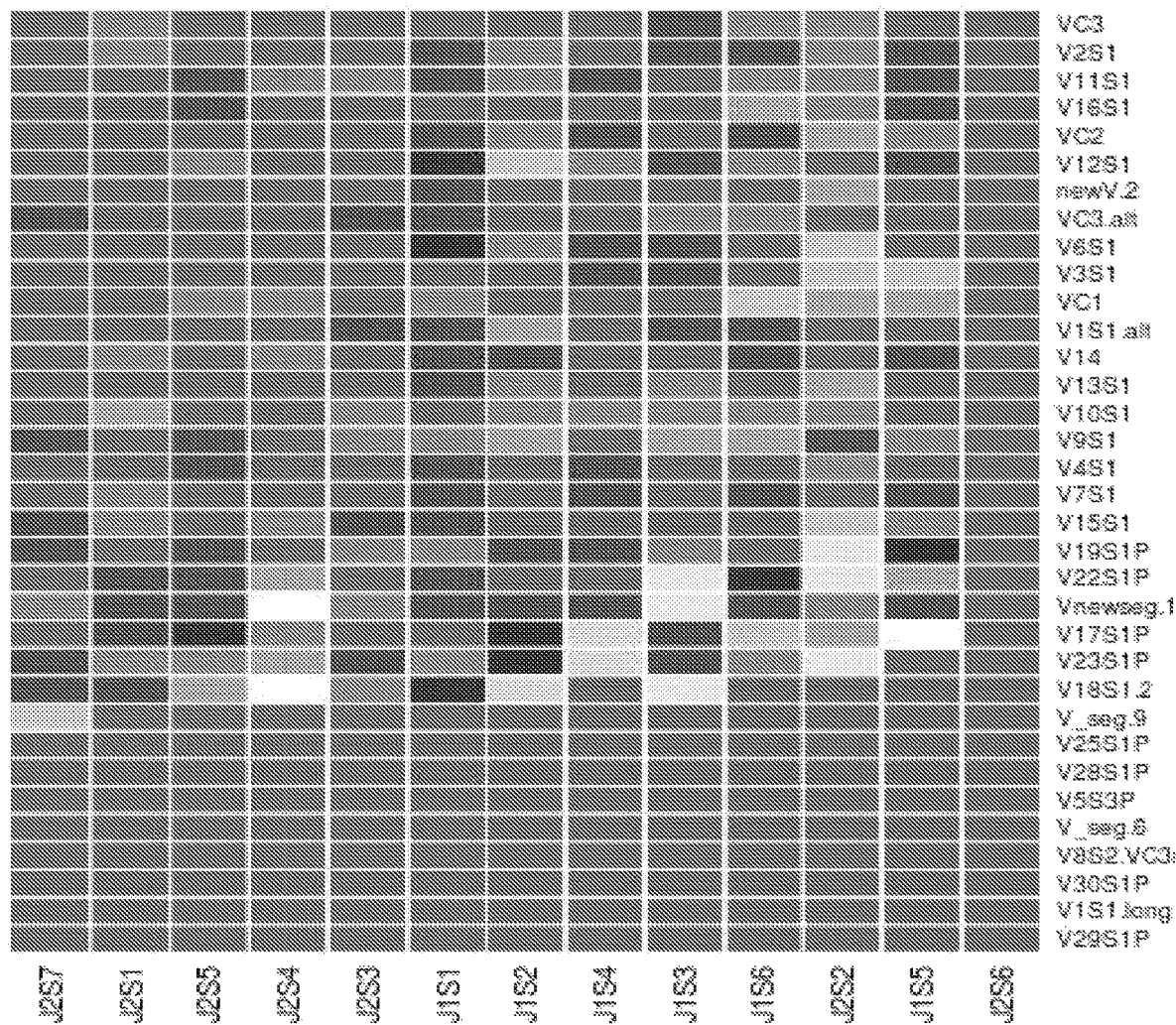
FIG. 12: Combinations of V and J β as a matrix. The log-odds score for each combination is shown using colors. Darker (lighter) colors are combinations that are more (less) common than expected. The most abundant elements are at the top of the rows (V's) and to the left of the columns (J's). A chi-square test can determine correlations between the V's and the J's.

Combinations of V-J Elements:

A next level of analysis was to examine the frequencies of the V-J combinations. FIG. 12 presents observed vs. expected frequencies of particular TCR β V-J combinations given the underlying V and J usage frequencies; the expected frequency for a each particular V-J combination is simply the product of the frequency of the V and J which make up that V-J combination. In FIG. 12, increasingly darker colors indicate over-representation of a given V-J combination, while lighter colors represent under-representation. FIG. 12 was made using over a million sequencing reads and many more such analyses will be performed when we have amassed greater sequencing depth on samples from different mice.

Figure 13:
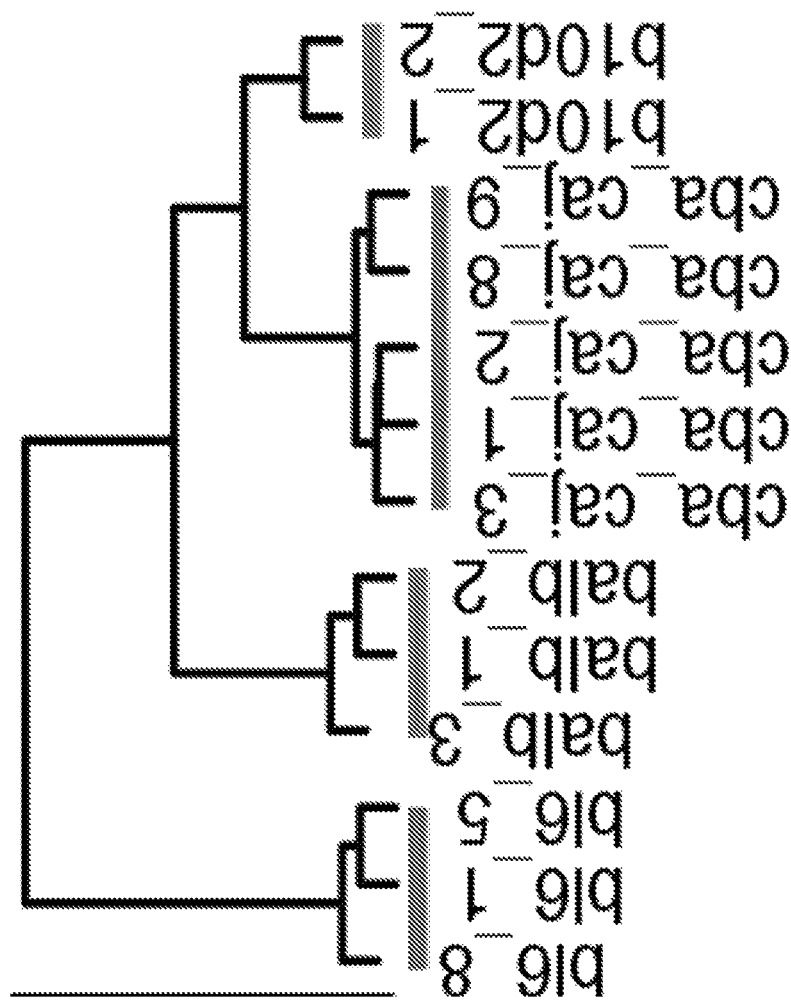
FIG. 13: Clustering based on V-J beta combinations across mice from four different strains (Black6, Balb, CBA/CAJ and B10D2). Spearman rank correlation is used to infer distances between any two strains using the frequencies of the V-J combinations. The strains cluster together (colored bars mark each of the four strains) implying the repertoire is shared among mice within a strain.

The V-J combinations can also be used to cluster the samples into phylogenetic trees (FIG. 13), using Spearman rank correlation. The mice cluster according to strain, suggesting strain-specific TCR repertoire signatures. It will be interesting to see how the clustering holds up under various strong perturbations, such as infections.

Analyses of CDR3s.

CDR3 sequences provide a means of more richly characterizing the TCR repertoire. By generating the amino-acid sequences for the CDR3 we can see that multiple CDR3 result in the same amino-acid sequence (FIG. 14).

Figure 14:
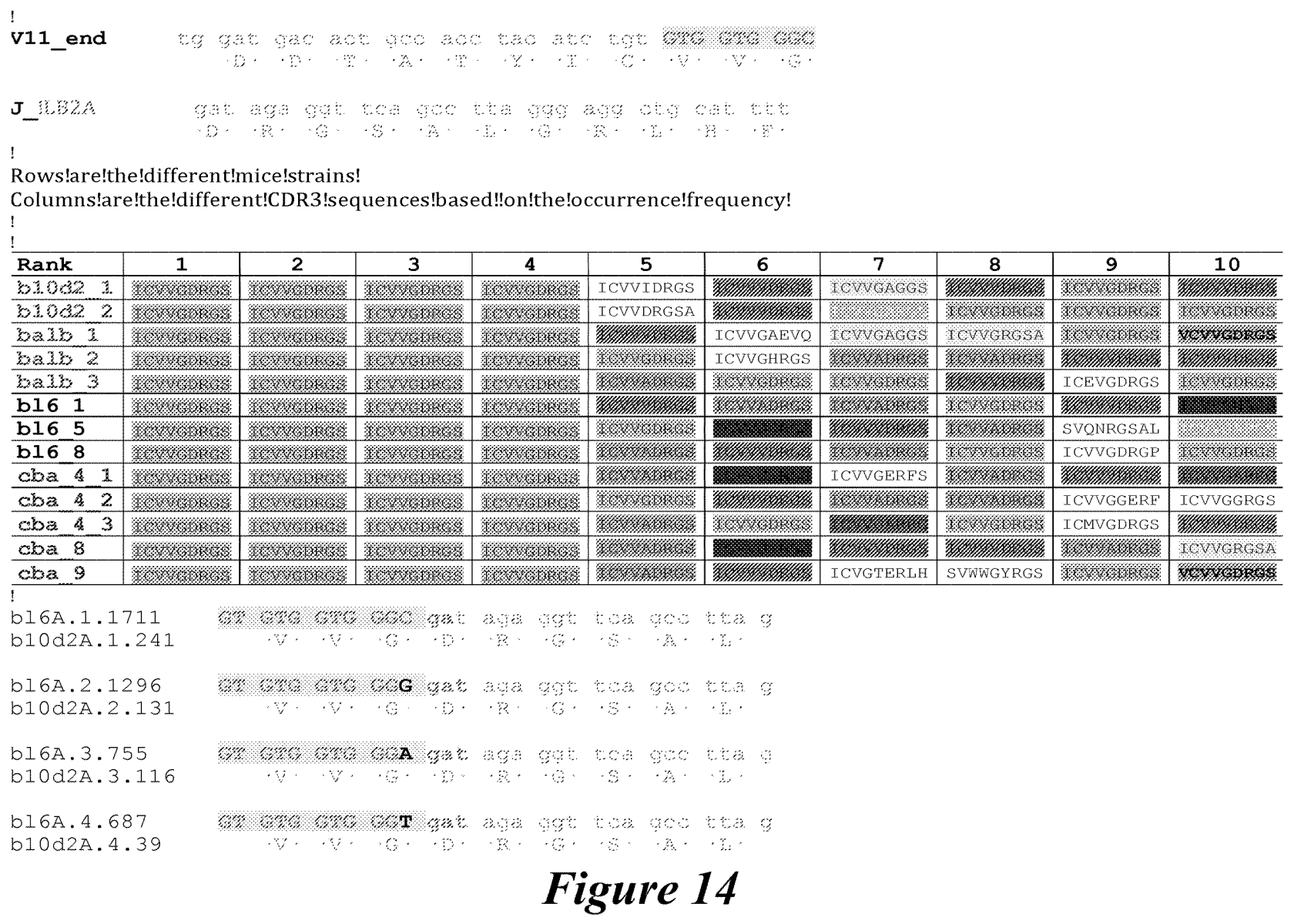

From FIG. 14 it can be seen that for a particular VJ combination the dominant amino-acid sequences are the same across strains. What is surprising is the lack of diversity at the amino-acid level, even though we expected a large number of mutations. It is possible that this may change under infection or some other perturbation of the TCR repertoire.

Figure 15:
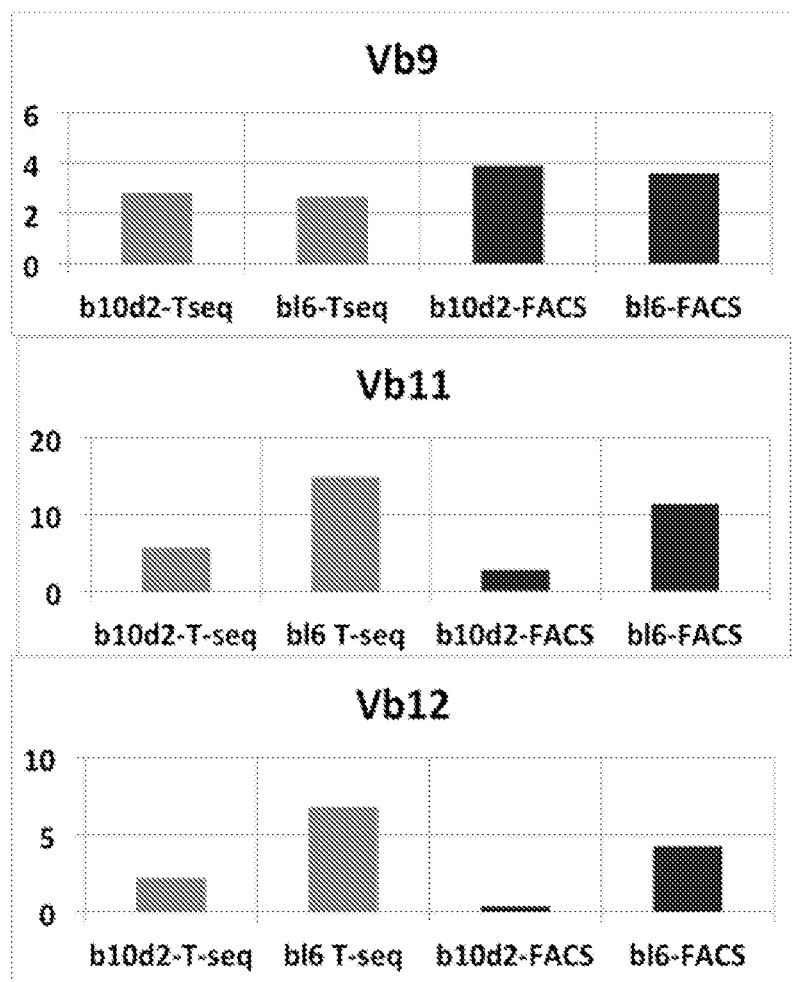
FIG. 15: Protein (FACS) and mRNA (T-seq) comparison for three V-segments (Vb9, Vb11, Vb12) in two mice strains, black-6 (b16) and b10d2. The blue bars are expression levels inferred from T-seq while the red bars are measurements of the number of cells stained by antibodies against the same segments using FACS. The protein and mRNA track each other in both b10d2 and b16.

Comparison of FACS and T-Seq:

To understand how accurate and reliable this approach was (both experimental and analytical) to measure the T cell receptor repertoire, the "gold standard" approach in the field, the use of Flow Cytometry that allows one to capture the measurements of proteins at a single cell resolution, was employed for comparison. To do this, spleens were taken from two strains of mice, black-6 (b16) and b10d2. Single cell suspensions were made and half of this was used for RNA isolation and T-seq. The other half of the single cell suspension was stained with a mix of three V-beta antibodies. There was concordance between the FACS and T-seq data (FIG. 15).

The data in the present example is the first explicit demonstration of concordance between TCR repertoire measurements using proteomic (FACS based on V-antibodies) evidence and TCR repertoire measurements based on mRNA (T-seq). This data suggests that TCR repertoire profiling through mRNA was robust and reliable.

Figure 16:
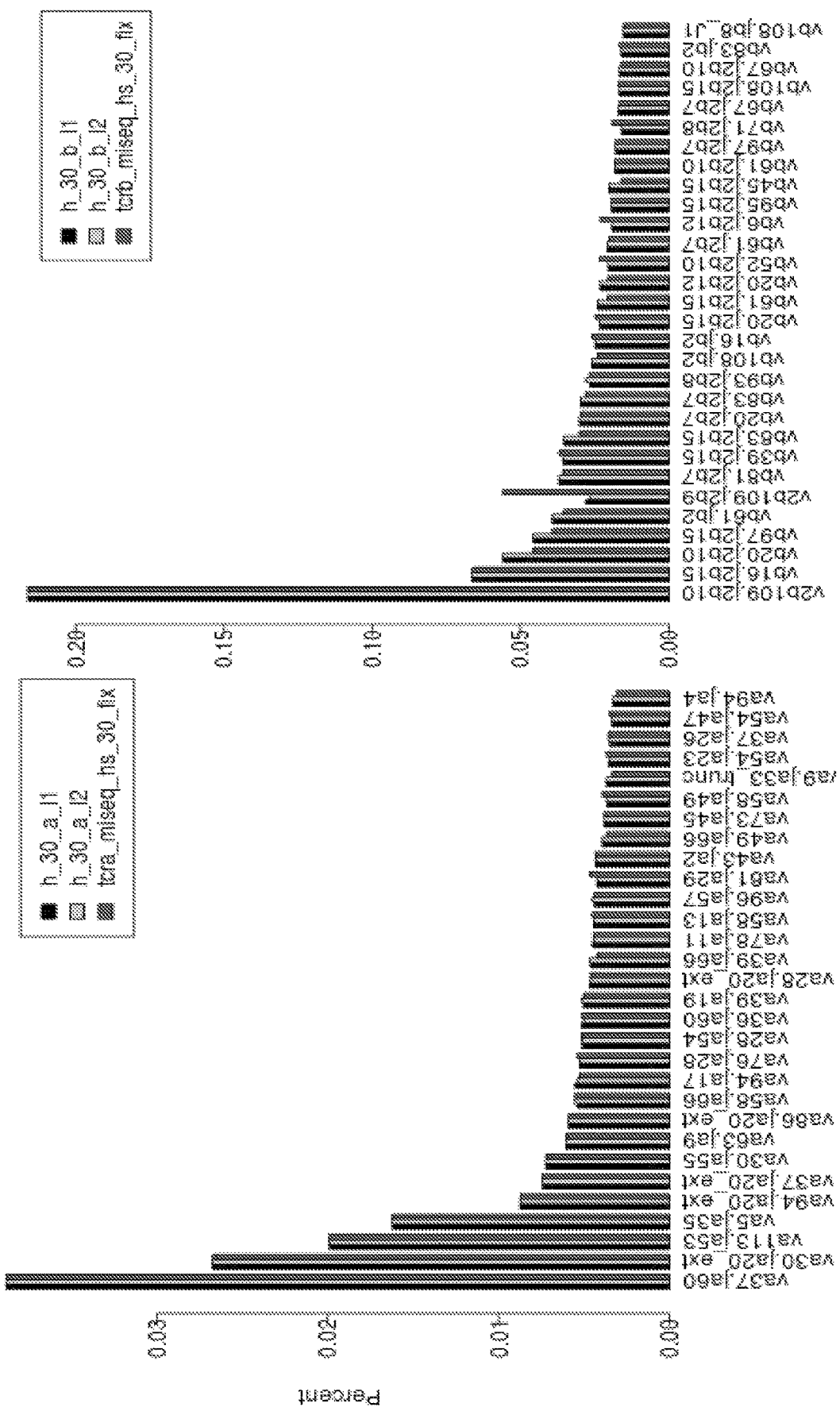
FIG. 16: Distribution of V,J combinations for α (left panel) and β (right panel) in one human, using two lanes of HiSeq (60 million reads each) and one lane of miseq (5 million reads). We show here only the top 30 combinations. The sequencing depth did not make a difference, but for combinations with low abundance, the depth did matter. It is not clear at this point if this would matter in practical clinical applications.

Characterizing the TCR Repertoire in Humans:

T-seq was applied to PBMC samples from four anonymous humans in order to understand the variability and usage of TCR in humans. The α and β repertoire from one human PBMC were seqeuenced, using a Miseq and a Hiseq. Data is shown in FIG. 16, and it was concluded from this data that the Miseq data at much lower depth and cost essentially captured the diversity of V and J, but combinations with low abundance obviously had more noise. The relevance of the low abundance combinations is yet to be determined.

Next, the four human PBMC samples were sequenced on a Hiseq. There was a lot of variability between humans (FIG. 17), suggesting that either the repertoire is very dynamic, or there are strong differences between humans. This requires further study, through a time-course measurement, as well as a longitudinal study across humans.

Figure 18:
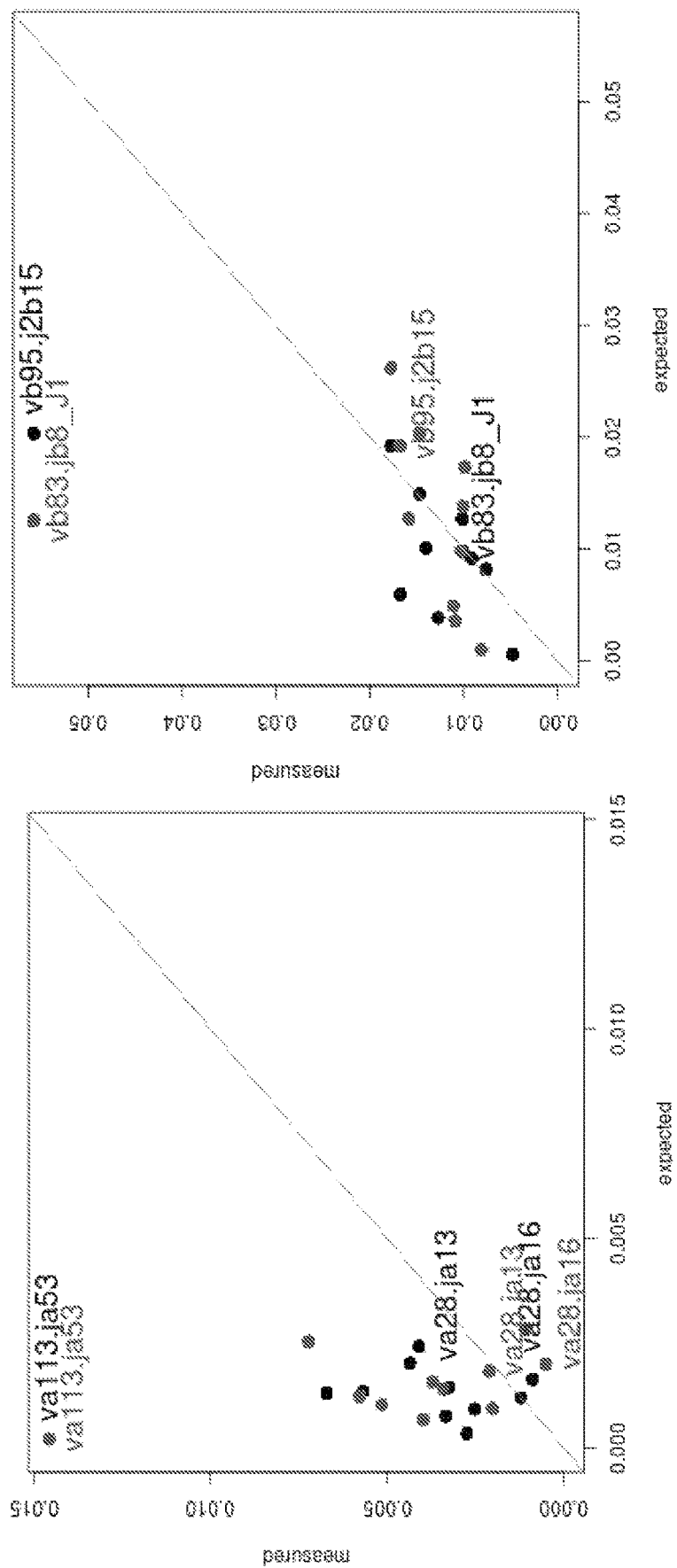
FIG. 18: Expected (x-axis) versus actual counts (y-axis) for different combinations of V and J in alpha (left) and beta (right). The red and black represent two different humans. We are showing a few data points, for ease of visualization. Each point is a combination, and the axes are frequencies. They should all lie on the diagonal; we show a few spots that deviate quite a bit. The red and black are data from two different humans. Surprisingly, in alpha, the most deviant combination is identical between humans, while in beta, they are two different combinations.

Based on the frequencies of V and J segment usage, the expected frequencies for various combinations were calculated. We found a few combinations with great deviations from the expected values (FIG. 18). There seemed to be differences between humans, but we did find some coincidences in the α combinations, suggesting the frequencies could have multiple causes, an inherent strength and some environmental contribution, which can contribute to differences between humans.

One approach to characterize the data is to use information theoretic measures, such as entropy (Mora et al., 2010). This approach has also been used in the analysis of texts, such as the zipfian analysis of the power laws exhibited by word frequencies (Situngkir, 2007) or in the analysis of a variety of economic, physical and social phenomena (Newman, 2004). Entropy characterizes the distribution of VJ (or VDJ) using a single number, $$E = -\Sigma_i p_i \log_2 p_i$$

where $p_i$ is the fraction of the population in species "i", the log is in base 2, and E is in bits. A larger number of species results in a bigger entropy, as does a less "peaked" distribution. Low entropy implies low diversity and dominance by a few species. Studying this under perturbations (vaccines, infections, auto-immunity) can provide a window into the overall structure of the recombination events.

Figure 19:
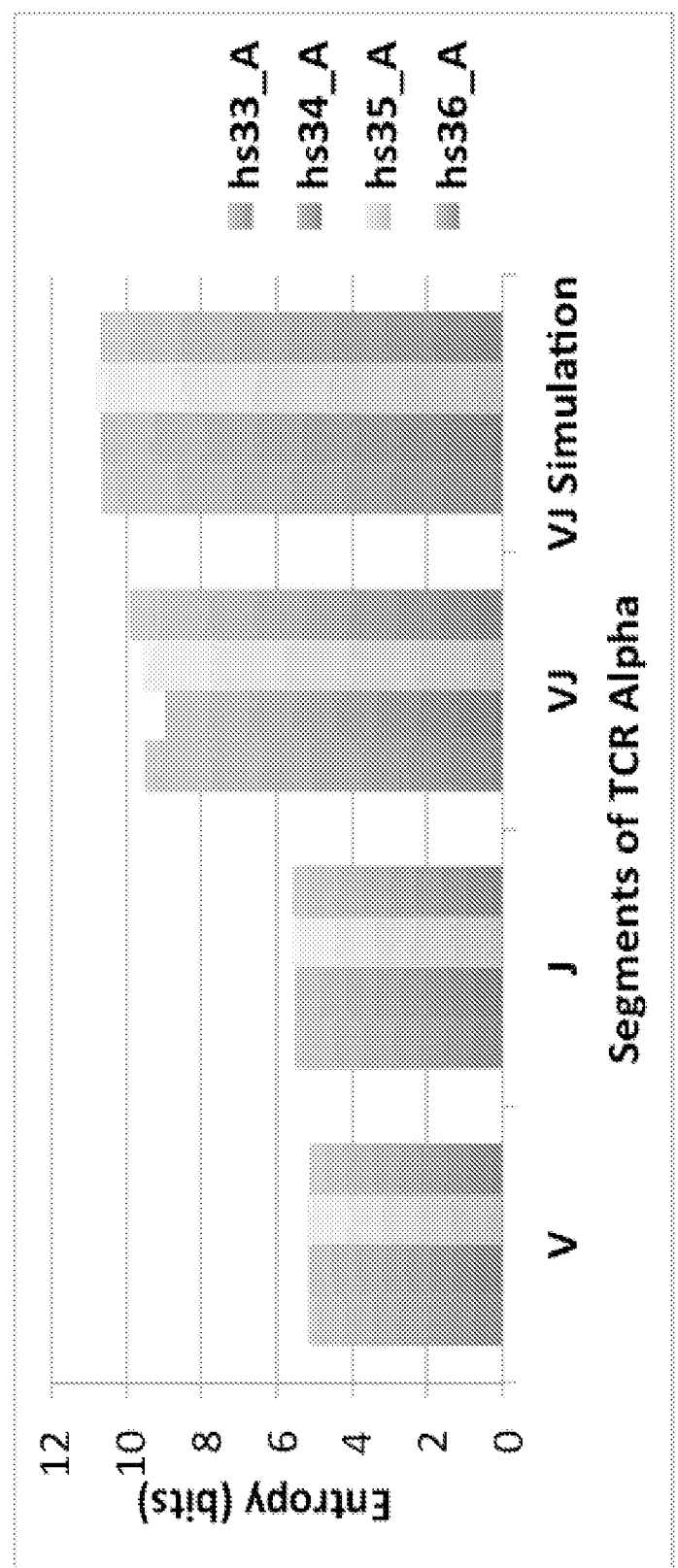
FIG. 19: Entropy of the distribution of alpha segments in four different human T cells taken from blood. The four humans are hs33, hs34, hs35 and hs36 as shown in the legend. The entropy for the different segments between different humans is surprisingly similar; despite the differences we see in the distribution of the individual segments (FIG. 17). There is higher entropy in the distribution of J segments, compared to the V, likely due to the larger number of J's. The VJ combinations are more restricted, have lower entropy, than the expected distribution of VJ combinations (VJ simulation).

The entropy was calculated for V, J and VJ combinations for TCR alpha and beta sequences. The VJ sim is the distribution of VJ combinations expected for the frequencies of V and J, if they were to independently associate with each other. For the alpha, V has lower entropy compared to J, which is expected since there are many more J's. The entropy of VJ sim was higher than the actual VJ suggesting that not all combinations are equal and some get favored (or suppressed) over others FIG. 19.

Figure 20:
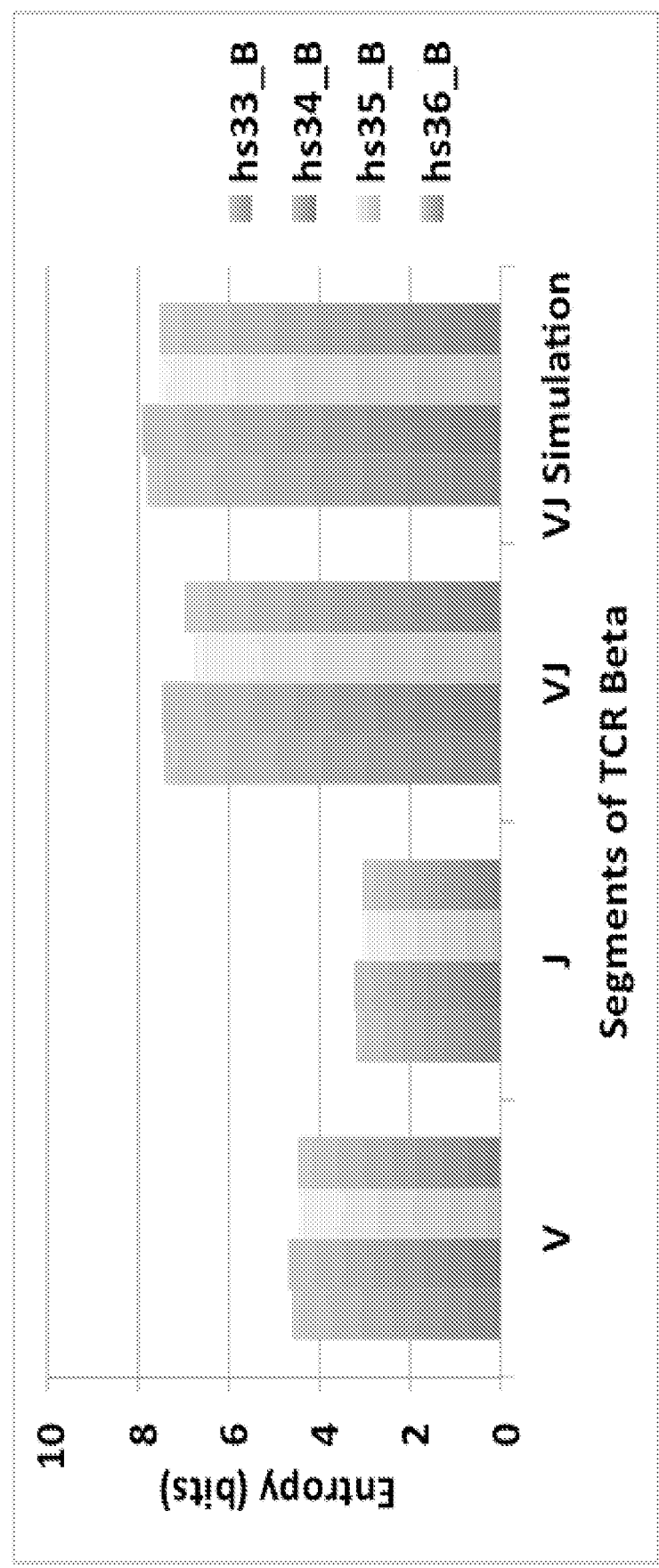
FIG. 20: Entropy of the distribution of the beta segments in four different human T cells taken from blood is shown. The four humans are hs33, hs34, hs35 and hs36 as shown in the legend. The entropy for the different segments between different humans is surprisingly similar as in the case of alpha; despite the differences we see in the distribution of individual segments (FIG. 17). There is higher entropy in the distribution of V segments, compared to the J, likely due to the larger number of V's. The VJ combinations are more restricted, have lower entropy, than the expected distribution of VJ combinations (VJ simulation).

In the case of beta, the entropy of V was greater than J in all the four human samples sequenced, which is also expected, since the J's are fewer in number. Again the entropy of VJsim was higher than the entropy of VJ, which suggests certain combinations are favored (or suppressed) compared to others (FIG. 20).

Conclusion

The above example describes a detailed a powerful approach to TCR-repertoire profiling and showed results that show the promise of the method and the opportunities that will arise from this. From the analysis, few novel elements with EST support for them were identified. A few cases where alternate transcripts require the boundaries of the segments to be extended were also identified. For example, in the β in mouse we occasionally find an extension (72 nt long) to the C1 on the 5' end, which has been noticed in the literature before, but is not present in recent genomic surveys (Behlke and Loh, 1986) (FIG. 9) This is an extra sequence that is independent of the J preceding the C.

Figure 11:
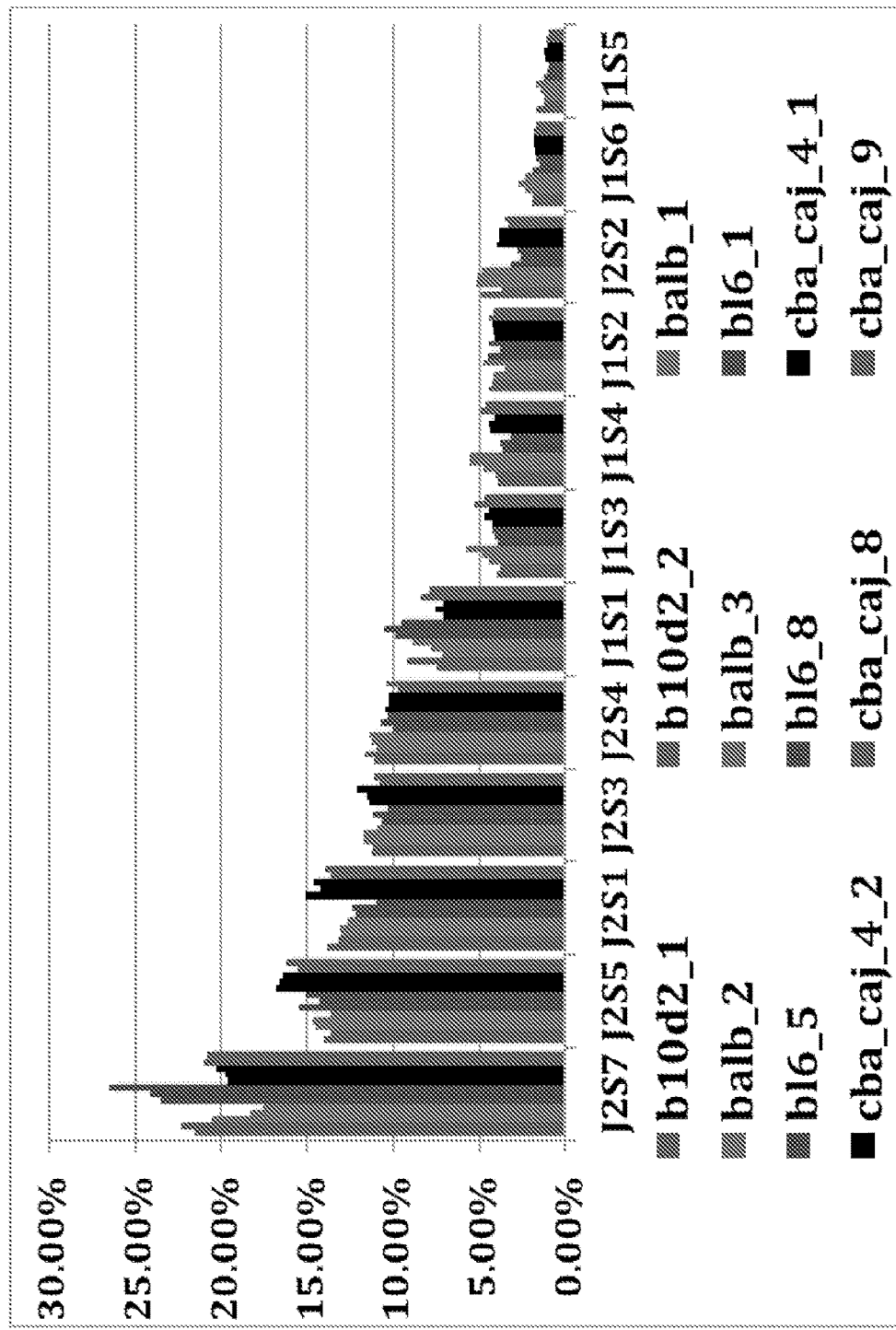
FIG. 11: Usage of J β in four mice strains. The J2s are used more than the J1s, and one J2 is not expressed at all. There is no difference in the J usage between these mice strain even though the usage of J segments is biased.

The spectrum of usage of the various V and J elements in the β chain can also be obtained. The β J's are shown in FIG. 11 suggesting a strong bias for certain J's, the J2 group was used more than the J1 group, under quiescent conditions (when the immune system has not been perturbed), which could potentially arise from differing strengths of the RSSs in the genome (Nadel et al., 1998a, 1998b). Several novel segments and recombination events (FIGS. 9, 10) were also identified. It is expected that TCR signatures will enable prediction of outcomes (prognosis) and help tailor treatments in various disorders, especially in auto-immunity. Long-term, the identification of features in the TCR repertoire to lead to personalized treatments with antigens targeting specific parts of the repertoire is expected.

References

1. Allison, J. P., McIntyre, B. W., and Bloch, D. (1982). Tumor-specific antigen of murine T-lymphoma defined with monoclonal antibody. J. Immunol. Baltim. Md. 1950 129, 2293-2300.
2. Arber, W. (1974). DNA modification and restriction. Prog. Nucleic Acid Res. Mol. Biol. 14, 1-37.
3. Arden, B., Clark, S. P., Kabelitz, D., and Mak, T. W. (1995). Mouse T-cell receptor variable gene segment families. Immunogenetics 42, 501-530.
4. Behlke, M. A., and Loh, D. Y. (1986). Alternative splicing of murine T-cell receptor beta-chain transcripts. Nature 322, 379-382.
5. Benichou, J., Ben-Hamo, R., Louzoun, Y., and Efroni, S. (2012). Rep-Seq: uncovering the immunological repertoire through next-generation sequencing. Immunology 135, 183-191.
6. Boudinot, P., Marriotti-Ferrandiz, M. E., Pasquier, L. D., Benmansour, A., Cazenave, P.-A., and Six, A. (2008). New perspectives for large-scale repertoire analysis of immune receptors. Mol. Immunol. 45, 2437-2445.
7. Boyd, S. D., Marshall, E. L., Merker, J. D., Maniar, J. M., Zhang, L. N., Sahaf, B., Jones, C. D., Simen, B. B., Hanczaruk, B., Nguyen, K. D., et al. (2009). Measurement and Clinical Monitoring of Human Lymphocyte Clonality by Massively Parallel V-D-J Pyrosequencing. Sci. Transl. Med. 1, 12ra23-12ra23.
8. Caccia, N., Kronenberg, M., Saxe, D., Haars, R., Bruns, G. A., Goverman, J., Malissen, M., Willard, H., Yoshikai, Y., and Simon, M. (1984). The T cell receptor beta chain genes are located on chromosome 6 in mice and chromosome 7 in humans. Cell 37, 1091-1099.
9. Casrouge, A., Beaudoing, E., Dalle, S., Pannetier, C., Kanellopoulos, J., and Kourilsky, P. (2000). Size estimate of the alpha beta TCR repertoire of naive mouse splenocytes. J. Immunol. Baltim. Md. 1950 164, 5782-5787.
10. Charles A Janeway, J., Travers, P., Walport, M., and Shlomchik, M. J. (2001). The components of the immune system.
11. Dembić, Z., Haas, W., Weiss, S., McCubrey, J., Kiefer, H., von Boehmer, H., and Steinmetz, M. (1986). Transfer of specificity by murine alpha and beta T-cell receptor genes. Nature 320, 232-238.
12. Doherty, P. C., Riberdy, J. M., and Belz, G. T. (2000). Quantitative analysis of the CD8+ T-cell response to readily eliminated and persistent viruses. Philos. Trans. R. Soc. Lond. B. Biol. Sci. 355, 1093-1101.
13. Faint, J. M., Pilling, D., Akbar, A. N., Kitas, G. D., Bacon, P. A., and Salmon, M. (1999). Quantitative flow cytometry for the analysis of T cell receptor Vbeta chain expression. J. Immunol. Methods 225, 53-60.

14. Frankel, W. N., Rudy, C., Coffin, J. M., and Huber, B. T. (1991). Linkage of Mls genes to endogenous mammary tumour viruses of inbred mice. Nature 349, 526-528.
15. Freeman, J. D., Warren, R. L., Webb, J. R., Nelson, B. H., and Holt, R. A. (2009). Profiling the T-cell receptor beta-chain repertoire by massively parallel sequencing. Genome Res. 19, 1817-1824.
16. Gotoh, O. (1982). An improved algorithm for matching biological sequences. J. Mol. Biol. 162, 705-708.
17. Haqqi, T. M., Banerjee, S., Jones, W. L., Anderson, G., Behlke, M. A., Loh, D. Y., Luthra, H. S., and David, C. S. (1989). Identification of T-cell receptor V beta deletion mutant mouse strain AU/ssJ (H-2q) which is resistant to collagen-induced arthritis. Immunogenetics 29, 180-185.
18. Hedrick, S. M., Cohen, D. I., Nielsen, E. A., and Davis, M. M. (1984). Isolation of cDNA clones encoding T cell-specific membrane-associated proteins. Nature 308, 149-153.
19. Hozumi, N., and Tonegawa, S. (1976). Evidence for somatic rearrangement of immunoglobulin genes coding for variable and constant regions. Proc. Natl. Acad. Sci. U.S.A 73, 3628-3632.
20. Hsu, E. (2011). The invention of lymphocytes. Curr. Opin. Immunol. 23, 156-162.
21. Jensenius, J. C., and Williams, A. F. (1982). The T lymphocyte antigen receptor—paradigm lost. Nature 300, 583-588.
22. Klenerman, P., Cerundolo, V., and Dunbar, P. R. (2002). Tracking T cells with tetramers: new tales from new tools. Nat. Rev. Immunol. 2, 263-272.
23. Kronenberg, M., Kraig, E., and Hood, L. (1983). Finding the T-cell antigen receptor: past attempts and future promise. Cell 34, 327-329.
24. Ladi, E., Yin, X., Chtanova, T., and Robey, E. A. (2006). Thymic microenvironments for T cell differentiation and selection. Nat. Immunol. 7, 338-343.
25. Lane, J., Duroux, P., and Lefranc, M.-P. (2010). From IMGT-ONTOLOGY to IMGT/LIGMotif: the IMGT standardized approach for immunoglobulin and T cell receptor gene identification and description in large genomic sequences. BMC Bioinformatics 11, 223.
26. Lefranc, M.-P., Giudicelli, V., Ginestoux, C., Jabado-Michaloud, J., Folch, G., Bellahcene, F., Wu, Y., Gemrot, E., Brochet, X., Lane, J., et al. (2009). IMGT, the international ImMunoGeneTics information system. Nucleic Acids Res. 37, D1006-D1012.
27. Mak, T. W. (2007). The T cell antigen receptor: "The Hunting of the Snark." Eur. J. Immunol. 37, S83-S93.
28. Mazer, B. D., Renz, H., and Gelfand, E. W. (1991). An ELISA spot assay for quantitation of human immunoglobulin-secreting cells. J. Allergy Clin. Immunol. 88, 235-243.
29. Medzhitov, R. (2009). Approaching the asymptote: 20 years later Immunity 30, 766-775.
30. Michie, A. M., and Zúñiga-Pflücker, J. C. (2002). Regulation of thymocyte differentiation: pre-TCR signals and beta-selection. Semin. Immunol. 14, 311-323.
31. Miller, J. F. a. P. (2004). Events that led to the discovery of T-cell development and function—a personal recollection. Tissue Antigens 63, 509-517.
32. Mora, T., Walczak, A. M., Bialek, W., and Callan, C. G., Jr (2010). Maximum entropy models for antibody diversity. Proc. Natl. Acad. Sci. U.S.A 107, 5405-5410.
33. Nadel, B., Tang, A., Escuro, G., Lugo, G., and Feeney, A. J. (1998a). Sequence of the spacer in the recombination signal sequence affects V(D)J rearrangement frequency and correlates with nonrandom Vkappa usage in vivo. J. Exp. Med. 187, 1495-1503.
34. Nadel, B., Tang, A., Lugo, G., Love, V., Escuro, G., and Feeney, A. J. (1998b). Decreased frequency of rearrangement due to the synergistic effect of nucleotide changes in the heptamer and nonamer of the recombination signal sequence of the V kappa gene A2b, which is associated with increased susceptibility of Navajos to *Haemophilus influenzae* type b disease. J. Immunol. Baltim. Md. 1950 161, 6068-6073.
35. Nanda, N. K., Apple, R., and Sercarz, E. (1991). Limitations in plasticity of the T-cell receptor repertoire. Proc. Natl. Acad. Sci. U.S.A 88, 9503-9507.
36. Newman, M. E. J. (2004). Power laws, Pareto distributions and Zipf's law. ArXivcond-Mat0412004.
37. Nikolich-Zugich, J., Slifka, M. K., and Messaoudi, I. (2004). The many important facets of T-cell repertoire diversity. Nat. Rev. Immunol. 4, 123-132.
38. Rezuke, W. N., Abernathy, E. C., and Tsongalis, G. J. (1997). Molecular diagnosis of B- and T-cell lymphomas: fundamental principles and clinical applications. Clin. Chem. 43, 1814-1823.
39. Rock, E. P., Sibbald, P. R., Davis, M. M., and Chien, Y. H. (1994). CDR3 length in antigen-specific immune receptors. J. Exp. Med. 179, 323-328.
40. Schatz, D. G., and Ji, Y. (2011). Recombination centres and the orchestration of V(D)J recombination. Nat. Rev. Immunol. 11, 251-263.
41. Schluter, S. F., Bernstein, R. M., Bernstein, H., and Marchalonis, J. J. (1999). "Big Bang" emergence of the combinatorial immune system. Dev. Comp. Immunol. 23, 107-111.
42. Sha, W. C., Nelson, C. A., Newberry, R. D., Kranz, D. M., Russell, J. H., and Loh, D. Y. (1988). Positive and negative selection of an antigen receptor on T cells in transgenic mice. Nature 336, 73-76.
43. Situngkir, H. (2007). An Observational Framework to the Zipfian Analysis among Different Languages: Studies to Indonesian Ethnic Biblical Texts.
44. Slansky, J. E. (2011). TCR-sequences.
45. Snodgrass, H. R., Kisielow, P., Kiefer, M., Steinmetz, M., and von Boehmer, H. (1985). Ontogeny of the T-cell antigen receptor within the thymus. Nature 313, 592-595.
46. Wang, C., Sanders, C. M., Yang, Q., Schroeder, H. W., Wang, E., Babrzadeh, F., Gharizadeh, B., Myers, R. M., Hudson, J. R., Davis, R. W., et al. (2010). High throughput sequencing reveals a complex pattern of dynamic interrelationships among human T cell subsets. Proc. Natl. Acad. Sci. U.S.A 107, 1518-1523.
47. Warren, R. L., Freeman, J. D., Zeng, T., Choe, G., Munro, S., Moore, R., Webb, J. R., and Holt, R. A. (2011). Exhaustive T-cell repertoire sequencing of human peripheral blood samples reveals signatures of antigen selection and a directly measured repertoire size of at least 1 million clonotypes. Genome Res. 21, 790-797.
48. Weinstein, J. A., Jiang, N., White, R. A., 3rd, Fisher, D. S., and Quake, S. R. (2009). High-throughput sequencing of the zebrafish antibody repertoire. Science 324, 807-810.
49. Williams, A. F. (1984). The T-lymphocyte antigen receptor—elusive no more. Nature 308, 108-109.
50. Yanagi, Y., Yoshikai, Y., Leggett, K., Clark, S. P., Aleksander, I., and Mak, T. W. (1984). A human T cell-specific cDNA clone encodes a protein having extensive homology to immunoglobulin chains. Nature 308, 145-149.

51. Yashiro-Ohtani, Y., Ohtani, T., and Pear, W. S. (2010). Notch regulation of early thymocyte development. Semin. Immunol. 22, 261-269.

52. Zinkernagel, R. M., and Doherty, P. C. (1974). Restriction of in vitro T cell-mediated cytotoxicity in lymphocytic choriomeningitis within a syngeneic or semiallogeneic system. Nature 248, 701-702.

Example 2: The Role of the TCR-Repertoire in Graves' Disease

Graves' Disease as a Model of Autoimmunity:

Graves' disease is characterized by hyperthyroid activity. This is caused by the immune system making antibodies that act like the thyroid-stimulating hormone (TSH), which is usually made by the pituitary gland, causing the thyroid to synthesize and secrete thyroid hormone. Graves' disease is an ideal platform for research into autoimmune disorders, due to availability of normal thyroids and thyroid samples from patients with Graves' disease.

Overall Rationale:

Graves' disease is an autoimmune disease with a large number of known susceptibility genes [36]-[38], involvement of both T cells [39], [40] and B cells [41], which results in the production of autoantibodies to the TSH receptor. The Davies laboratory has been working on the role of TCRR in Graves' disease for over 20 years, accumulating evidence for differences in the TCRR between thyroids from patients and controls [42]-[50]. mRNA-seq data generated by us characterizes the autoimmune response pathways, which play a key role in the chronic stage of the disease, suggesting that the TCRR will be an important source of information regarding the course of the disease and the prognosis. Based on this, we hypothesize that the TCRR in Graves' disease thyroid samples will have signatures specific to the disease and will show changes over the course of treatment. We expect to see signs of this signature in the PBMC derived TCRR, which would allow less invasive monitoring of the treatments effect on the thyroid. In addition, the TCRR might suggest targets for therapeutic intervention by allowing development of antigen specific interactions with components of the TCRR responsible for the progression of the disease.

Methods

Sample Collection:

Thyroid samples from patients and controls will be collected as part of standard clinical practice, independent of this study. Normal and Graves' thyroid tissue (n=100) will be used from thyroidectomy specimens obtained from the Mount Sinai Bio depository. Graves' disease will be defined, for this study, as a history of biochemical hyperthyroidism, a diffuse goiter, and either a normal or increased 24 hour radioactive iodine update and/or the presence of TSH receptor antibodies (TSHR-Ab). Normal tissue will be collected from patients having thyroid surgery for benign nodules.

Sample Processing:

The processing of the samples will follow protocols already established in the mRNA-seq study. T-seq will be applied to these samples and PBMCs from the patients as specified in Example 1.

Analysis:

The analytical tools described in Example 1 will be utilized to derive signatures in the TCRR derived from the thyroid tissues and PBMCs. Features in the TCRR that are differentially expressed in the diseased cases compared to the controls will be identified. The TCRR profiles derived from PBMCs and thyroid tissues to identify correlations (or anti-correlations) in signatures will be compared.

Figure 21:
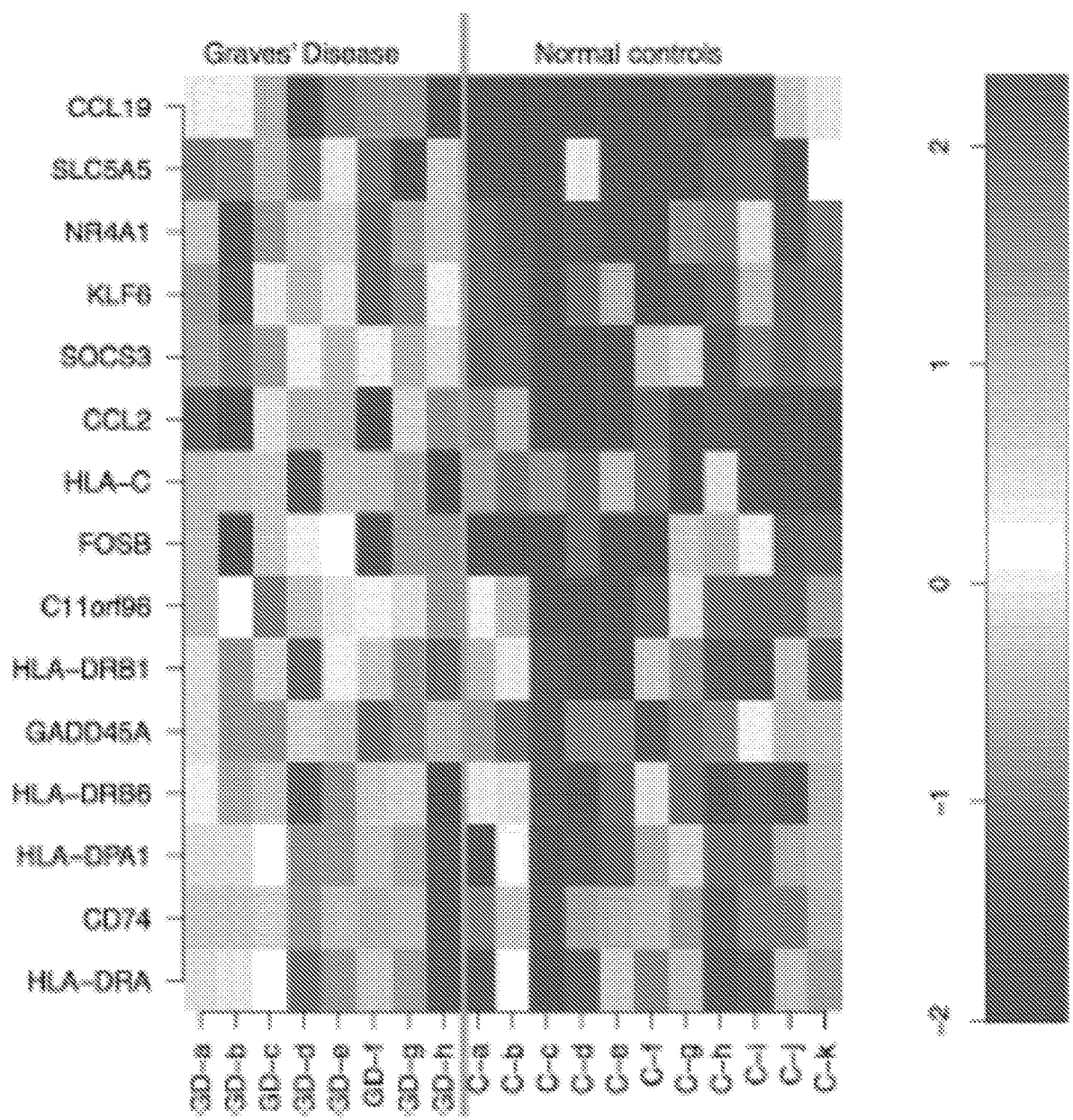
FIG. 21: Graves' Disease signature derived from mRNA-SEq on thyroid tissue from 9 patients with Graves' Disease subjected to total thyroidectomy and compared the data with 12 samples of normal thyroid tissue obtained from patients having a thyroid nodule removed. Red indicates increased expression and blue indicates decreased expression.

Preliminary Data:

On comparison of expression levels in tissues derived from Graves' patients and controls, there was clear evidence for over-expression of the antigen presentation pathway consisting of HLA and associated genes (FIG. 21). A robust disease signature and discovered active innate and adaptive immune signaling networks were also found. These data revealed an active immune defense system in Graves' disease, which involved novel molecular mechanisms in its pathogenesis and development.

Expected Results:

The TCRR profile for thyroid tissue from patients is expected to show signatures of the treatment and disease progression. The TCRR from PBMCs could have signatures of T cell recruitment to the thyroid tissue, either as a depletion in the PBMC derived TCRR or as a "spillover" from the excess in thyroid tissues. The signatures are expected to enable prediction of outcomes (prognosis) and help tailor treatments. The identification of features in the TCRR are expected to lead to personalized treatments with antigens targeting specific parts of the repertoire.

Example 3: Detailed TCR Protocol

Figure 22:
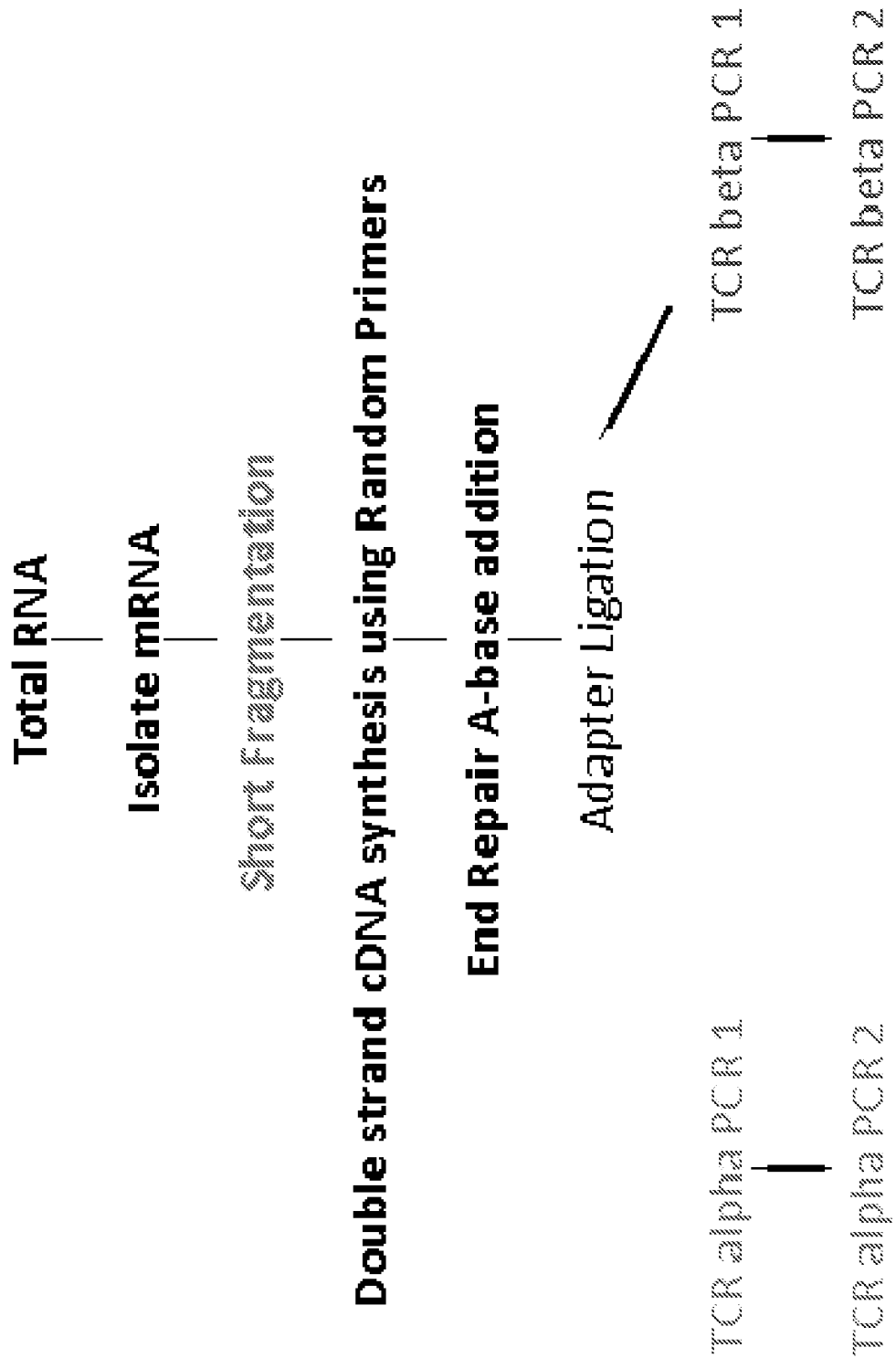
FIG. 22: Schematic diagram of T-cell receptor repertoire (TCRR) generation protocol.
Figure 24:
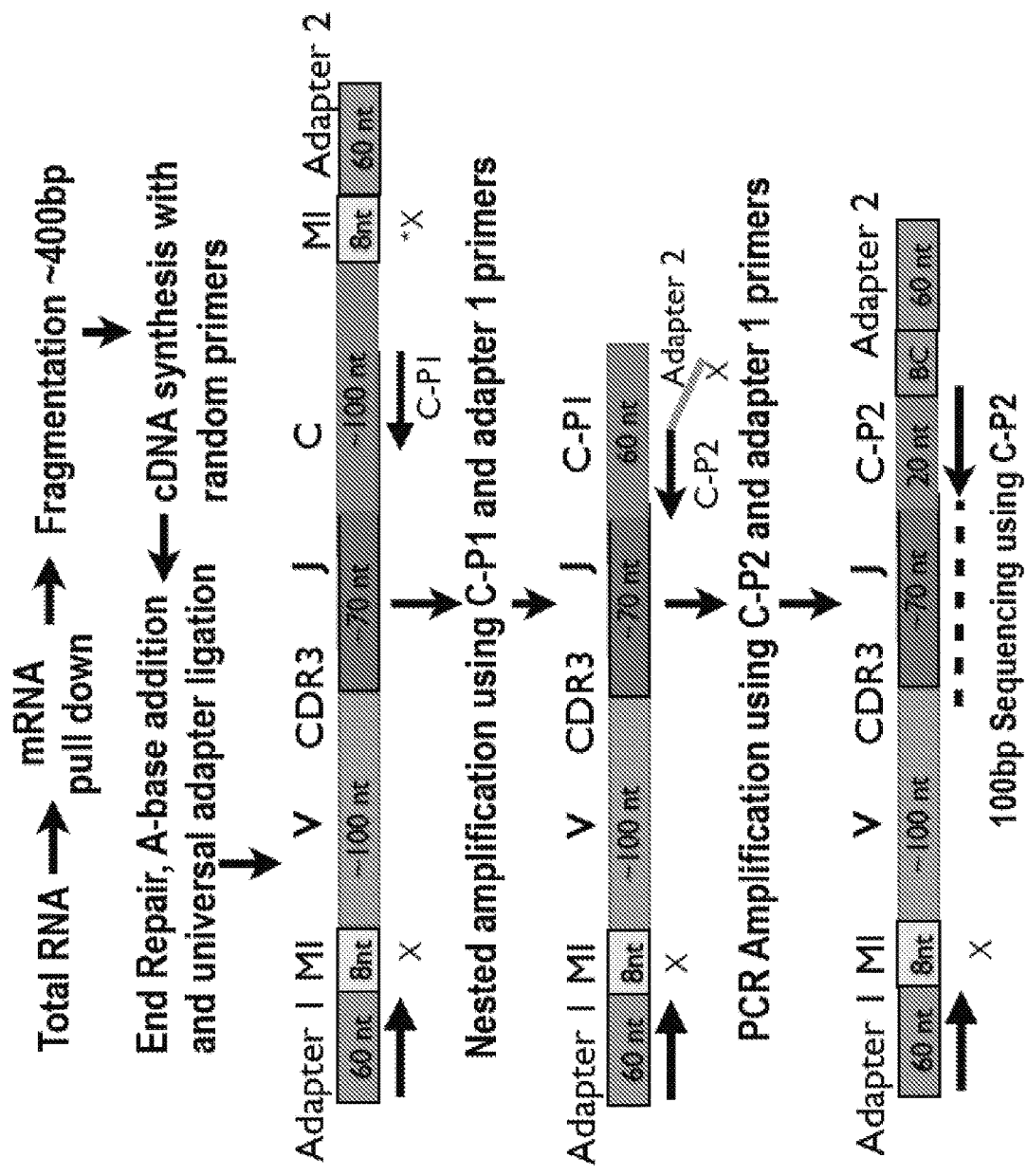
FIG. 24: Illustration of the T-seq protocol integrating indexing (MI) and bar code (BC) sequences, in accordance with one implementation.

Outline, see FIG. 22.

Reagents used:

Reagents for Fragmentation, first strand, second strand, end repair, A-base addition, adapter ligation (Illumina, TruSeq™ RNA Sample Prep Kit v2-Set A, RS-122-2001)

Ampure beads (Beckman coulter, Agencourt, AMPure XP-PCR Purification, Item No. A63880)

Primers for PCR 1 and 2 (self designed and synthesized by IDT)

TCR Protocol (Steps 1-82 are the Same for any Species)

Poly A select mRNA.

1. Mix 500 ng total RNA and H O to a final volume of 16.67 µl.
2. Vortex RNA Purification Beads and add 16.67 µl to RNA sample.
3. Mix by pipeting up and down until beads are in a homogenous suspension.
4. Incubate in thermocycler:
   65° C.—5 min
   4 C—hold
5. When thermo cycler reaches 4° C. remove sample and place on bench at room temperature for 5 min.
6. Place sample in magnetic rack for 5 min.
7. Remove and discard all the supernatant.
8. Remover sample from rack.
9. Add 66.7 µl of Bead Washing Buffer and pipet up and down until beads are in a homogenous suspension
10. Place the sample back in the magnetic rack for 5 min.
11. Remove and discard all the supernatant.
12. Add 16.67 µl of Elution Buffer and pipet up and down until beads are in a homogenous suspension
13. Incubate in thermocycler:
    80° C.—2 min
    25° C.—hold
14. Remove sample from thermocycler when it reaches 25° C. and keep at room temp.
15. Add 16.67 µl of Bead Binding Buffer and pipet up and down until beads are in a homogenous suspension.
16. Incubate at room temperature for 5 min.
17. Place sample in magnetic separator for 5 min.

18. Remove and discard all supernatant.
19. Remove sample from rack.
20. Add 66.7 μl of Bead Washing Buffer and pipet up and down until beads are in a homogenous suspension.
21. Place sample in magnetic separator for 5 min.
22. Remove and discard all supernatant.
23. Add 6.5 μl Elute, Prime, Fragment Mix and pipet up and down until beads are in a homogenous suspension.
24. Incubate in thermocycler:
    94° C.—4 min
    4° C.—hold
25. Place sample in magnetic rack for 5 min.
26. Transfer 5.67 μl of the supernatant to a new 0.2 ml PCR tube.
    First Strand Synthesis.
27. Add 2.67 μl First Strand Mast Mix/Super Script II mix to sample.
28. Incubate in thermocycler:
    25° C.—0 min°
    42° C.—50 min°
    70° C.—15 min
    4° C.—hold
    Second Strand Synthesis
29. Add 8.33 μl of Second Strand Master Mix to sample.
30. Incubate in thermocycler at 16 C for 1 hour.
31. Remove sample from thermocycler and let warm to room temperature
32. Add 30 μl of well-mixed AMPure XP beads and mix by pipetting up and down until beads are in a homogenous suspension (see note #5).
33. Incubate at room temperature for 15 min.
34. Place on magnetic rack for 5 min.
35. Remove and discard 45 μl of the supernatant.
36. Keep sample in magnetic rack and add 200 μl of 80% ethanol.
37. Incubate for 30 seconds. Remove and discard all supernatant.
38. Repeat step 36 and 37 once more for a total of two washes.
39. Add 22 μl Resuspension Buffer and pipet up and down until beads are in a homogenous suspension.
40. Incubate at room temperature for 5 min.
41. Place in magnetic rack for 5 min.
42. Transfer 20 μl of the supernatant to a new 0.2 ml PCR tube.
    Perform End Repair.
43. Add 13.3 μl of End Repair Mix to sample.
44. Incubate at 30° C. for 30 min.
45. Add 53.3 μl of well-mixed Ampure XP Beads and mix by pipetting up and down until beads are in a homogenous suspension.
46. Incubate at room temperature for 15 min.
47. Place on magnetic rack for 5 min.
48. Remove and discard 81.6 μl of the supernatant.
49. Keep sample in magnetic rack and add 200 μl of 80% ethanol.
50. Incubate for 30 seconds. Remove and discard all supernatant.
51. Repeat step 49 and 50 once more for a total of two washes.
52. Add 7.83 μl Resuspension Buffer and pipet up and down and mix by pipetting up and down until beads are in a homogenous suspension.
53. Incubate at room temperature for 5 min.
54. Place in magnetic rack for 5 min.
55. Transfer 5.83 μl of the supernatant to a new 0.2 ml PCR tube.
    Add 'A' bases to 3' ends.
56. Add 4.17 μl, A-trailing Mix to sample.
57. Incubate at 37° C. for 30 min.
    Ligate Adapters to DNA fragments.
58. Add: 0.83 μl DNA Ligase Mix
    0.83 μl Resuspension Buffer
    0.83 μl RNA Adapter Index
59. Incubate at 30° C. for 10 min.
60. Add 1.67 μl Stop Ligase Mix
61. Add 1.4 μl of well-mixed, AMPure XP beads and mix by pipetting up and down until beads are in a homogenous suspension.
62. Incubate at room temperature for 15 min.
63. Place on magnetic rack for at least 5 min.
64. Remove and discard 23.16 μl of the supernatant.
65. Keep sample in magnetic rack and add 200 μl of 80% ethanol.
66. Incubate for 30 seconds. Remove and discard all supernatant.
67. Repeat steps 65 and 66 one more time.
68. Add 18.67 μl Resuspension Buffer and pipet up and down and mix by pipetting up and down until beads are in a homogenous suspension.
69. Incubate at room temperature for 15 min.
70. Place in magnetic rack for at least 5 min.
71. Transfer 16.67 μl of the supernatant to a new 0.2 ml PCR tube.
72. Add 16.67 μl of well-mixed AMpure XP beads.
73. Incubate at room temperature for 15 min.
74. Place on magnetic rack for at least 5 min.
75. Remove and discard 28.34 μl of the supernatant.
76. Keep sample in magnetic rack and add 200 μl of the supernatant.
77. Incubate for 30 seconds. Remove and discard all supernatant.
78. Repeat steps 76 and 77 one more time.
79. Add 30 μl Resuspension Buffer and pipet up and down 10 times.
80. Incubate at room temperature for 5 min.
81. Place in magnetic rack for 5 min.
82. Collect the 30 μl supernatant in a new tube.
    Amplify TCR-alpha/beta library by PCR1.
83. Mix: 10.5 μl Adapter ligated DNA from step 82
    2 μl Primer mix 1
    12.5 μl PCR Mast Mix
84. Amplify with the following PCR protocol:
    a. 98° C. for 30 seconds
       98° C. for 10 seconds
       60° C. for 30 seconds
       72° C. for 30 seconds
    Repeat steps b to d for 10 cycles.
       72° C. for 5 min
85. Purify between the two PCR. Cast a 2% low melt agarose gel and run the entire per product for an hour at 100V. Cut bands from 250-600 bp.
86. Elute the DNA from the agarose slice using a qiagen column in a 30 μl volume.
87. Amplify TCR-alpha/beta library by PCR2
    Mix: 30 μl DNA from step 86
    2 μl Primer Mix 2
    30 μl PCR Master Mix 88. Amplify with the following PCR protocol:
    a. 98° ° C. for 30 seconds
    b. 98° ° C. for 10 seconds
    c. 60° ° C. for 30 seconds
    d. 72° ° C. for 30 seconds
    e. Repeat steps b to d for 10 cycles.
    f. 72° ° C. for 5 min
    g. Hold at 4° ° C.
89. Add 108 µl of well-mixed AMPure XP beads.
90. Incubate at room temperature for 15 min.
91. Place on magnetic rack for at least 5 min.
92. Remove and discard the supernatant.
93. Keep sample in magnetic rack and add 200 µl of 80% ethanol.
94. Incubate for 30 seconds. Remove and discard all supernatant.
95. Repeat steps 90 and 91 one more time.
96. Let the beads dry at room temperature for 2 min.
97. Add 15 µl Resuspension Buffer and pipet up and down 10 times.
98. Incubate at room temperature for 2 min.
99. Place in magnetic rack for 5 min.
100. Transfer 15 µl of the supernatant to a new 1.5 ml PCR tube.

The adapter sequences and constant regions used in the experiments in these examples are included in the list of primers below. For example, the forward primer is adapter 1 and the reverse primers contain both adapter 2 and constant regions of either the alpha or the beta TCR. Regarding annotation for the primer sequences below, the constant regions (C-regions) are bolded and underlined. In the reverse primers, anything after the box brackets ([ ]) is the constant region in bold and underlined, and anything before the brackets is the adapter sequence.

Primers Used to Isolate Alpha TCR Sequences in PCR 1 for Mouse:

```
F = universal adapter

AATGATACGGCGACCACCGAGATCTACACTCTTTCCCTACACGACGCT

CTTCC GATC*T

R = TCR C alpha primer (mouse)
TCCTGAGACCGAGGATCTTTTA

Primers used to isolate Alpha TCR sequences in
PCR 2for Mouse:
F = universal adapter

AATGATACGGCGACCACCGAGATCTACACTCTTTCCCTACACGACGCT

CTTCC GATC*T

R = TCR C alpha primer (mouse)
CAAGCAGAAGACGGCATACGAGAT[CGTGAT]GGTACACAGCAGG

TTCTGGGT TCTGGATGT

Primers used to isolate Beta TCR sequences in
PCR 1 for Mouse:
F = universal adapter

AATGATACGGCGACCACCGAGATCTACACTCTTTCCCTACACGACGC

TCTTCC GATC*T

R = TCR C beta primer (mouse)
AAGGAGACCTTGGGTGGAGTCA

Primers used to isolate Beta TCR sequences in
PCR 1 for Mouse:
F = universal adapter

AATGATACGGCGACCACCGAGATCTACACTCTTTCCCTACACGACGC

TCTTCC GATC*T

R = TCR C beta primer (mouse)
CAAGCAGAAGACGGCATACGAGAT[TGGTCA]CCTTGGGTGGAGT

CACATTTC TCAGATCCT

Primers used to isolate Alpha TCR sequences in
PCR 1 for Human:
F = universal adapter

AATGATACGGCGACCACCGAGATCTACACTCTTTCCCTACACGACGC

TCTTCC GATC*T
R = TCR C alpha primer (human)
CACTGGATTTAGAGTCTCTCAGC

Primers used to isoate Alpha TCR sequences in
PCR 2 for Human:
F = universal adapter

AATGATACGGCGACCACCGAGATCTACACTCTTTCCCTACACGACGC

TCTTCC GATC*T

R = TCR C alpha primer (human)
CAAGCAGAAGACGGCATACGAGAT[TGGTCA]GTGACTGGAGTTCA

GACGTGTG CTCTTCCGATCTNNNGCTGGTACACGGCAGGGTCA

Primers used to isolate Beta TCR sequences in
PCR 1 for Human:
F = universal adapter
AATGATACGGCGACCACCGAGATCTACACTCTTTCCCTACACGACGC

TCTTCC GATC*T

R = TCR C beta primer (human) TGCTTCTGATGGCTCAAACA

Primers used to isolate Beta TCR sequences in
PCR 2 for Human:
F = universal adapter

AATGATACGGCGACCACCGAGATCTACACTCTTTCCCTACACGACGC

TCTTCC GATC*T

R = TCR C beta primer (human)
CAAGCAGAAGACGGCATACGAGAT[CACTGT]GTGACTGGAGTTCA

GACGTGTG CTCTTCCGATCTNNNNNNCAGCGACCTCGGGTGGGAAC
```

Example 4: Correlation of HLA Haplotypes with TCR Diversity in Human Peripheral T Cells All cells have HLA class I (A, B, C) molecules that present antigens to the immune system (CD8+ T cells). Upon recognition, the presenting cells are killed. When the CD8+ cells recognize self-antigens, then auto-immunity is triggered. It has been shown various HLA class I alleles determine disease prognosis. HLA haplotypes have been delineated in various populations, and the information is available. HLA typing is often used to match transplant patients with the organ donor.

The role of HLA in shaping the TCR repertoire is clearly seen in the example of hypersensitive reaction (HSR) to Abacavir, (ABC), a treatment for HIV. The ABC HSR is a multi-organ clinical syndrome typically seen within the initial 6 weeks of ABC treatment. This reaction has been reported in 5%-8% of patients participating in clinical trials.

Patients with the HLA allele HLA-B*5701 exhibit HSR, which is believed to be a class I MHC disease mediated by HLA-B*5701 restricted CD8+ lymphocytes.

Genotyping patients for HLA (Class I and Class II) will be useful in understanding the nature of the TCR repertoire and its response to various stimuli. Stratifying the population by the HLA haplotypes will cluster the TCR repertoires into groups and give it some structure. For example, in celiac disease it has been shown that being homozygous for certain haplotypes leads to celiac disease, and heterozygous individuals present increased risk. By stratifying patients based on HLA, additional risk variants were discovered, which would not have been discovered otherwise.

Figure 25:
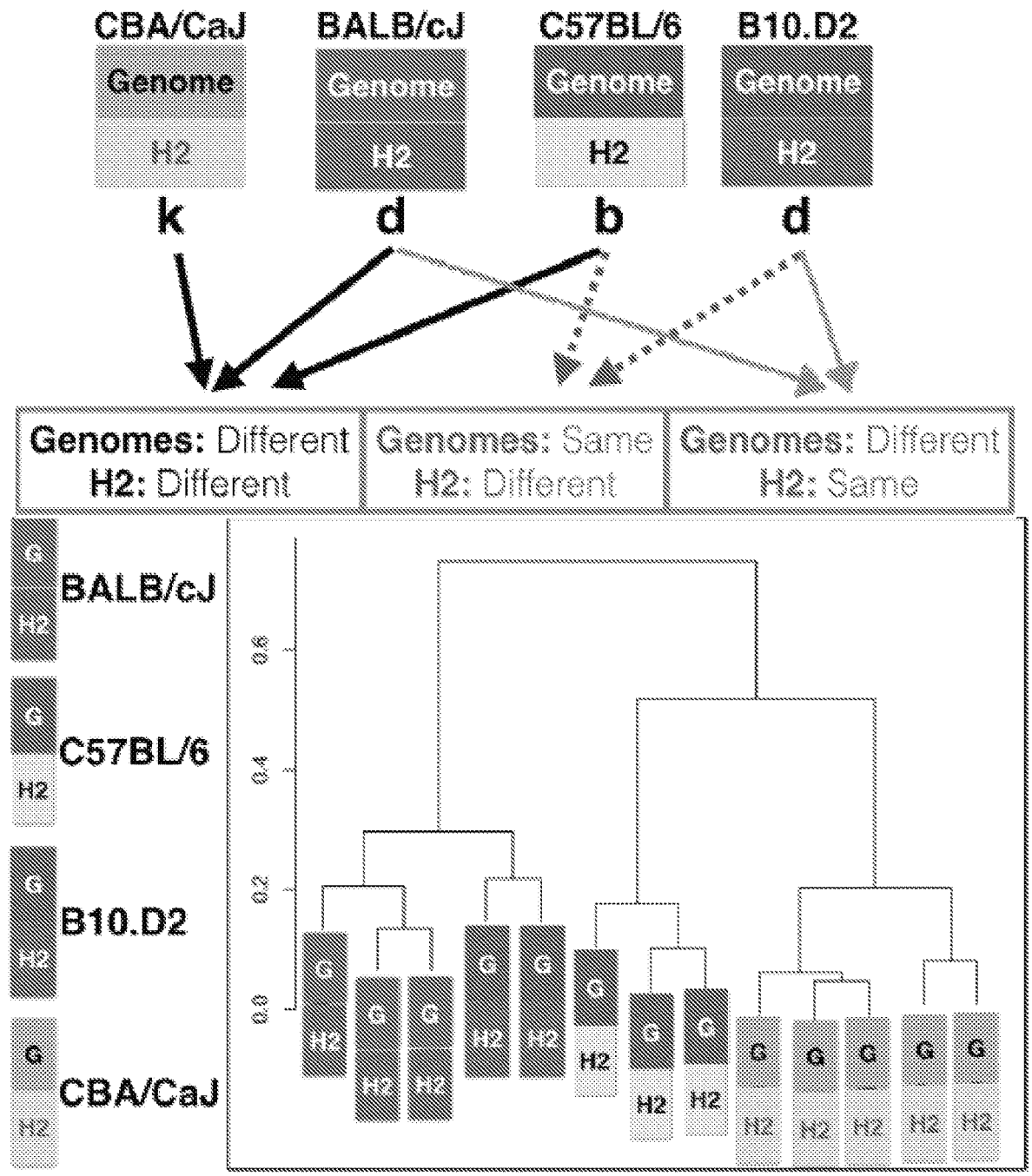
FIG. 25: Clustering based on V-J β combinations across multiple mice from four different strains, C57BL/6, BALB/cJ, CBA/CaJ, and B10.D2.
Figure 26:
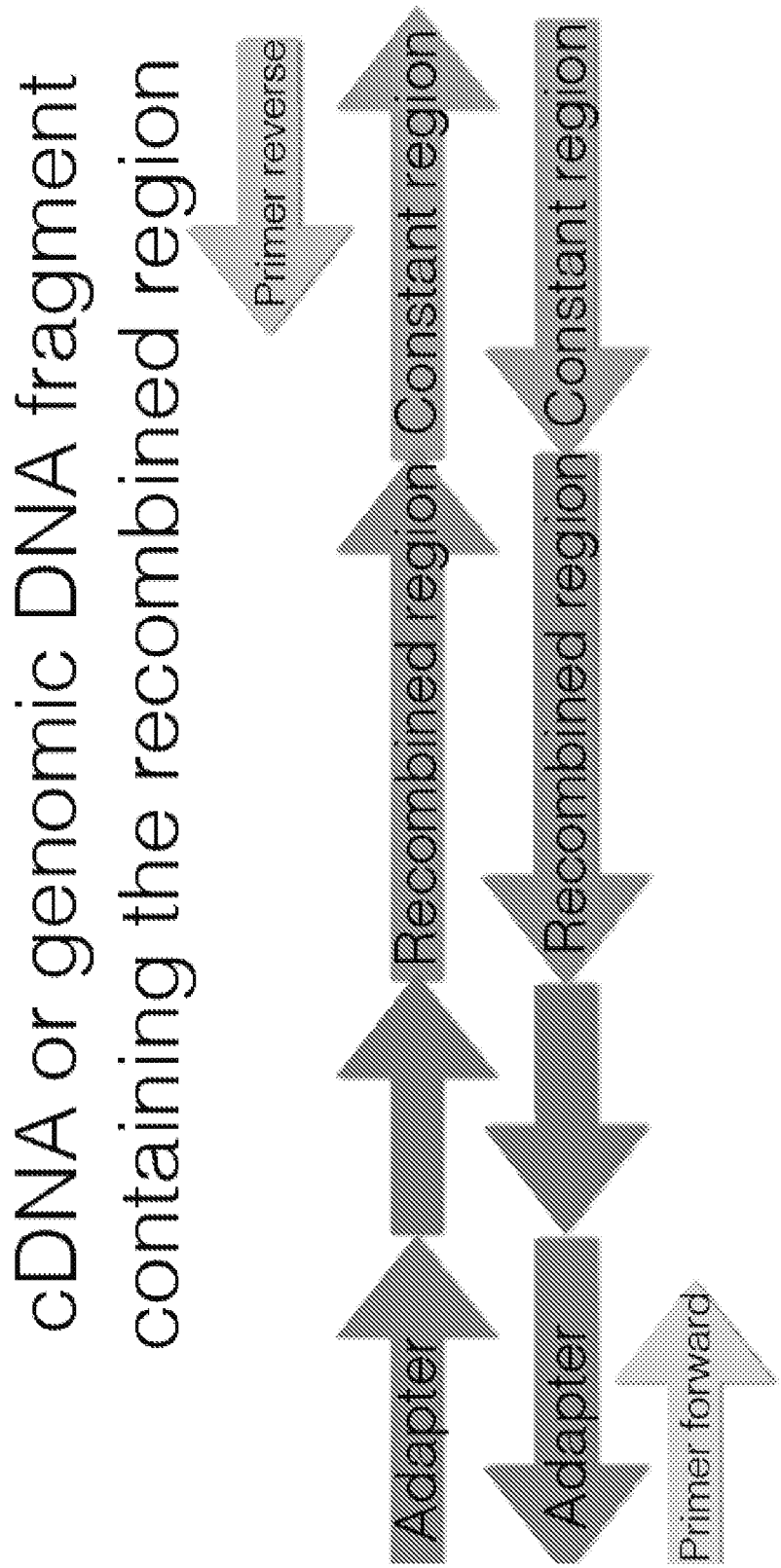
FIG. 26: Illustrates an amplification scheme starting from cDNA or genomic DNA fragments containing the recombined region, in accordance with some implementations.

This was demonstrated in mice by sequencing the TCR repertoire in triplicate from four strains: Black 6 (C57Bl/6J), Balb, CBA/CAJ, and B10D2. Balb and B10D2 share the same MHC, while Black6 and B10D2 share the same genome but have different MHC. CBA/CAJ has a different MHC and genome from the others. As shown in FIG. 25, when the T-seq data is clustered on the basis of the V-J combinations (for β), the MHC seems to be the primary determinant of the diversity of the repertoire.

As shown at the top of FIG. 25, they share or differ in the H2 locus and the rest of the genome. Spearman rank correlation is used to infer distances between any two mice using the frequencies of the V-J β combinations. The strains cluster together on the basis of the H2 locus (the lower colored rectangles) rather than the genome (the upper colored rectangles) implying the MHC has a stronger influence on the TCR repertoire than the rest of the genome. Surprisingly, different mice from the same background share similar repertoires suggesting the repertoires are stable under quiescent conditions. This means that repertoire data can be compared over time to track changes and identify patterns.

We will purchase custom capture reagents for the HLA locus in humans (Class I and Class II, spanning ~3.37 Mb). The capture reagents will be used to capture fragment DNA from the HLA locus of the individuals, and sequenced to at least 50× coverage.

Software was developed to analyze mRNAseq data and classify the HLA genotypes, based on a database of HLA types maintained at Sanger. This software (unpublished) has been successful in rapidly classifying mRNA seq data from 600 human brain samples. We will use this software to classify the DNA data that we generate using the HLA capture reagents. Machine-learning methods, such as non-negative matrix decomposition will be used to identify the effects of features of HLA on the TCR repertoire. This will also generate reference data for use in other projects.

HLA adds another layer to the repertoire data, allowing for finer resolution of correlations. Especially since HLA is already implicated in autoimmune disorders, we expect HLA to provide more help in studying correlations with medical disorders.

Example 5: Determination of B Cell Receptor (BCR) Repertoire to Study B Cell Infiltrants is Diseased Thyroid Tissues The T-seq methods, described herein, will be applied to thyroid samples from GD patients as well as controls, before, during and after treatment, in order to correlate the state of the TCR and BCR repertoire with the treatment outcomes. T-seq will also be used to study the TCR repertoire from Tregs, memory T cells and CD8+ T cells from PBMCs.

Thyroid samples from patients and controls will be collected as part of standard clinical practice, independent of this study. Normal and Graves' thyroid tissue (n=100) will be used from thyroidectomy specimens. Graves' disease will be defined, for this study, as a history of biochemical hyperthyroidism, a diffuse goiter, and either a normal or increased 24 hour radioactive iodine update and/or the presence of TSH receptor antibodies (TSHR-Ab). Normal tissue will be collected from patients having thyroid surgery for benign nodules. These studies will establish the use of TCR repertoire in non-invasive diagnostics.

The exquisite sensitivity of Tseq also enables identification of the signatures of T cells that infiltrate the tissues of affected patients. mRNAseq data generated by us points to the autoimmune response pathways, which play a key role in the chronic stage of the disease, further suggesting that the TCR repertoire will be an important source of information regarding the course of the disease and prognosis.

The processing of the samples will follow protocols already established in the mRNA-seq study that compared mRNA from thyroid tissue of controls and patients (FIG. 21). T-seq will be used for BCR repertoire sequencing, in order to profile infiltrant B cells in thyroid samples. We will use T-seq on thyroid samples to determine the BCR and TCR repertoires from the infiltrates. We will use T-seq to determine the TCR repertoires of the CD8+, CD4+, memory and Treg T cells sorted from PBMCs using FACS. CD8+ T cells have shown signatures of monoclonal expansion. In cases with limited T cells, such as thyroidal samples, the total T cell population will be profiled. HLA profiling will also be carried out on DNA derived from the PBMC.

The analytical tools described herein will be used to derive signatures in the TCR repertoire derived from the thyroid tissues and PBMCs. We will stratify the samples according to the HLA types of the samples to enable easier detection of signals. We will develop software to identify signatures of clonally expanded parts of the repertoire in various sub classes of T cells. Comparison of BCR and TCR repertoire profiles from thyroid tissues of normal and GD patients will also help identify signals in the repertoires.

Additionally, we will compare the TCR repertoire profiles derived from PBMCs to the repertoires derived from thyroid tissues to identify correlations (or anti-correlations) in signatures. We should either see signatures of clonal expansion in the PBMC-derived repertoires, or else see a depletion of certain parts of the repertoire due to recruitment to the affected tissue.

We expect the TCR and BCR repertoire profile for thyroid tissue from patients to show signatures of the treatment and disease progression. The TCR repertoire from PBMCs could have signatures of T cell recruitment to the thyroid tissue, either as a depletion in the PBMC derived TCR repertoire or as a "spillover" from the excess in thyroid tissues. We expect the signatures to enable prediction of outcomes (prognosis) and help tailor treatments. Long-term, we expect the identification of features in the TCR repertoire to lead to personalized treatments with antigens targeting specific parts of the repertoire. We expect this study to provide a roadmap for the study of other autoimmune disorders, as it is rare to have such detailed access to tissues and samples in most other cases.

REFERENCES

All headings and section designations are used for clarity and reference purposes only and are not to be considered limiting in any way. For example, those of skill in the art will appreciate the usefulness of combining various aspects from different headings as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed:

1. A universal primer based method for determining recombination diversity at a genomic locus of interest in a subject, the method comprising:
   a) isolating nucleic acids from a biological sample containing immune cells from the subject;
   b) fragmenting the isolated nucleic acids, thereby forming a plurality of fragmented nucleic acids, wherein the plurality of fragmented nucleic acids contains a sub-plurality of at least 10 fragmented nucleic acids having a recombined junction and a constant region from the genomic locus of interest, wherein the fragments are at least 100 bp;
   c) ligating first adaptor nucleic acids to the ends of respective nucleic acids corresponding to the plurality of fragmented nucleic acids, the first adaptor nucleic acids comprising a first hybridization region having a first predefined hybridization sequence, thereby forming a plurality of ligated nucleic acid fragments;
   d) selectively amplifying respective ligated nucleic acid fragments, in the plurality of ligated nucleic acid fragments, containing the recombined junction using only universal primers:
      when the recombined junction is 5' to the constant region:
         i) a first universal primer that hybridizes, at the first hybridization region, to the Crick strand of respective ligated nucleic acid fragments in the plurality of ligated nucleic acid fragments; and
         ii) a second universal primer that hybridizes, at a first site in the constant region 3' to the recombined junction at the genomic locus of interest, to the Watson strand of respective ligated nucleic acids containing the recombined junction at the genomic locus of interest in the plurality of ligated nucleic acid fragments, or
      when the recombined junction is 3' to the constant region:
         i) a first universal primer that hybridizes, at the first hybridization region, to the Watson strand of respective ligated nucleic acid fragments in the plurality of ligated nucleic acid fragments; and
         ii) a second universal primer that hybridizes, at a first site in the constant region 5' to the recombined junction at the genomic locus of interest, to the Crick strand of respective ligated nucleic acids containing the recombined junction at the genomic locus of interest in the plurality of ligated nucleic acid fragments,
   thereby forming a plurality of amplified nucleic acid fragments, from the sub-plurality of at least 10 fragmented nucleic acids, having recombined junctions at the genomic locus of interest, wherein >90% of the amplified nucleic acid fragments comprise CDR3 sequences; and
   e) sequencing amplified nucleic acid fragments in the plurality of amplified nucleic acid fragments,
   wherein the genomic locus of interest is selected from the group consisting of a T cell receptor α-locus, a T cell receptor β-locus, a T cell receptor γ-locus, a T cell receptor δ-locus, a B cell receptor κ-heavy chain locus, a B cell receptor κ-light chain locus, a B cell receptor λ-heavy chain locus, a B cell receptor λ-light chain locus, a B cell receptor σ-heavy chain locus, and a B cell receptor σ-light chain locus.

2. The universal primer based method according to claim 1, wherein the nucleic acids isolated in a) are RNA and the plurality of fragmented nucleic acids in b) are fragmented RNA, the method further comprising:
   b1) preparing cDNA from the plurality of fragmented RNA formed in b), such that the first adaptor molecules are ligated to the prepared cDNA in c).

3. The universal primer based method according to claim 1, wherein the nucleic acids isolated in a) are RNA or genomic DNA, and the plurality of fragmented nucleic acids in b) are fragmented RNA or genomic DNA, such that the first adaptor molecules are ligated to the fragmented RNA or fragment genomic DNA in c), the method further comprising:
   b1) preparing cDNA from the fragmented RNA or fragmented genomic DNA that are ligated in c).

4. The universal primer based method according to claim 1, wherein the sub-plurality of fragmented nucleic acids contains at least 15 fragmented nucleic acids having a recombined junction and a constant region from the genomic locus of interest.

5. The universal primer based method according to claim 1, wherein the biological sample comprises a population of T cells or B cells from the subject.

6. The universal primer based method according to claim 1, wherein the plurality of fragmented nucleic acids have a mean fragment length of at least 150 nucleotides and less than 600 nucleotides.

7. The universal primer based method according to claim 1, wherein the first adaptor nucleic acids are a plurality of first adaptor nucleic acids, each respective first adaptor nucleic acid in the plurality of first adaptor nucleic acids comprising a first portion and a second portion, the second portion positioned at the 3' end of the first portion on the Watson strand of the adaptor nucleic acid, and wherein:
   the first portion of each respective first adaptor nucleic acid comprises the first hybridization region having the first predefined hybridization sequence,
   the second portion of each respective first adaptor nucleic acid comprises an indexing region having one of a plurality of indexing sequences, and
   the plurality of first adaptor molecules includes at least two respective first adaptor molecules with different indexing sequences.

8. The universal primer based method according to claim 1, wherein selectively amplifying the ligated nucleic acid fragments in d) is performed via a single PCR amplification reaction using said first and second universal primers.

9. The universal primer based method according to claim 8, wherein the second universal primer comprises a first portion, a second portion positioned at the 3' end of the first portion, and a third portion positioned at the 3' end of the second portion, wherein:
  the first portion of the second universal primer comprises a second hybridization region having a second predefined hybridization sequence,
  the second portion comprises a bar code region having a bar code sequence, and
  the third sequence comprises a hybridization region having a sequence that hybridizes, at the first site in the constant region 3' to the recombined junction at the genomic locus of interest, to the Watson strand of respective ligated nucleic acids containing the recombined junction at the genomic locus of interest in the plurality of ligated nucleic acid fragments.

10. The universal primer based method according to claim 1, wherein selectively amplifying the ligated nucleic acid fragments in d) is performed via a series of nested PCR amplification reactions comprising:
  i) a first PCR amplification reaction using said first and second universal primers; and
  ii) a second PCR amplification reaction using:
    A) a third primer that hybridizes, at the first hybridization region, to the Crick strand of amplified nucleic acid fragments; and
    B) a fourth primer that hybridizes, at a second site in the constant region 3' to the recombined junction at the genomic locus of interest, to the Watson strand of amplified nucleic acid fragments, the second site located 5' of the first site on the Watson strand of the amplified nucleic acid fragments.

11. The universal primer based method according to claim 10, wherein the fourth primer comprises a first portion, a second portion positioned at the 3' end of the first portion, and a third portion positioned at the 3' end of the second portion, wherein:
  the first portion of the fourth primer comprises a second hybridization region having a second predefined hybridization sequence,
  the second portion comprises a bar code region having a bar code sequence, and
  the third portion comprises a hybridization region having a sequence that hybridizes, at the first site in the constant region 3' to the recombined junction at the genomic locus of interest, to the Watson strand of respective ligated nucleic acids containing the recombined junction at the genomic locus of interest in the plurality of ligated nucleic acid fragments.

12. The universal primer based method according to claim 10, further comprising a third PCR amplification reaction between the first and second PCR amplification reactions.

13. The universal primer based method according to claim 9, wherein sequencing amplified nucleic acid fragments in e) comprises:
  i) mixing amplified nucleic acid fragments from a plurality of subjects, wherein the amplified nucleic acid fragments from each respective subject in the plurality of subjects have a different bar code sequence.

14. The universal primer based method according to claim 1, further comprising:
  f) annotating the sequence of the recombined junction at the genomic locus of interest in respective amplified nucleic acid fragments sequenced in e);
  g) assembling a recombination profile of the subject comprising the annotated sequences of recombined junctions at the genomic locus of interest; and
  h) comparing the subject's recombination profile to a reference profile.

15. The universal primer based method according to claim 7, further comprising:
  j) determining a relative clonal number of a respective recombined junction at the genomic locus of interest by determining the number of times the sequence of the recombined junction is associated with a respective indexing sequence, in the plurality of indexing sequences, from a first adaptor nucleic acid.

16. A universal primer based method for generating a T-cell receptor repertoire (TCRR) from a cell population comprising a T-cell population, the method comprising:
  a) isolating mRNA from said cell population comprising a T-cell population;
  b) fragmenting said mRNA to obtain a collection of mRNA fragments having a mean fragment length that is at least 100 bp and less than 600 bp;
  c) preparing cDNA from said collection of fragments;
  d) ligating at least a first adapter module to said cDNA; wherein said first adapter module ligates to a first end of said cDNA;
  e) performing a first round of PCR amplification using a first universal primer and a second universal primer, wherein said first universal primer binds to a first region and said second universal primer binds to a second region in said first round of PCR amplification, wherein the first region is at least partially in said first adapter and said second region is in the C-region, thereby obtaining a plurality of first amplified products, wherein >90% of the first amplified products comprise CDR3 sequences; and
  f) performing a second round of PCR amplification on said plurality of first amplified products using a third primer and a fourth primer thereby deriving a plurality of second amplified products, wherein
    said third primer binds to a third region and said fourth primer binds to a fourth region in said second round of PCR amplification,
    said third region is at least partially in the first adapter and said fourth region is in the C-region,
    an average nucleotide distance between the first and the second region across the plurality of first amplified products is greater than an average nucleotide distance between the third region and the fourth region across the plurality of second amplified products, and
    the fourth region is located at least partially between the first and second regions.

17. The universal primer based method according to claim 16, wherein (i) said ligating in d) results in ligation of a second adapter module to said cDNA, (ii) said second adapter module is the same or different than said first adapter module, and (iii) said second adapter module ligates to a second end of said cDNA.

18. The universal primer based method according to claim 16, wherein said TCRR is for an alpha T-cell receptor repertoire or for a beta T-cell repertoire.

19. The universal primer based method according to claim 16, wherein said first primer and said third primer comprise the same or different sequences.

20. The universal primer based method according to claim 16, wherein only universal primers are utilized.

* * * * *

SEQUENCE LISTING

```
<160> NUMBER OF SEQ ID NOS: 18

<210> SEQ ID NO 1
<211> LENGTH: 58
<212> TYPE: DNA
<213> ORGANISM: Artificial Sequence
<220> FEATURE:
<223> OTHER INFORMATION: synthetic

<400> SEQUENCE: 1
aatgatacgg cgaccaccga gatctacact ctttccctac acgacgctct tccgatct        58

<210> SEQ ID NO 2
<211> LENGTH: 22
<212> TYPE: DNA
<213> ORGANISM: Artificial Sequence
<220> FEATURE:
<223> OTHER INFORMATION: synthetic

<400> SEQUENCE: 2
tcctgagacc gaggatcttt ta                                                22

<210> SEQ ID NO 3
<211> LENGTH: 60
<212> TYPE: DNA
<213> ORGANISM: Artificial Sequence
<220> FEATURE:
<223> OTHER INFORMATION: synthetic

<400> SEQUENCE: 3
caagcagaag acggcatacg agatcgtgat ggtacacagc aggttctggg ttctggatgt      60

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
aaggagacct tgggtggagt ca                                                22

<210> SEQ ID NO 5
<211> LENGTH: 60
<212> TYPE: DNA
<213> ORGANISM: Artificial Sequence
<220> FEATURE:
<223> OTHER INFORMATION: synthetic

<400> SEQUENCE: 5
caagcagaag acggcatacg agattggtca ccttgggtgg agtcacattt ctcagatcct      60

<210> SEQ ID NO 6
<211> LENGTH: 23
```

<212> TYPE: DNA
<213> ORGANISM: Artificial Sequence
<220> FEATURE:
<223> OTHER INFORMATION: synthetic

<400> SEQUENCE: 6
cactggattt agagtctctc agc                                    23

<210> SEQ ID NO 7
<211> LENGTH: 87
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (65)..(67)
<223> OTHER INFORMATION: n is a, c, g, or t

<400> SEQUENCE: 7
caagcagaag acggcatacg agattggtca gtgactggag ttcagacgtg tgctcttccg    60
atctnnngct ggtacacggc agggtca                                       87

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
tgcttctgat ggctcaaaca                                        20

<210> SEQ ID NO 9
<211> LENGTH: 90
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (65)..(70)
<223> OTHER INFORMATION: n is a, c, g, or t

<400> SEQUENCE: 9
caagcagaag acggcatacg agatcactgt gtgactggag ttcagacgtg tgctcttccg    60
atctnnnnnn cagcgacctc gggtgggaac                                    90

<210> SEQ ID NO 10
<211> LENGTH: 40
<212> TYPE: DNA
<213> ORGANISM: Artificial Sequence
<220> FEATURE:
<223> OTHER INFORMATION: synthetic

<400> SEQUENCE: 10
tactgcacct gcagtgcaga caattctgga aatacgctct                  40

<210> SEQ ID NO 11
<211> LENGTH: 13
<212> TYPE: PRT
<213> ORGANISM: Artificial Sequence
<220> FEATURE:
<223> OTHER INFORMATION: synthetic

<400> SEQUENCE: 11

Tyr Cys Thr Cys Ser Ala Asp Asn Ser Gly Asn Thr Leu
1               5                   10

<210> SEQ ID NO 12
<211> LENGTH: 40
<212> TYPE: DNA
<213> ORGANISM: Artificial Sequence
<220> FEATURE:
<223> OTHER INFORMATION: synthetic

<400> SEQUENCE: 12
tactgcacct gcagtgcaga tgcagaaacg ctgtattttg          40

<210> SEQ ID NO 13
<211> LENGTH: 13
<212> TYPE: PRT
<213> ORGANISM: Artificial Sequence
<220> FEATURE:
<223> OTHER INFORMATION: synthetic

<400> SEQUENCE: 13

Tyr Cys Thr Cys Ser Ala Asp Ala Glu Thr Leu Tyr Phe
1               5                   10

<210> SEQ ID NO 14
<211> LENGTH: 40
<212> TYPE: DNA
<213> ORGANISM: Artificial Sequence
<220> FEATURE:
<223> OTHER INFORMATION: synthetic

<400> SEQUENCE: 14
ttttgtgcca gcagccaagg acagtatgaa cagtacttcg          40

<210> SEQ ID NO 15
<211> LENGTH: 13
<212> TYPE: PRT
<213> ORGANISM: Artificial Sequence
<220> FEATURE:
<223> OTHER INFORMATION: synthetic

<400> SEQUENCE: 15

Phe Cys Ala Ser Ser Gln Gly Gln Tyr Glu Gln Tyr Phe
1               5                   10

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
gctggtacac ggcagggtca                                20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
tgcttctgat ggctcaaaca                                20

<210> SEQ ID NO 18

```
<211> LENGTH: 20
<212> TYPE: DNA
<213> ORGANISM: Artificial Sequence
<220> FEATURE:
<223> OTHER INFORMATION: synthetic

<400> SEQUENCE: 18
cagcgacctc gggtgggaac                                                      20
```